(12) United States Patent
Lamego et al.

(10) Patent No.: US 9,649,054 B2
(45) Date of Patent: May 16, 2017

(54) BLOOD PRESSURE MEASUREMENT METHOD

(75) Inventors: Marcelo Lamego, Coto de Caza, CA (US); Massi Joe E. Kiani, Laguna Niguel, CA (US); Ken Lam, Walnut, CA (US); Cristiano Dalvi, Irvine, CA (US); Hung Vo, Garden Grove, CA (US)

(73) Assignee: CERCACOR LABORATORIES, INC., Irvine, CA (US)

( * ) Notice: Subject to any disclaimer, the term of this patent is extended or adjusted under 35 U.S.C. 154(b) by 477 days.

(21) Appl. No.: 13/218,373

(22) Filed: Aug. 25, 2011

(65) Prior Publication Data

US 2012/0059267 A1 Mar. 8, 2012

Related U.S. Application Data

(60) Provisional application No. 61/377,192, filed on Aug. 26, 2010, provisional application No. 61/499,515, filed on Jun. 21, 2011.

(51) Int. Cl.
*A61B 5/02* (2006.01)
*A61B 5/1455* (2006.01)
(Continued)

(52) U.S. Cl.
CPC ............ *A61B 5/1455* (2013.01); *A61B 5/021* (2013.01); *A61B 5/022* (2013.01); *A61B 5/14532* (2013.01); *A61B 5/721* (2013.01)

(58) Field of Classification Search
USPC ....................................................... 600/483
See application file for complete search history.

(56) References Cited

U.S. PATENT DOCUMENTS 4,960,128 A 10/1990 Gordon et al.
4,964,408 A 10/1990 Hink et al.
(Continued)

FOREIGN PATENT DOCUMENTS

WO WO 98/15224 4/1998
WO WO 98/17172 4/1998
WO WO 2007/147069 12/2007

OTHER PUBLICATIONS

US 8,845,543, 09/2014, Diab et al. (withdrawn)
(Continued)

*Primary Examiner* — Navin Natnithithadha
*Assistant Examiner* — Michael R Bloch
(74) *Attorney, Agent, or Firm* — Knobbe, Martens, Olson & Bear, LLP

(57) ABSTRACT

A blood pressure measurement system that non-invasively determines an individual's blood pressure can include a noninvasive blood pressure sensor having an optical sensor and a motion sensor. The optical sensor can provide a photoplethysmograph signal obtained from a patient to a processor. The motion sensor can provide a motion signal to the processor responsive to motion of the patient. In one embodiment, the processor calculates or estimates the blood pressure of the patient based on the photoplethysmograph signal and the motion signal. Advantageously, the system can obtain this blood pressure measurement without an occlusive cuff, thereby reducing patient discomfort. In other implementations, the processor calculates a blood pressure-related parameter from the photoplethysmograph and motion signal. The processor can occasionally trigger an occlusive cuff measurement as this parameter changes, thereby reducing the frequency of occlusive cuff measurements.

7 Claims, 27 Drawing Sheets

(51) Int. Cl.
*A61B 5/021* (2006.01)
*A61B 5/022* (2006.01)
*A61B 5/145* (2006.01)
*A61B 5/00* (2006.01)

(56) References Cited

U.S. PATENT DOCUMENTS

| | | | |
|---|---|---|---|
| 5,041,187 A | 8/1991 | Hink et al. | |
| 5,069,213 A | 12/1991 | Polczynski | |
| 5,163,438 A | 11/1992 | Gordon et al. | |
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,534,851 A | 7/1996 | Russek | |
| 5,561,275 A | 10/1996 | Savage et al. | |
| 5,562,002 A | 10/1996 | Lalin | |
| 5,588,427 A * | 12/1996 | Tien | 600/323 |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A * | 9/1998 | Caro | A61B 5/022 600/301 |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,964,701 A * | 10/1999 | Asada et al. | 600/300 |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,018,673 A * | 1/2000 | Chin et al. | 600/322 |
| 6,027,452 A | 2/2000 | Flaherty et al. | |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,081,742 A * | 6/2000 | Amano et al. | 600/513 |
| 6,088,607 A | 7/2000 | Diab et al. | |
| 6,110,522 A | 8/2000 | Lepper, Jr. et al. | |
| 6,124,597 A | 9/2000 | Shehada | |
| 6,128,521 A | 10/2000 | Marro et al. | |
| 6,129,675 A | 10/2000 | Jay | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,253,097 B1 | 6/2001 | Aronow et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,301,493 B1 | 10/2001 | Marro et al. | |
| 6,317,627 B1 | 11/2001 | Ennen et al. | |
| 6,321,100 B1 | 11/2001 | Parker | |
| 6,325,761 B1 | 12/2001 | Jay | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,430,437 B1 | 8/2002 | Marro | |
| 6,430,525 B1 | 8/2002 | Weber et al. | |
| 6,434,408 B1 * | 8/2002 | Heckel | 600/336 |
| 6,463,311 B1 | 10/2002 | Diab | |
| 6,470,199 B1 | 10/2002 | Kopotic et al. | |
| 6,501,975 B2 | 12/2002 | Diab et al. | |
| 6,505,059 B1 | 1/2003 | Kollias et al. | |
| 6,515,273 B2 | 2/2003 | Al-Ali | |
| 6,519,487 B1 | 2/2003 | Parker | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,595,316 B2 | 7/2003 | Cybulski et al. | |
| 6,597,932 B2 | 7/2003 | Tian et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,639,668 B1 | 10/2003 | Trepagnier | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Kiani et al. | |
| 6,661,161 B1 | 12/2003 | Lanzo et al. | |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,684,091 B2 | 1/2004 | Parker | |
| 6,697,656 B1 | 2/2004 | Al-Ali | |
| 6,697,657 B1 | 2/2004 | Shehada et al. | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,721,582 B2 | 4/2004 | Trepagnier et al. | |
| 6,721,585 B1 | 4/2004 | Parker | |
| 6,725,075 B2 | 4/2004 | Al-Ali | |
| 6,728,560 B2 | 4/2004 | Kollias et al. | |
| 6,735,459 B2 | 5/2004 | Parker | |
| 6,745,060 B2 | 6/2004 | Diab et al. | |
| 6,760,607 B2 | 7/2004 | Al-Ali | |
| 6,770,028 B1 | 8/2004 | Ali et al. | |
| 6,771,994 B2 | 8/2004 | Kiani et al. | |
| 6,792,300 B1 | 9/2004 | Diab et al. | |
| 6,813,511 B2 | 11/2004 | Diab et al. | |

(56) References Cited

U.S. PATENT DOCUMENTS

| | | | |
|---|---|---|---|
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,923,769 B2 * | 8/2005 | Nishii et al. ............ 600/485 |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |

(56) References Cited

U.S. PATENT DOCUMENTS

| | | |
|---|---|---|
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |

(56) References Cited

U.S. PATENT DOCUMENTS

| | | |
|---|---|---|
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 2005/0228301 A1* | 10/2005 | Banet et al. .................. 600/485 |
| 2007/0185401 A1 | 8/2007 | Quinn et al. |
| 2009/0326395 A1* | 12/2009 | Watson .......................... 600/500 |
| 2010/0125188 A1 | 5/2010 | Schilling et al. |
| 2010/0298655 A1* | 11/2010 | McCombie et al. .......... 600/301 |
| 2011/0021929 A1* | 1/2011 | Sethi et al. .................... 600/485 |
| 2011/0172967 A1 | 7/2011 | Al-Ali et al. |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2012/0059267 A1 | 3/2012 | Lamego et al. |
| 2012/0116175 A1 | 5/2012 | Al-Ali et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0265039 A1 | 10/2012 | Kiani |
| 2012/0283524 A1 | 11/2012 | Kiani et al. |
| 2012/0286955 A1 | 11/2012 | Welch et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0079610 A1 | 3/2013 | Al-Ali |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0178749 A1 | 7/2013 | Lamego |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | O'Neil et al. |
| 2013/0317327 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0324817 A1 | 12/2013 | Diab |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0025306 A1 | 1/2014 | Weber et al. |
| 2014/0034353 A1 | 2/2014 | Al-Ali et al. |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081097 A1 | 3/2014 | Al-Ali et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142399 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |

(56) References Cited

U.S. PATENT DOCUMENTS

2014/0343436 A1    11/2014   Kiani
2015/0018650 A1     1/2015   Al-Ali et al.

OTHER PUBLICATIONS

International Search Report and Written Opinion issued in application No. PCT/US2011/049225 on Nov. 29, 2011.

Wei, "Photoplethysmography Blood Pressure Measurement", Department of Mechanical Engineering, National University of Singapore. 20 pages, accessed online (http://memslab.nus.edu.sg/me4284/AY%200405%20Report/Photoplethysmography%20Blood%20Pressure%20Measurement.pdf) on Nov. 16, 2010.

Onodera et al., "Validation of inflationary non-invasive blood pressure monitoring in adult surgical patients", J. Anesth., 25:127-130 (Dec. 28, 2010).

\* cited by examiner

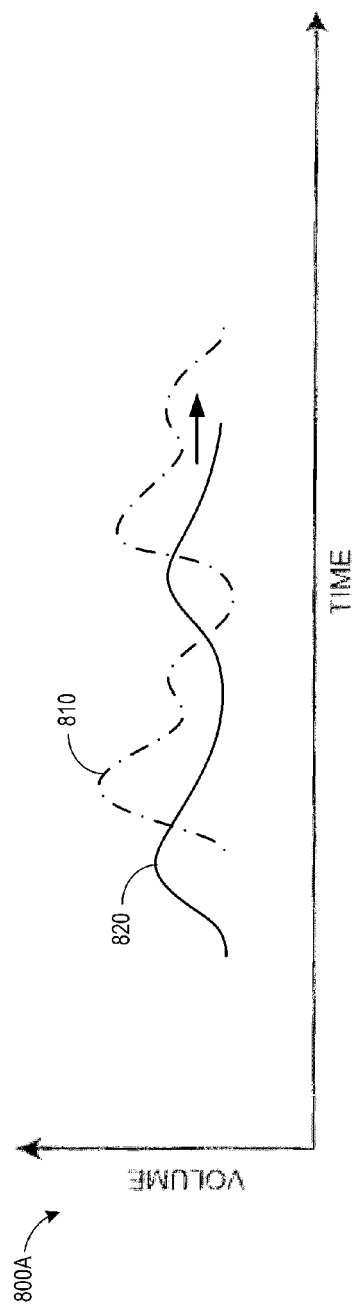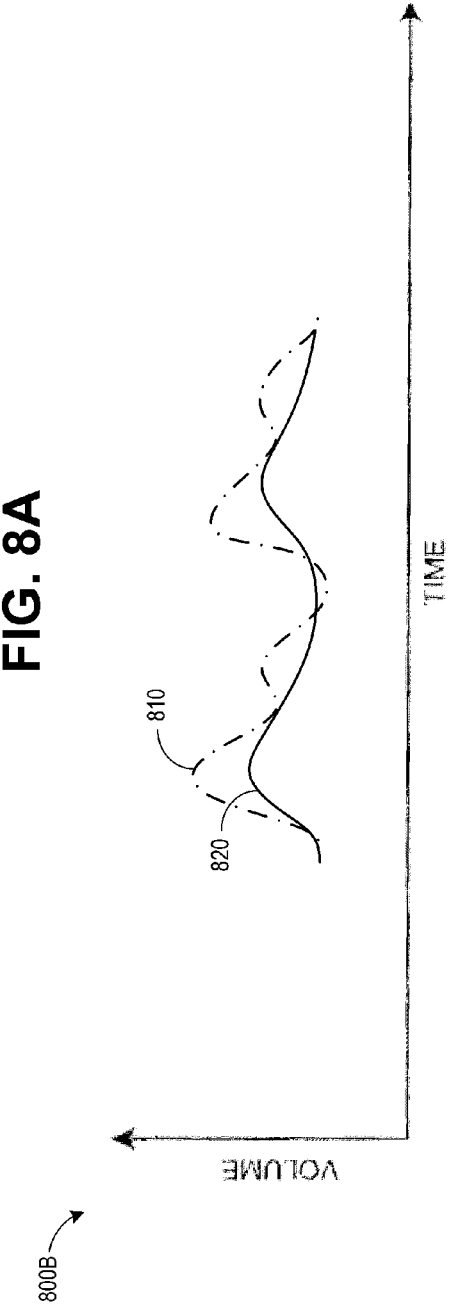
FIG. 8A
FIG. 8B

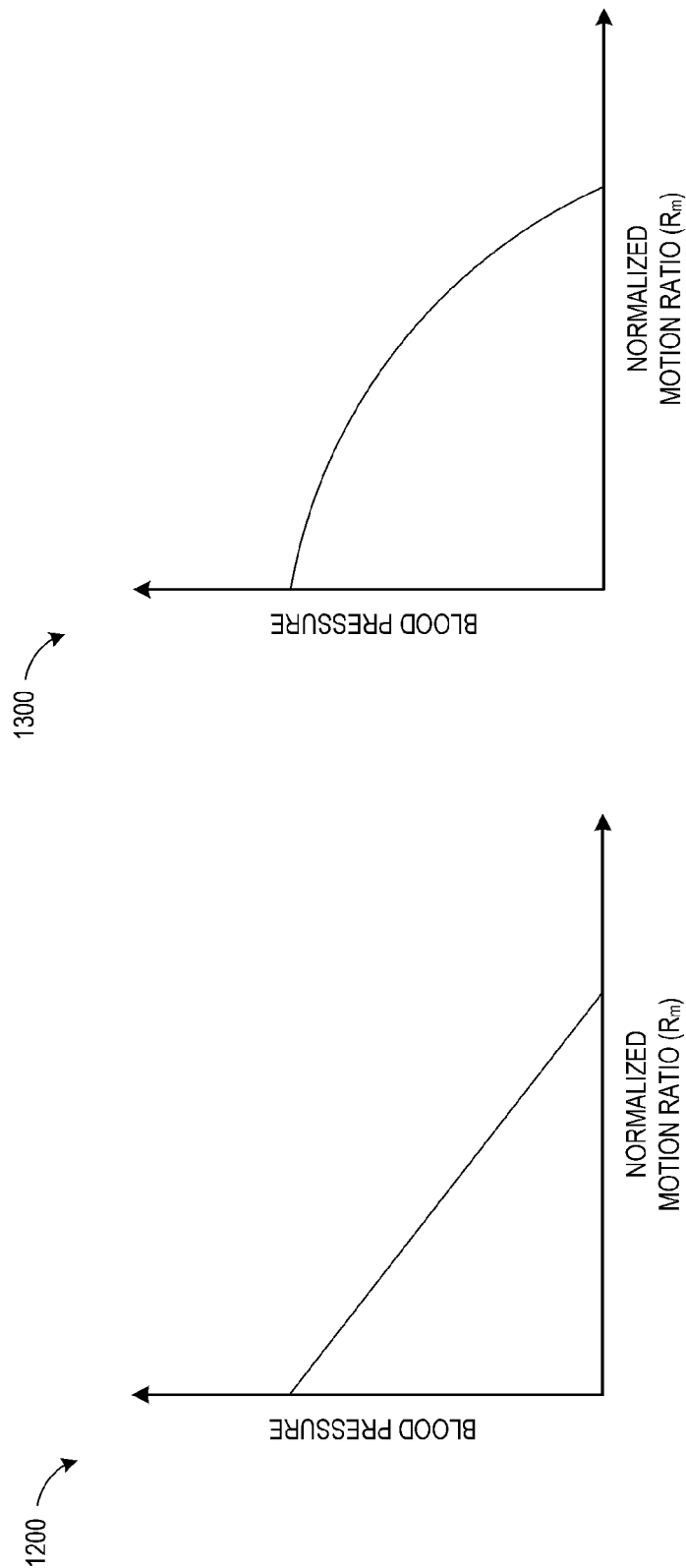

BLOOD PRESSURE MEASUREMENT METHOD

RELATED APPLICATION

This application claims priority under 35 U.S.C. §119(e) to U.S. Provisional Application No. 61/377,192 filed Aug. 26, 2010, entitled "Pulse Oximetry System for Monitoring Blood Pressure," and 61/499,515, filed Jun. 21, 2011, entitled "Blood Pressure Monitoring System," the disclosures of both of which are hereby incorporated by reference in their entirety.

BACKGROUND

Prolonged reduction or loss of blood pressure in a patient severely limits the amount of tissue perfusion of the patient and therefore causes damage to or death of the tissue. Although some tissues can tolerate hypoperfusion for long periods of time, the brain, heart and kidneys are very sensitive to a reduction in blood flow. Thus, during and after medical procedures and at other times, blood pressure is a frequently monitored vital sign. Blood pressure can be affected by the type of medical procedure performed and by physiological factors such as the body's reaction to the medical procedure. Moreover, blood pressure is often manipulated and controlled using various medications. Medical procedures, physiological factors, and medications can cause the blood pressure of a patient to change rapidly.

The traditional method of measuring blood pressure is with a stethoscope, occlusive cuff, and pressure manometer. However, this technique is slow, subjective in nature, involves the intervention of a skilled clinician, and often does not provide timely measurements. Blood pressure cuff instruments make only spot-check measurements, so repetitive interval measurements are often used to trend patient status. More frequent intervals improve vigilance at the expense of patient discomfort and possible patient injury (e.g., due to occlusion of blood vessels or nerve damage).

SUMMARY

In certain embodiments, a sensor for measuring blood pressure includes an optical sensor having an emitter configured to emit light on a measurement site of a patient and a detector configured to detect the light after attenuation by the measurement site and to output a photoplethysmograph signal responsive to the attenuated light. The sensor may further include a motion sensor configured to sense motion of the patient at the measurement site and to provide a motion signal responsive to the sensed motion, wherein the photoplethysmograph signal and the motion signal are configured to be used to derive a blood pressure of the patient.

Additionally, in some embodiments, a method of measuring blood pressure includes obtaining a photoplethysmograph signal from an optical sensor coupled with a patient at a measurement site that is in motion, obtaining a motion signal from a motion sensor coupled with the measurement site, and calculating a blood pressure measurement based at least in part on the photoplethysmograph signal and the motion signal.

In other embodiments, a method for measuring blood pressure includes attaching an inflatable cuff to a person, inflating the cuff at an approximately constant rate using gas from a gas reservoir, and measuring blood pressure of the person while the cuff is inflating. Further, some embodiments include a method of measuring blood pressure that includes obtaining a photoplethysmograph signal from an optical sensor coupled with a patient at a measurement site that is in motion, obtaining a motion signal corresponding to a motion portion of the photoplethysmograph signal, where the motion portion is at least partially induced by the motion at the measurement site, and triggering a blood pressure cuff to take a measurement responsive to the photoplethysmograph signal and the motion signal.

Various embodiments of a blood pressure monitoring system include an inflatable cuff attachable to a wearer, a gas reservoir configured to provide gas to the inflatable cuff via a gas pathway, a sensor configured to obtain blood pressure data from the inflatable cuff, and a patient monitor configured to receive the blood pressure data from the sensor to determine a blood pressure measurement of the wearer. Moreover, embodiments of a blood pressure monitoring system include an inflatable cuff attachable to a wearer, and a gas reservoir comprising compressed gas and configured to provide the compressed gas to the inflatable cuff via a gas pathway.

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Throughout the drawings, reference numbers can be re-used to indicate correspondence between referenced elements. The drawings are provided to illustrate embodiments of the inventions described herein and not to limit the scope thereof.

FIGS. 8A and 8B illustrate plots of example blood pressure and motion waveforms being correlated in time.

FIGS. 12 and 13 illustrate example blood pressure calibration curves.

DETAILED DESCRIPTION

I. Introduction

Noninvasive optical sensors can use spectrophotometry techniques to measure a variety of blood constituents, including for example, glucose, oxygen saturation, hemoglobin, methemoglobin, carboxyhemoglobin, other hemoglobin species, concentrations of the same, and the like. In addition, noninvasive optical sensors can also be used to measure a variety of other physiological parameters, including pulse rate, perfusion, and the like. An optical sensor can include one or more emitters that shine light through tissue of a living person, such as through a finger, toe, or foot. One or more detectors can receive the transmitted light after attenuation by the tissue and can generate one or more signals responsive to the attenuated light. A processor can process the one or more signals to derive measurements of one or more physiological parameters.

This disclosure describes, among other features, a blood pressure measurement system that non-invasively determines an individual's blood pressure. The blood pressure measurement system can include a noninvasive blood pressure sensor having an optical sensor and a motion sensor. The optical sensor can provide a photoplethysmograph signal obtained from a patient to a processor. The motion sensor can provide a motion signal to the processor responsive to motion of the patient. In one embodiment, the processor calculates or estimates the blood pressure of the patient based on the photoplethysmograph signal and the motion signal. Advantageously, the system can obtain this blood pressure measurement without an occlusive cuff, thereby reducing patient discomfort. In other embodiments, the processor calculates a blood pressure-related parameter from the photoplethysmograph and motion signal. The processor can occasionally trigger an occlusive cuff measurement as this parameter changes, thereby reducing the frequency of occlusive cuff measurements.

Further, this disclosure describes a blood pressure monitoring system that can include a gas reservoir filled with sufficient quantities of compressed gas to inflate an inflatable cuff. The gas reservoir can provide several advantages to the blood pressuring monitoring system, including portability, reusability, disposability, reduction in auditory noise and electrical noise, and/or the ability to measure blood pressure during inflation of the blood pressure cuff.

II. Example Parameter Calculation System

Figure 1:
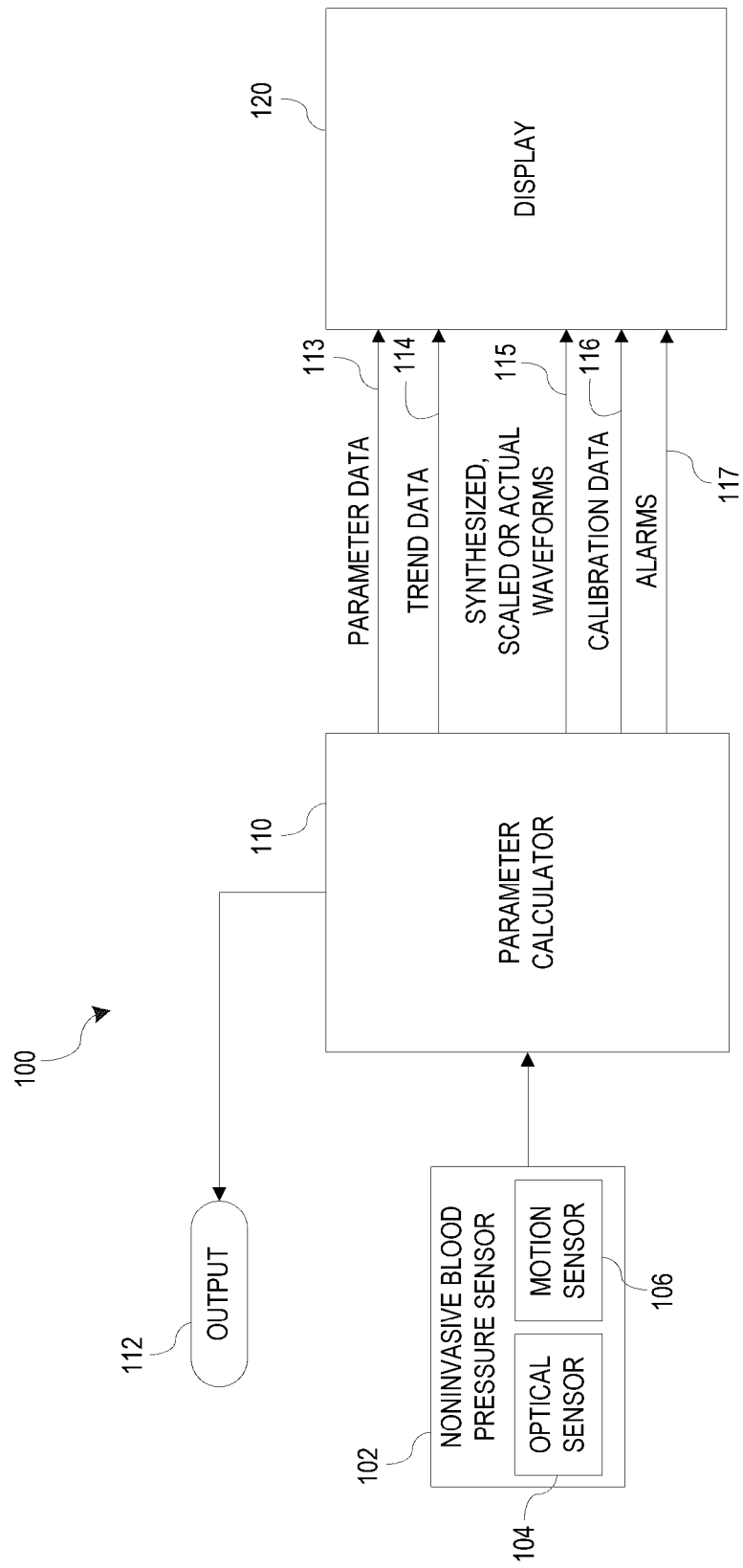
FIG. 1 illustrates an embodiment of a parameter calculation system that can calculate blood pressure, among other parameters.

FIG. 1 illustrates an embodiment of a parameter calculation system 100 that can calculate blood pressure, among other parameters. Advantageously, in certain embodiments, the parameter calculation system 100 noninvasively measures blood pressure of a patient using optical and motion signals. In addition to blood pressure, the parameter calculation system 100 can measure other physiological parameters in some implementations. Some examples of other parameters that may be measured include pulse rate, oxygen saturation ($SpO_2$), hemoglobin, total hemoglobin, hemoglobin species (e.g., methemoglobin, carboxyhemoglobin, or the like), carbon monoxide or dioxide, perfusion, glucose, and the like.

The parameter calculation system 100 shown includes a noninvasive blood pressure sensor 102. The blood pressure sensor 102 includes an optical sensor 104 and a motion sensor 106. The optical sensor 104 can include one or more emitters configured to irradiate light on a patient's tissue. The optical sensor 104 may further include one or more detectors that detect the light transmitted through the tissue. The optical sensor 104 can generate a photoplethysmograph responsive to this detected light. The photoplethysmograph (often referred to herein as a "plethysmograph" or "pleth") can be a waveform that represents changes in blood volume as measured by the light irradiated at the patient's tissue site. The pleth is caused at least partly by arterial pulsation, and as such, is related to arterial blood pressure. Thus, as will be described in detail herein, the pleth may be used to derive blood pressure measurements noninvasively.

Multiple emitters are included in some embodiments of the optical sensor 104 and may emit light at different wavelengths, as is described in greater detail below with respect to FIG. 16. In addition to being used to derive a pleth, the optical sensor 104 can be used to obtain other physiological parameters, such as any of the blood constituents described above. The optical sensor 104 may be a transmittance sensor or a reflectance sensor.

The motion sensor 106 can be an accelerometer, gyroscope, gradiometer, or any other motion sensing device. The motion detected by the motion sensor 106 can be velocity, position (e.g., displacement), acceleration, or any combination of the above. The motion may be provided as magnitude and/or direction values. For example, acceleration values may be represented with magnitude and direction. The motion sensor 106 can detect a patient's motion in one axis or in multiple axes. A three-axis accelerometer, for instance, may output acceleration magnitudes in x, y, and z coordinates (e.g., relative to a position of the accelerometer).

The noninvasive blood pressure sensor 102 may be placed on a measurement site of a patient, such as a patient's finger, ear, foot, or anywhere where pulsating blood can be detected. Mechanical acceleration or other motion of the measurement site can cause deformation in the pleth. This deformation can be a function, at least in part, of arterial and/or venous blood pressure, as well as the intensity and/or direction of the mechanical acceleration of the measurement site. Advantageously, in certain embodiments, this deformation in the pleth may be measured and used to estimate arterial and/or venous blood pressure noninvasively.

Figure 2:
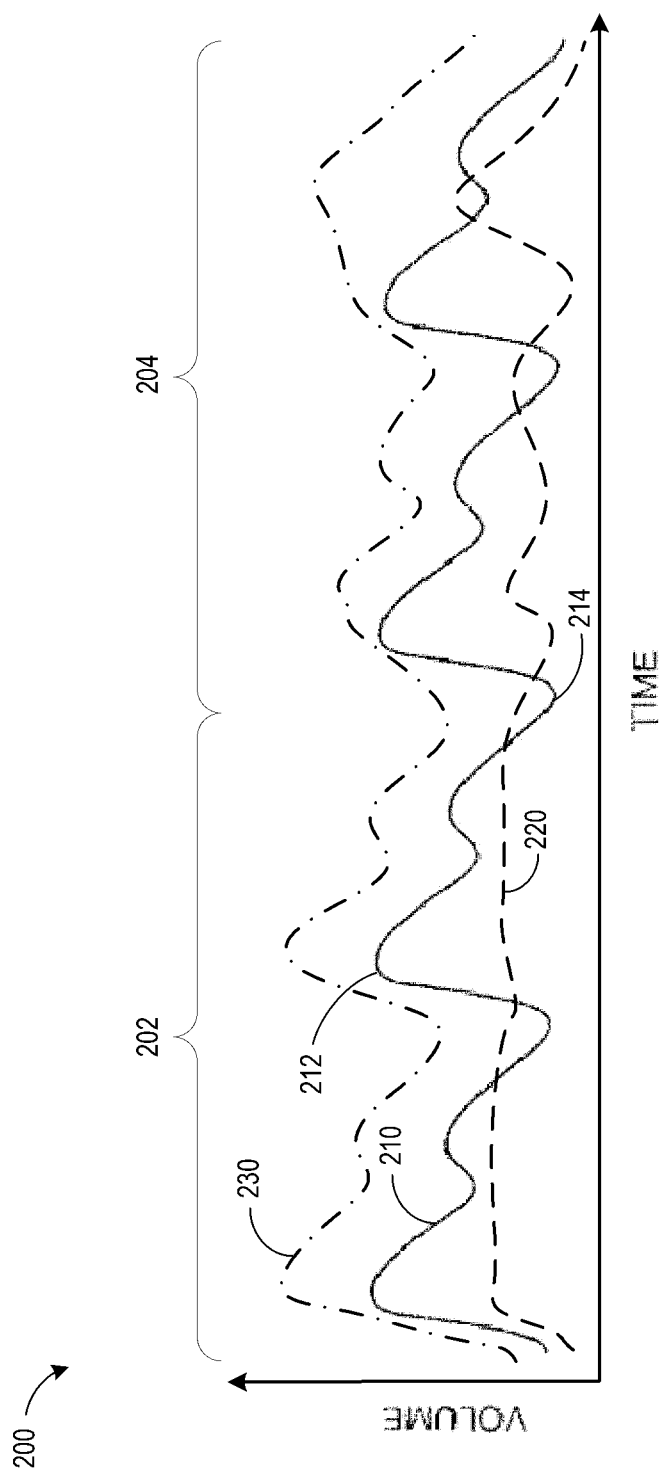
FIG. 2 illustrates a plot of example plethysmograph and motion waveforms.

To illustrate motion-induced deformation of the pleth, FIG. 2 depicts a plot 200 of an example pleth waveform 210 and an example motion waveform 220. The pleth waveform 210 may be produced by the optical sensor 104 described above, while the motion waveform 220 may be produced by the motion sensor 106. For ease of illustration, the motion waveform 220 is depicted from a single axis. The example motion pleth and motion waveforms 210, 220 shown are also simplified for illustrative purposes.

As a measurement site is placed into motion, the motion at the measurement site can deform the pleth 210. Deformation of the pleth 210 may result in the pleth 210 having higher peaks in some places and lower peaks in others, or higher or lower troughs. An example deformed pleth waveform 230 is also shown (not drawn to scale). The deformed pleth 230 reflects changes to the pleth 210 due to the motion 220. For a first time period 202, the motion 220 is relatively constant and, in this example, in phase and the same direction as the pleth. The deformed pleth 230 is therefore constructively deformed to be relatively similar to but larger in magnitude than the original pleth 210. For a second time period 204, the motion 220 varies, resulting in some destructive deformation of the pleth 210.

The amount of deformation in the pleth due to the motion can depend on a patient's blood pressure. At higher blood pressures, the arteries or veins are under greater tension than at lower blood pressures. At lower blood pressures, the vessels become more compliant or elastic than at higher blood pressures. Thus, the lower the blood pressure, the greater can be the possible amount of deformation in the pleth due to motion. Conversely, the higher the blood pressure, the lower the possible amount of deformation in the pleth due to motion. As the acceleration increases, the amount of deformation increases. However, the amount of deformation may increase at a slower rate at higher blood pressures than at lower blood pressures.

Thus, the component of the pleth due to motion can be indicative of blood pressure. Deriving this component of the pleth due to motion can allow a processor to calculate blood pressure. Algorithms for deriving this motion component are described in detail below. This component may also be monitored directly without calculating blood pressure, so as to determine whether changes in blood pressure have likely occurred. If changes have likely occurred, an occlusive cuff can be inflated to take a gold-standard blood pressure measurement. Such cuff-measurement embodiments are described in greater detail below with respect to FIG. 15.

It should be noted that the pleth 210 includes peaks 212 and troughs 214. The peaks 212 reflect systolic action of the heart, while the troughs 214 reflect diastolic action of the heart. Blood pressure measurements can be correlated in time with the peaks 212 and troughs 214 of the pleth so as to obtain systolic and diastolic blood pressure, respectively. For instance, a second optical sensor may be placed at a second measurement site that is not in motion, while a first optical sensor at a first measurement site is in motion. The motion component of the pleth derived from the first optical sensor can be correlated in time with the peaks and troughs of the second sensor's pleth, which may not be disturbed by motion. The systolic and diastolic pressures can therefore be obtained. In other embodiments, systolic and diastolic pressures are obtained with a single sensor. Alternatively, mean blood pressure is obtained instead of or in addition to systolic and diastolic pressures. For convenience, the remainder of this application will generically refer to obtaining blood pressure measurements without specifying whether the measurements are systolic, diastolic, or mean blood pressure. However, it should be understood that any of these or other types of blood pressure measurements may be obtained by the systems and algorithms described herein.

Referring again to FIG. 1, also shown is a parameter calculator 110 in communication with the noninvasive blood pressure sensor 102. The parameter calculator 110 can receive optical sensor data provided by the optical sensor 104 and the motion data provided by the motion sensor 106. From this data, the parameter calculator 110 can derive the motion component of a pleth and may use this motion component to calculate blood pressure and/or to trigger a blood pressure cuff.

The parameter calculator 110 can include hardware, such as one or more processors or other circuitry, software, and/or firmware for calculating a physiological parameter such as blood pressure. The parameter calculator 110 can output parameter data 113 indicative of calculated parameters, including blood pressure, for presentation to a user. The parameter data 113 can be displayed on a display device 120. In another embodiment, the parameter calculator 110 provides parameter values as an output 112 to another device, for example, a device providing an audible response, or over a network to a remote device. For example, a remote device might be a computer located at a nurses' station or a clinician's handheld device.

The parameter calculator 110 can also calculate trend data reflecting trend information for the parameter data 113. The parameter calculator 110 can also synthesize or scale waveform data. In addition to outputting the parameter data 113, the parameter calculator 110 can output trend data 114, synthesized, scaled, or actual waveforms 115, calibration data 116, and alarms 117. The parameter calculator 110 can provide the outputs 113, 114, 115, 116 to the display 120, to a separate patient monitoring device, or to another device configured to receive physiological parameter information (e.g., to a clinician's device over a network).

In an embodiment, the parameter calculator 110 is implemented in a single monitoring device. In an embodiment, the features of the parameter calculator 110 are distributed among separate devices. In an embodiment, the parameter calculator 110 includes a processor, processor board, or an Original Equipment Manufacture (OEM) board. In an embodiment, the parameter calculator 110 is portable. Data communicated between the various components of the parameter calculation system 100 can be communicated through cables or wirelessly. Other inputs and/or outputs can be included with the system.

III. Example Blood Pressure Measurement Processes

Figure 3:
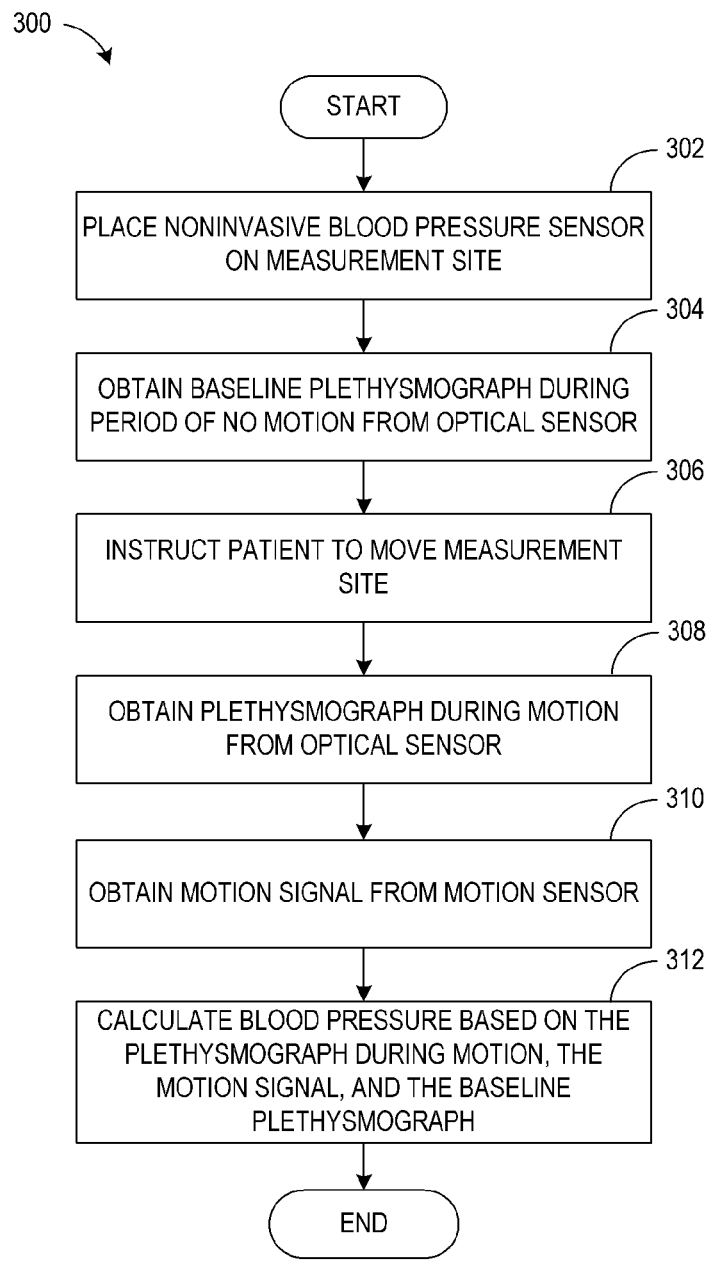
FIG. 3 illustrates an embodiment of a spot-check blood pressure measurement process.
Figure 4:
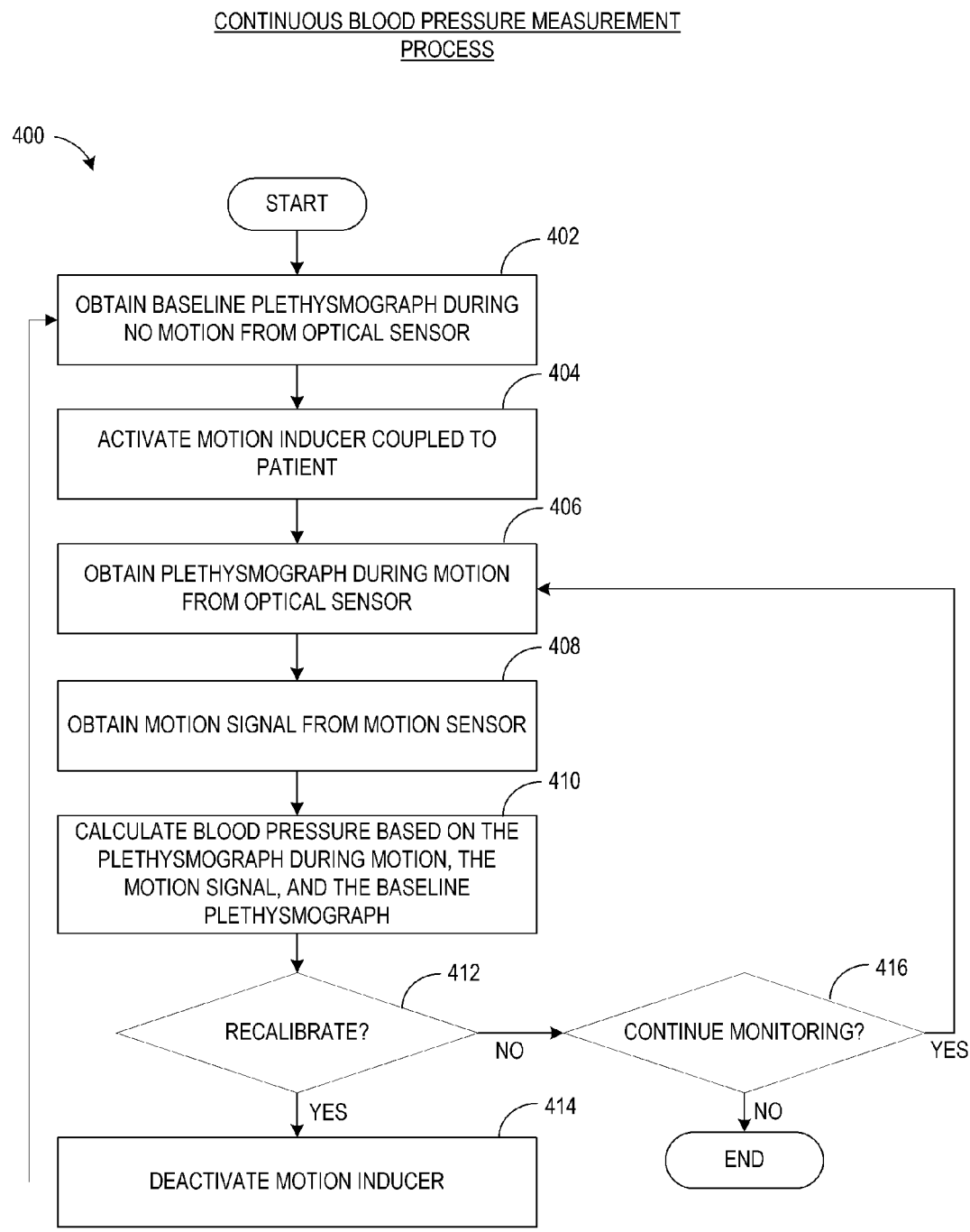
FIG. 4 illustrates an embodiment of a continuous blood pressure measurement process.

FIGS. 3 and 4 illustrate embodiments of processes for obtaining blood pressure. In particular, FIG. 3 illustrates an embodiment of a spot-check blood pressure measurement process 300, while FIG. 4 illustrates an embodiment of a continuous blood pressure measurement process 400. The spot-check measurement process 300 may be used in a home healthcare setting, a doctor's office, or at a hospital to obtain a single instance of a blood pressure measurement at a time. The continuous measurement process 400 may also be used in these settings but for continuous (or periodic) monitoring of patient blood pressure over time. The processes 300, 400 will be described in the context of the parameter calculation system 100. However, these processes 300, 400 can be implemented by any of the systems and algorithms described herein.

Referring specifically to FIG. 3, the spot-check measurement process 300 begins at block 302, where a clinician (such as nurse or doctor) places a noninvasive blood pressure sensor on a patient's measurement site. At block 304, the parameter calculator 110 obtains a baseline pleth during a period of little or no motion from the optical sensor 104. The clinician may, for instance, instruct the patient not to move for a brief period of time, such as a few seconds. During this time, the parameter calculator 110 can obtain the baseline pleth measurement.

At block 306, the clinician instructs the patient to move the measurement site. If the blood pressure sensor 102 is attached to the patient's finger, for example, the clinician might instruct the patient to gently shake or otherwise move his or her hand. In one embodiment, random motion of the measurement site may enable the signal processing algorithms described below to achieve accurate results in the fastest time. However, periodic motion (such as tapping a finger at a certain frequency) may also be processed to obtain accurate results in some embodiments.

The parameter calculator 110 obtains a pleth during the motion from the optical sensor 104 at block 308. This pleth, unlike the baseline pleth, may be deformed by the motion. As discussed above, the degree to which the pleth is deformed can be indicative of blood pressure. At the same or substantially the same time, the parameter calculator 110 obtains a motion signal from the motion sensor 106. For example, the parameter calculator 110 can obtain acceleration data from an accelerometer. The parameter calculator 110 can calculate one or more blood pressure measurements based on the pleth during motion, the motion signal, and the baseline pleth.

Although the motion component of the deformed pleth may be indicative of blood pressure, the parameter calculator 110 can use the baseline pleth and the motion signal to normalize the motion component with respect to acceleration and perfusion. Normalization can allow deformations in the pleth to be compared across different acceleration and perfusion conditions. Normalization is discussed in greater detail below (see, e.g., FIG. 9).

Referring specifically to FIG. 4, in the continuous measurement process 400, motion is obtained with a motion inducer coupled with the measurement site, rather than by instructing the patient to move the measurement site. The motion inducer may activate periodically or continuously, allowing periodic and/or continuous blood pressure measurements to be calculated.

At block 402, the parameter calculator 110 obtains a baseline pleth during no motion from the optical sensor 104 as described above. At block 404, a motion inducer coupled to the patient is activated, either automatically or with clinician or patient input. The motion inducer may be a motor, vibrator, buzzer, or the like. The motion inducer may be coupled with the patient before the initial pleth is obtained. In some implementations, the motion inducer is part of the sensor 102.

At block 406, the parameter calculator 110 obtains a pleth during motion (caused by the motion inducer) from the optical sensor 104. At the same or substantially same time, the parameter calculator 110 obtains a motion signal from a motion sensor. As described above with respect to FIG. 3, the parameter calculator 110 calculates blood pressure based on the pleth during motion, the motion signal, and the baseline pleth at block 410.

At block 412, the parameter calculator 110 determines whether to recalibrate. Recalibration can include obtaining a new baseline pleth. As a patient's baseline pleth may change over time, recalibration can increase the accuracy of blood pressure measurements over time. Thus, if recalibration is desired, the parameter calculator 110 (or clinician or patient) deactivates the motion inducer at block 414, and the process 400 loops back to block 402. Otherwise, the parameter calculator 110 determines whether to continue monitoring at block 416. If so, the process loops back to block 406, where the parameter calculator 110 obtains the pleth during motion. If the parameter calculator 110 determines that monitoring is completed, the process 400 ends.

The process 400 may be adapted in certain embodiments to use the natural motion of a patient's body at the tissue site instead of (or in addition to) a motion inducer. Patients typically move periodically. If the pleth is being obtained continuously, periods where the patient moves could be used to obtain a motion-deformed pleth, which can be used to calculate blood pressure as described above. The parameter calculator 110 can, in some embodiments, determine whether the tissue site has reached a threshold amount of movement (based on the motion sensor signal), and in response, calculate a blood pressure measurement. This form of monitoring, although referred to as continuous, may also be considered periodic monitoring. The parameter calculator 110 can also analyze the motion sensor output to determine whether the patient is moving at all. If little or no motion is detected for an extended period, the parameter calculator 110 may output an alarm for clinicians to evaluate whether the patient is in need of medical assistance.

IV. More Detailed Example Blood Pressure Measurement Calculations

Figure 5:
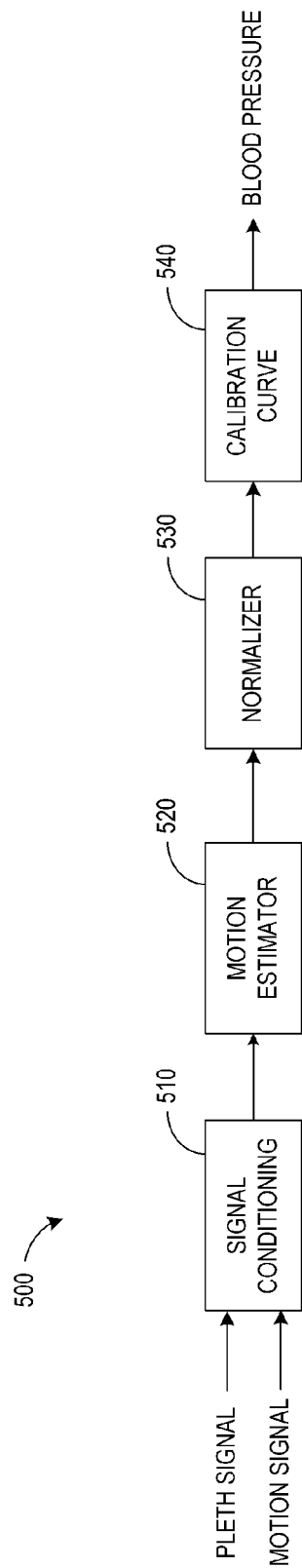
FIG. 5 illustrates an embodiment of a system for calculating blood pressure.

FIG. 5 illustrates an overview embodiment of a system 500 for calculating blood pressure. The system 500 may be implemented by the parameter calculation system 100 or by any other system described herein. Components of the system 500 may be implemented in software and/or hardware. These components include a signal conditioning block 510, a motion estimator 520, a normalizer 530, and a calibration curve block 540. More detailed aspects of the motion estimator 520, normalizer 530, and calibration curve block 540 are described in subsequent Figures.

The signal conditioning block 510 receives both pleth and motion signals. The signal conditioning block 510 can include electronic circuitry for front-end signal conditioning, which can include low-noise amplification, transimpedance amplification, analog-to-digital conversion, sampling, combinations of the same, and the like. The signal conditioning block 510 may be implemented in the parameter calculation system 100 or directly in the noninvasive blood pressure sensor 102. The output of the signal conditioning block 510 can include digital pleth and motion signals.

These signals are passed to the motion estimator 520, which can include functionality for estimating the portion of the pleth that is due to motion. Example algorithms for estimating this motion are described in detail below with respect to FIGS. 6 through 8B. The motion portion of the pleth is provided by the motion estimator 520 to the normalizer 530. As described briefly above, the normalizer 530 can use a baseline pleth and the motion signal to normalize the motion component in the pleth with respect to acceleration and perfusion. Normalization can allow deformations in the pleth to be compared across different acceleration and perfusion conditions.

Further, the normalizer 530 can normalize the motion component of a first pleth obtained from a first waveform with a motion component of a second pleth of a second waveform. More than two waveforms may also be used in the normalization process. The normalizer 530 outputs normalized motion components, ratios, or the like (see FIG. 9) to a calibration curve block 540. The calibration curve block 540 can implement a look-up table (LUT) or the like that provides blood pressure values corresponding to the outputs from the normalizer 530. The calibration curve or curves used by the block 540 can be determined experimentally and may vary based on characteristics of the patient. For example, different curves may be used for patients based on their age (e.g., neonate versus child versus adult), gender, health status, condition, comorbidity, current or past medications, and the like.

Figure 6:
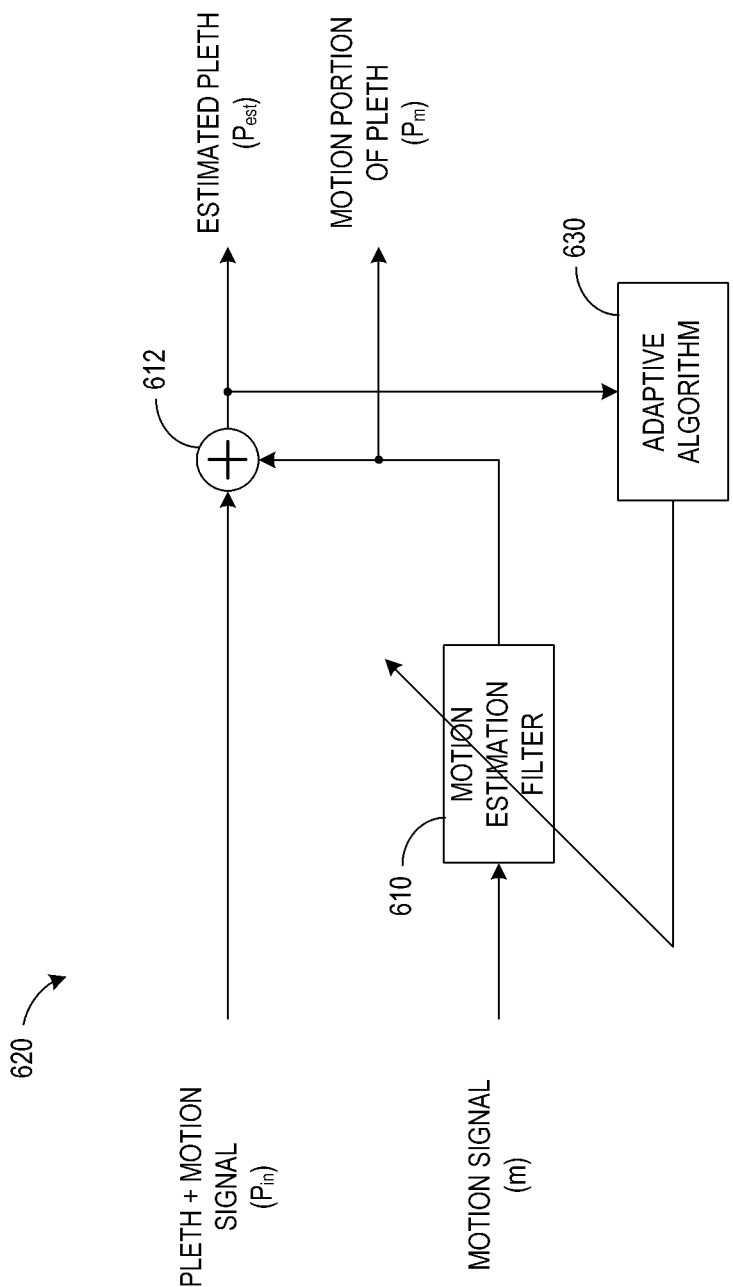
FIG. 6 illustrates an embodiment of a motion estimator.

FIG. 6 illustrates a more detailed embodiment of a motion estimator 620, which is an example implementation of the motion estimator 520. The motion estimator 620 is shown implemented as an adaptive filter in the depicted embodiment. The motion estimator 620 may be implemented by the parameter calculation system 100 or by any other system described herein.

The motion estimator 620 receives a pleth with motion signal (deformed pleth, $P_{in}$) and a motion signal (m). The motion signal is provided to a motion estimation filter 610. As shown, the motion estimation filter 610 is an adaptive filter. This adaptive filter may be a tapped delay line or the like and may be implemented as a finite impulse response (FIR) filter, an infinite impulse response (IIR) filter, or a combination of the same. One embodiment of the motion estimation filter 610 is described in detail below with respect to FIG. 7. The motion estimation filter 610 outputs an estimated motion portion of the pleth ($P_m$).

The motion portion of the pleth is combined with the pleth plus motion signal, for example, by subtracting the motion portion of the pleth from the pleth plus motion signal. This combination produces an estimated pleth signal with the motion removed, sometimes referred to herein as the clean pleth signal. This clean pleth signal is provided to an adaptive algorithm 630, which uses this signal (or other signals) to adjust weights or coefficients of the adaptive filter 610.

Any of a variety of adaptive algorithms 630 may be used. For instance, the adaptive algorithm 630 could implement one or more of the following: a Wiener filter, gradient search methods, ellipsoid search methods, a least mean squares algorithm (LMS), a least squares algorithm (such as a pseudoinverse), a recursive least squares (RLS) algorithm, a Kalman filter, a joint process estimator, an adaptive joint process estimator, a least-squares lattice joint process estimator, a least-squares lattice predictor, a correlation canceller, a linear predictor, linear programming, an estimator or algorithm using an $L_1$, $L_2$, or $L_\infty$ norm, optimized or frequency domain implementations of any of the above, combinations of the same, and the like.

As shown, the motion estimator 520 acts like an adaptive noise canceller or adaptive noise filter, removing the noise, or the motion portion of the pleth to produce the clean pleth signal $P_{est}$. However, this motion noise was intentionally introduced by the patient or a motion inducer (see FIGS. 3 and 4). Unlike a typical adaptive noise filter, in some embodiments we are interested in obtaining the noise instead of the clean pleth signal. Counterintuitively, the noise, or the motion portion of the pleth, is therefore the signal of interest output by the motion estimator 620.

Figure 7:
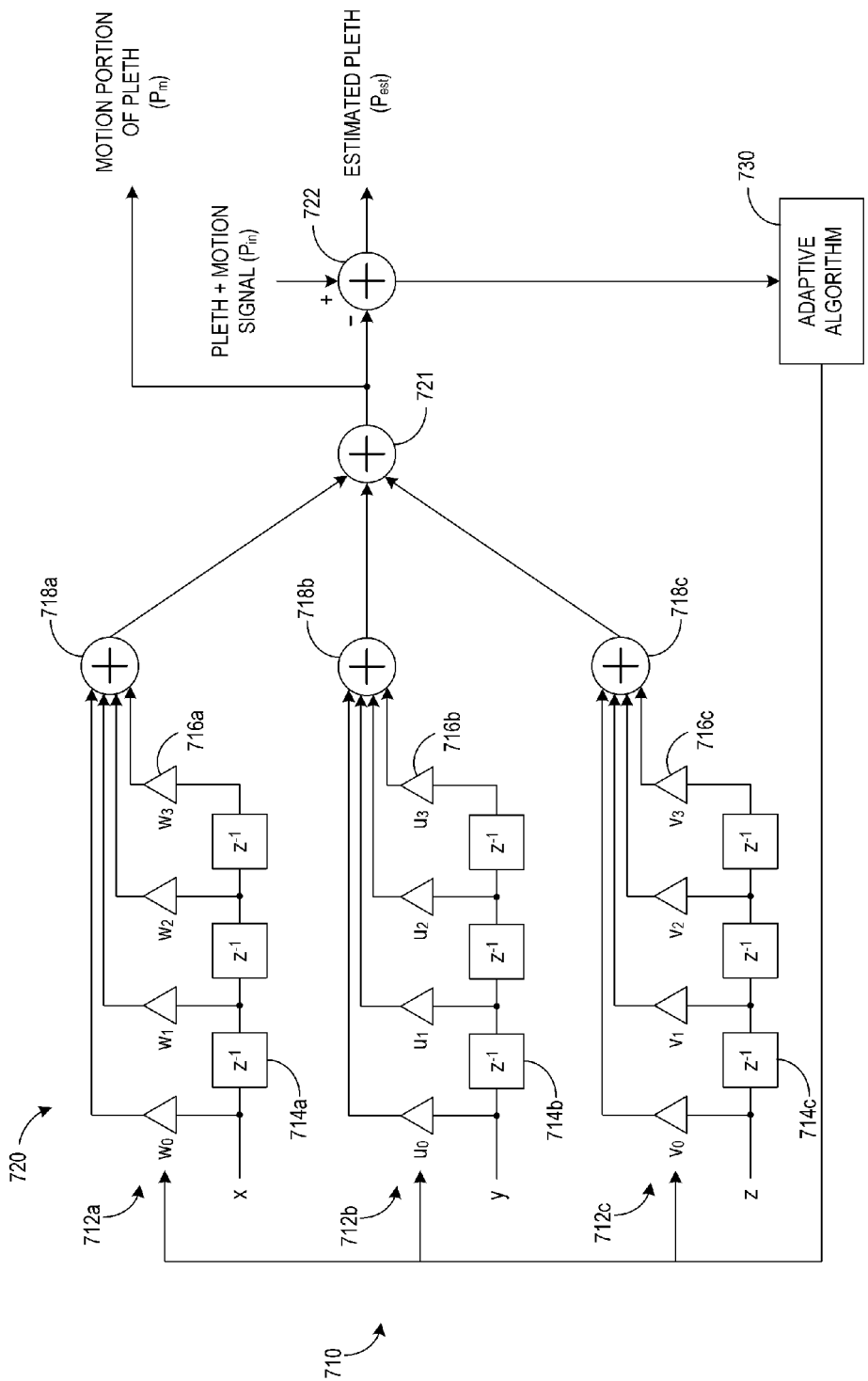
FIG. 7 illustrates a more detailed embodiment of the motion estimator of FIG. 6.

FIG. 7 illustrates a more detailed embodiment of the motion estimator 620 of FIG. 6, namely a motion estimator 720. The motion estimator 720 includes an FIR adaptive filter 710 (corresponding to the filter 610) that takes as inputs the motion signal (m) of FIG. 6. These inputs are represented by the Cartesian coordinates x, y, z in the depicted embodiment, although other coordinate systems or fewer or more coordinates can be used. Each coordinate represents a component of motion output by the motion sensor 106 of FIG. 1, such as acceleration magnitude.

The adaptive filter 710 is a vector FIR filter in the depicted embodiment, composed of three one-dimensional FIR filters 712a, 712b, 712c that combine together in some embodiments to form a single output per sample. Each one-dimensional FIR filter 712 includes delay blocks 714 and coefficients or taps 716. The number of delay blocks 714 and taps 716 shown are merely illustrative examples, and other numbers of delay blocks 714 and taps 716 may be used in some implementations. The outputs of the taps 716 are combined by a combiner 718. A combiner 718a, 718b, 718c is shown for each one-dimensional FIR filter 712. The outputs of each of the combiners 718 are combined by another combiner 721 to produce an output of the adaptive filter 710.

Each one-dimensional FIR filter 712 can be implemented as a tapped-delay line. The values of the taps 716 in each tapped-delay line may be adjusted to change the phase of the respective motion signal component (x, y, or z). This adjustment in phase can cause the motion signal to be correlated in time with the pleth plus motion signal, so that these two signals can be compared at the same instants in time. Without this phase adjustment, the motion and pleth signals may be out of phase due to dynamic effects, lack of perfect time synchronization between sensors, and the like. This correlation in time is illustrated graphically in FIGS. 8A and 8B, where a pleth signal 810 and motion signal 820 as acquired by the sensor 102 are first out-of-phase in a plot 800A of FIG. 8A, and then subsequently correlated or in-phase in a plot 800B of FIG. 8B.

To illustrate the tapped-delay concept, if the tap $w_1$ in FIG. 7 is given a weight of 1, and the remaining taps $w_i$ are given a weight of 0, the x coordinate samples will be delayed one sample. If instead the tap $w_2$ were given a value of 1 and the other taps 0, the x coordinate samples would be delayed by two samples, and so on. The phase of the motion signal may therefore be delayed or phase-shifted to correlate in time with the pleth plus motion signal. The values of the taps 716 may be selected so as to provide a smooth delay, and may or may not actually be 0 or 1. An adaptive algorithm 730 (corresponding to the adaptive algorithm 630 of FIG. 6) can adjust the taps 716 programmatically and continuously to track the motion signal with the pleth. As a result, the output of the combiner 721 can be subtracted from or otherwise combined with the pleth plus motion signal to produce the estimated pleth signal, which is an error signal supplied to the adaptive algorithm 730. The output of the combiner 721 is the motion portion of the pleth, which can be the signal of interest in determining blood pressure.

As described above with respect to FIG. 6, the adaptive algorithm 730 may be implemented in a variety of ways. For example, the adaptive algorithm 730 can use a least squares algorithm based on a block of samples, such as the following:

$$\begin{bmatrix} x_n & \cdots & x_{n-i} & y_n & \cdots & y_{n-i} & z_n & \cdots & z_{n-i} \\ x_{n+1} & \cdots & x_{n-i+1} & y_{n+1} & \cdots & y_{n-i+1} & z_{n+1} & \cdots & z_{n-i+1} \\ & & & & \vdots & & & & \end{bmatrix} \vec{w} = \vec{P}_m \quad (1)$$

$$A$$

where the matrix A includes motion samples x, y, z, where n represents the nth sample, i represents the number of delay blocks 714 (or taps 716), w represents a vector of the weights or taps 716 (and which may include the $w_i$, $u_i$, and $v_i$ taps 716 in FIG. 7), and $P_m$ represents a vector of pleth motion component values. Each row in the matrix A represents 3(n+i) samples. For example, if the number of delay blocks 714 is 4, there are 5 "x" samples, 5 "y" samples, and 5 "z" samples per row, for a total of 15 samples per row. The samples in the next row are shifted over by one sample in this example. The matrix can include any number of rows and samples. However, since a larger number of rows than columns can result in a singular matrix "A" that is not invertible, solving for the weights in equation 1 can be performed using a least-squares estimation technique. The least-squares estimation technique can employ the pseudo-inverse as follows:

$$\vec{w} = (A^T A)^{-1} A^T \vec{P}_m \quad (2)$$

where the matrix $(A^T A)^{-1} A^T$ is the Moore-Penrose pseudo-inverse.

The sample values in the motion portion of the pleth ($P_m$) could be input into the calibration curve lookup table (540) to derive blood pressure values. However, different magnitudes of acceleration or motion could result in different magnitudes of the motion portion of the pleth, even though the blood pressure stays constant. Similarly, different levels of perfusion can result in different magnitudes of the motion component of the pleth, even when the blood pressure stays the same. Moreover, pleth signals obtained from different wavelengths can have different magnitudes than each other and may be affected differently by motion. Thus, instead of directly looking up the motion portion of the pleth in a calibration curve LUT, in some embodiments, the motion portion of the pleth may first be normalized to account for motion, perfusion, and/or wavelength differences.

Figure 9:
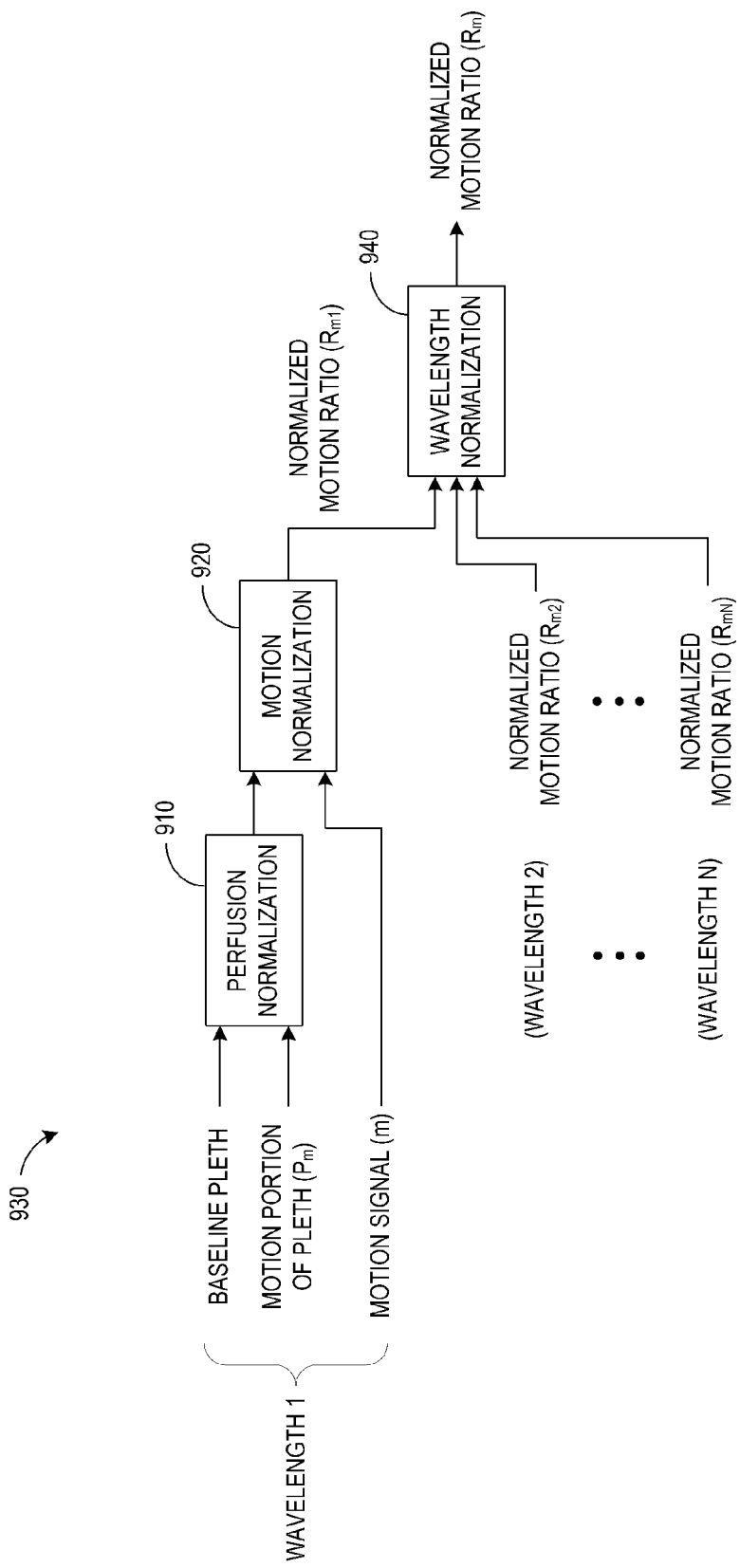
FIG. 9 illustrates an embodiment of a normalizer.

FIG. 9 illustrates an embodiment of a normalizer 930 that can be used to normalize the motion component of the pleth. The normalizer 930 includes a perfusion normalization component 910, a motion normalization component 920, and a wavelength normalization component 940. Any subset of the normalization components 910, 920, 940 may be used in any given implementation. For convenience, normalization for a single wavelength ("wavelength 1") is shown in detail. The normalization techniques applied to this wavelength may also be extended to any number of wavelengths (N wavelengths). However, in some embodiments, a single wavelength is used instead of multiple wavelengths, so that wavelength normalization is not employed. The normalizer 930 may be implemented by the parameter calculation system 100 or by any other of the systems described herein.

Inputs to the normalizer 930 include a baseline pleth, motion portion of the pleth, and motion signal for each wavelength. The perfusion normalization component 910 receives the baseline pleth and the motion portion of the pleth. The perfusion normalization component 910 normalizes the motion component of the pleth based on the baseline pleth, to thereby reduce or cancel out the effects of perfusion on the magnitude of the motion component of the pleth. One way to normalize for perfusion is to obtain a first statistical measure of a component of baseline pleth samples and a second statistical measure of a component of motion portion of the pleth samples. A ratio can then be constructed of the two statistical measures, for example, by dividing the second statistical measure by the first statistical measure. One example statistical measure that may be used, among many others, is the root-mean square (RMS). Equation 3 illustrates one possible perfusion normalization:

$$M_{norm} = \frac{\text{RMS}(P_m)}{\text{RMS}(P_{baseline})} \quad (3)$$

where $M_{norm}$ represents a normalized motion ratio, $P_m$ represents a series of pleth motion component values, and $P_{baseline}$ represents a series of baseline pleth values. In equation 3, as the pleth gets bigger due to higher perfusion or smaller due to lower perfusion, the value of $M_{norm}$ stays the same or about the same for the same value of $P_m$.

The output of the perfusion normalization component 910 is provided to the motion normalization component 920. As above, a statistical measure of the motion may be used to normalize based on motion. For example, the following equation may be constructed:

$$R_{m1} = \frac{M_{norm}}{\text{RMS}(x, y, z)} \quad (4)$$

where the x, y, z coordinates of an example motion signal m are used, and where $R_{m1}$ represents a normalized motion ratio for wavelength 1. In another embodiment, perfusion normalization is not used. Thus, the normalized motion ratio may instead be:

$$R_{m1} = \frac{\text{RMS}(P_m)}{\text{RMS}(x, y, z)} \quad (5)$$

In either equation 4 or 5, as the motion increases or decreases, the value of $R_{m1}$ stays the same or about the same for the same value of $P_m$.

The wavelength normalization component 940 may receive normalized motion ratios $R_{mn}$, for N waveforms. The wavelength normalization component 940 may take ratios of these ratios to produce an overall normalized motion ratio $R_m$. For example, if there are two wavelengths, the wavelength normalization component 940 can compute $R_{m1}/R_{m2}$ to produce $R_m$. As with motion and perfusion, it is possible for the normalizer 930 to normalize only for wavelength. Thus, for example, the normalizer 930 can normalize $P_{m1}/P_{m2}$ to produce $R_m$.

Referring again to FIG. 5, the normalizer 530/930 can provide the normalized motion ratio $R_m$ to the calibration curve lookup table 540, which can lookup a corresponding blood pressure value for a given value of $R_m$. Although not shown, the $R_m$ values or the blood pressure values (or $P_m$ or other values described herein) may be smoothed or otherwise averaged to reduce variability in the blood pressure measurements.

Up to this point, the framework of FIG. 5 has operated under the assumption that samples in the motion portion of the pleth and blood pressure values share a linear relationship. This may not always be the case. Instead, some aspects of the motion/blood pressure relationship may be linear, while others may be nonlinear. More generally, the blood pressure can be some function of the motion portion of the pleth or of the motion signal itself. This function may itself be a combination of functions. Further, this function may differ for different patients based on their characteristics, conditions, and so forth. Thus, a refinement to the blood pressure calculation framework of FIG. 5 can be to incorporate one or more functions of the motion portion of the pleth or the motion signal itself into the blood pressure calculation.

Figure 10:
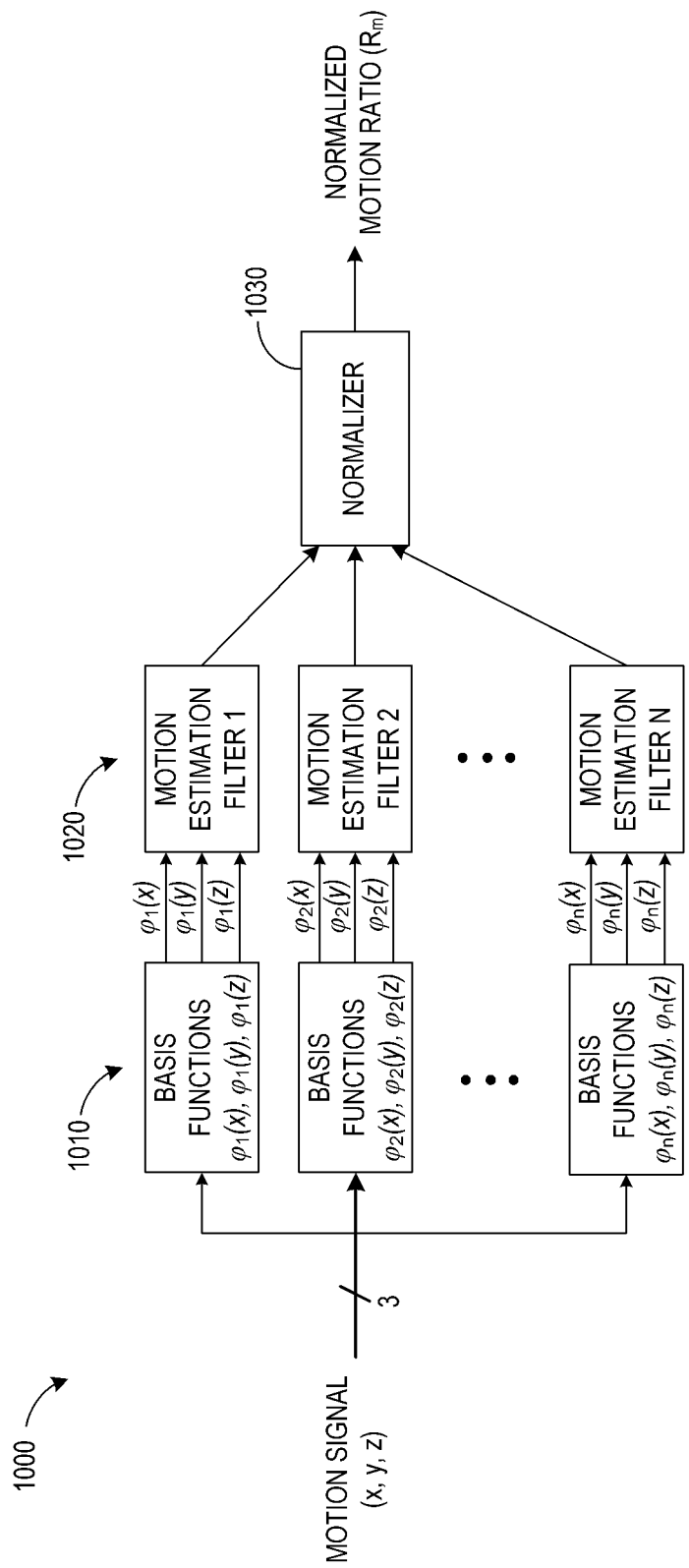
FIGS. 10 and 11 illustrate embodiments of algorithms for calculating normalized motion ratios.
Figure 11:
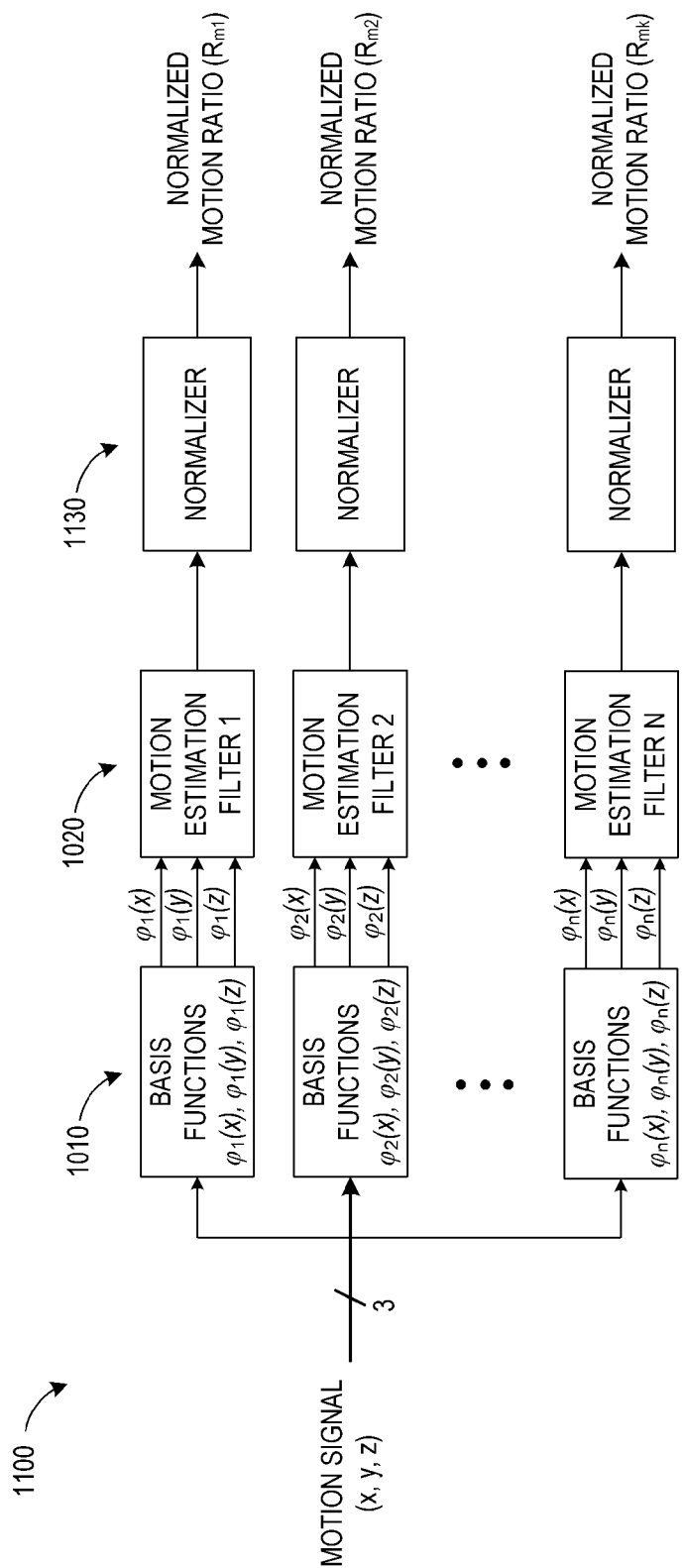

Doing so may be accomplished in many ways. However, as an example illustration, FIGS. 10 and 11 depict embodiments of algorithms 1000, 1100 that use basis functions as a portion of the blood pressure computation. Referring to FIG. 10, a motion signal (x, y, z) is provided to one or more basis functions 1010 (multiple basis functions 1010 are shown). The basis functions 1010 can be blending functions or the like. For example, the basis functions can be polynomial functions (such as x, $x^2$, $(x_1+x_2)/2$, combinations thereof, and the like), transcendental functions (e.g., exp(x), ln(x)), trigonometric functions, Fourier basis functions, wavelet basis functions, radial basis functions, combinations of the same, and the like. In the depicted embodiment, a basis function is applied to each coordinate motion input, or in some cases, fewer than all coordinate inputs. The outputs of the basis functions are provided to motion estimation filters 1020. These motion estimation filters can implement the features of the motion estimation filters 520, 620, 720, except with the basis function inputs instead of the motion signal inputs themselves.

Multiple sets of basis functions 1010 are used in some embodiments to provide several different types of outputs to the motion estimation filters. For any given patient or monitoring scenario, one set of basis functions may result in more accurate blood pressure measurements than another. Although not shown, the outputs of the basis functions may be weighted. These weights may be adapted based on an occlusive cuff measurement (see FIG. 14). The outputs of the motion estimation filters are provided to a normalizer 1030, which can implement the features of the normalizers 530, 930 to produce a single normalized motion ratio. Alternatively, as shown in FIG. 11, a normalizer 1130 can be provided as the output of each motion estimation filter so as to produce multiple normalized motion ratios. Each of these ratios can be used to calculate blood pressure values.

To save computational complexity and processing resources, the position of the basis functions 1010 and the motion estimation filters 1020 may be reversed. Thus, the motion signal may be instead provided to the motion estimation filters 1020, and the outputs thereof may be provided to the basis functions 1010. The basis functions 1010 may then output values to the normalizers 1030 or 1130.

Each normalized motion ratio can be supplied to the calibration curve lookup table. Simplified examples of calibration curves 1200, 1300 are illustrated in FIGS. 12 and 13. In FIG. 12, the calibration curve 1200 is linear, while in FIG. 13, the calibration curve 1300 is nonlinear. The type of calibration curve used may depend on the patient or may vary from that shown. The example calibration curves 1200, 1300 reflect that for increasing values of the normalized motion ratio, the blood pressure decreases and vice versa. More precise calibration curves than those shown can be obtained by comparing occlusive cuff measurements with normalized motion ratios output for several different patients. The particular calibration curve used can be adapted for individual patients.

For scenarios where multiple normalizers are used, such as in FIG. 11, the calibration curve LUT can output a separate blood pressure value for each normalizer. Similarly, if multiple wavelengths of light are used to obtain multiple plethysmographs, multiple blood pressure estimates may be obtained. For example, wavelength normalization in FIG. 9 may be avoided, or pairs of wavelengths may be normalized together to form ratios that are supplied to the calibration curve LUT. Many different algorithms can be used to select from or combine the multiple blood pressure estimates to produce an overall blood pressure value.

Figure 14:
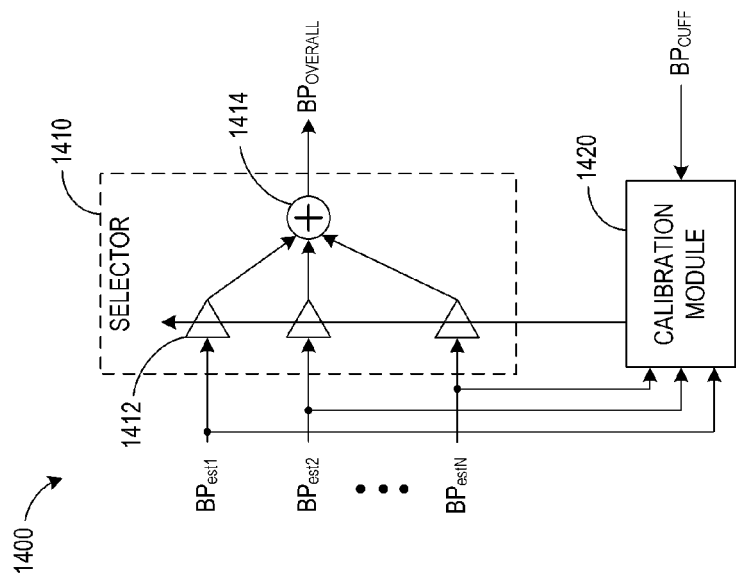
FIG. 14 illustrates an embodiment of a blood pressure calibrator.

One example of such an algorithm 1400 is illustrated in FIG. 14. In this algorithm 1400, candidate blood pressure estimates are provided to a selector 1410. The selector includes a plurality of gain blocks 1412 that have adjustable weights. The candidate blood pressure estimates are also provided to a calibration module 1420. This calibration module 1420 also receives as an input a blood pressure measurement from a blood pressure cuff ($BP_{CUFF}$). Based on differences between the cuff-based measurement and the candidate measurements, the calibration module 1420 can adjust the weights. For instance, the calibration module 1420 can apply relatively greater weight to blood pressure values that are closer to the cuff measurement and relatively lower weights to values that are farther from the cuff measurement. A combiner block 1414 can combine the outputs of the gain blocks 1412 together to produce an overall blood pressure ($BP_{OVERALL}$).

In another embodiment, the selector 1410 applies a weight of 1 to the gain block 1412 corresponding to the closest blood pressure value to the cuff measurement, effectively selecting this measurement over the others, rather than combining the measurements together. In yet another embodiment, the weights 1412 are applied to the output of the basis functions, motion estimation filter, or normalizer of FIG. 10 or 11 in addition to or instead of the blood pressure values ($BP_{est}$).

V. Occlusive Cuff Triggering

Figure 15:
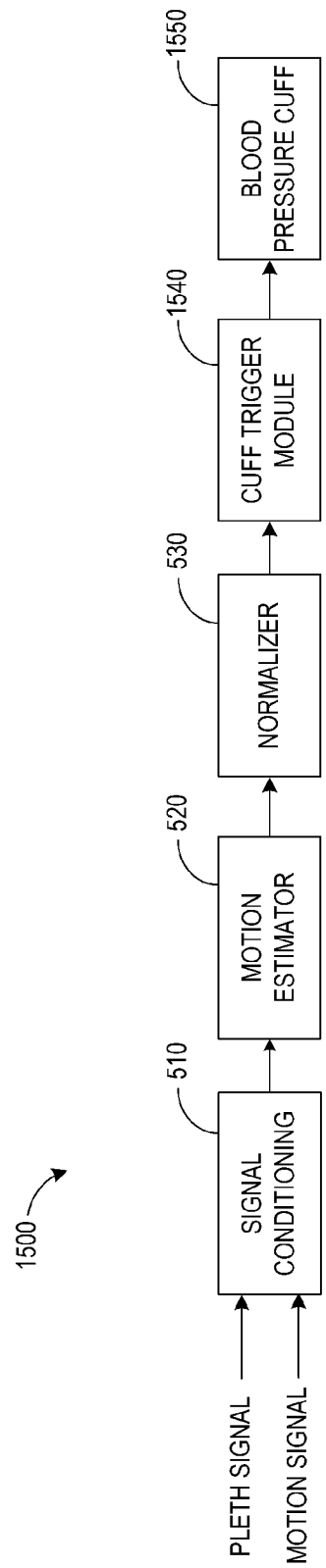
FIG. 15 illustrates an embodiment of a system for triggering an occlusive blood pressure measurement.

FIG. 15 illustrates an embodiment of a system 1500 for triggering an occlusive blood pressure measurement. The system 1500 may be implemented by the parameter calculation system 100 or by any other system described herein.

The system 1500 includes several components from the system 500 of FIG. 5, including the signal conditioning block 510, the motion estimator 520, and the normalizer 530. However, instead of computing blood pressure values, the system 1500 enables a blood pressure cuff to be triggered. To that end, the output of the normalizer 530 is provided to a cuff trigger module 1540. The cuff trigger module 1540 determines whether an output of the normalizer 530, such as a normalized motion ratio, has changed significantly over a period of time. If the output has changed significantly, then the patient's blood pressure may also have changed significantly. The cuff trigger module 1540 can therefore send a triggering signal to a blood pressure cuff 1550 to take an occlusive cuff measurement. Taking occlusive cuff measurements in response to a significant change in a noninvasive measured parameter (such as a normalized motion ratio) can reduce the frequency that occlusive cuff measurements are taken, improving patient comfort.

The cuff trigger module 1540 can use a different parameter than that output by the normalizer 530 to determine whether to trigger the blood pressure cuff. In fact, the cuff trigger module 1540 can evaluate changes in any of the measured parameters described herein, such as the motion portion of the pleth ($P_m$), any of the normalized ratios, the outputs of a basis function, or combinations of the same, including averaged or smoothed versions of the same.

VI. More Detailed Example Patient Monitoring Systems

Figure 16:
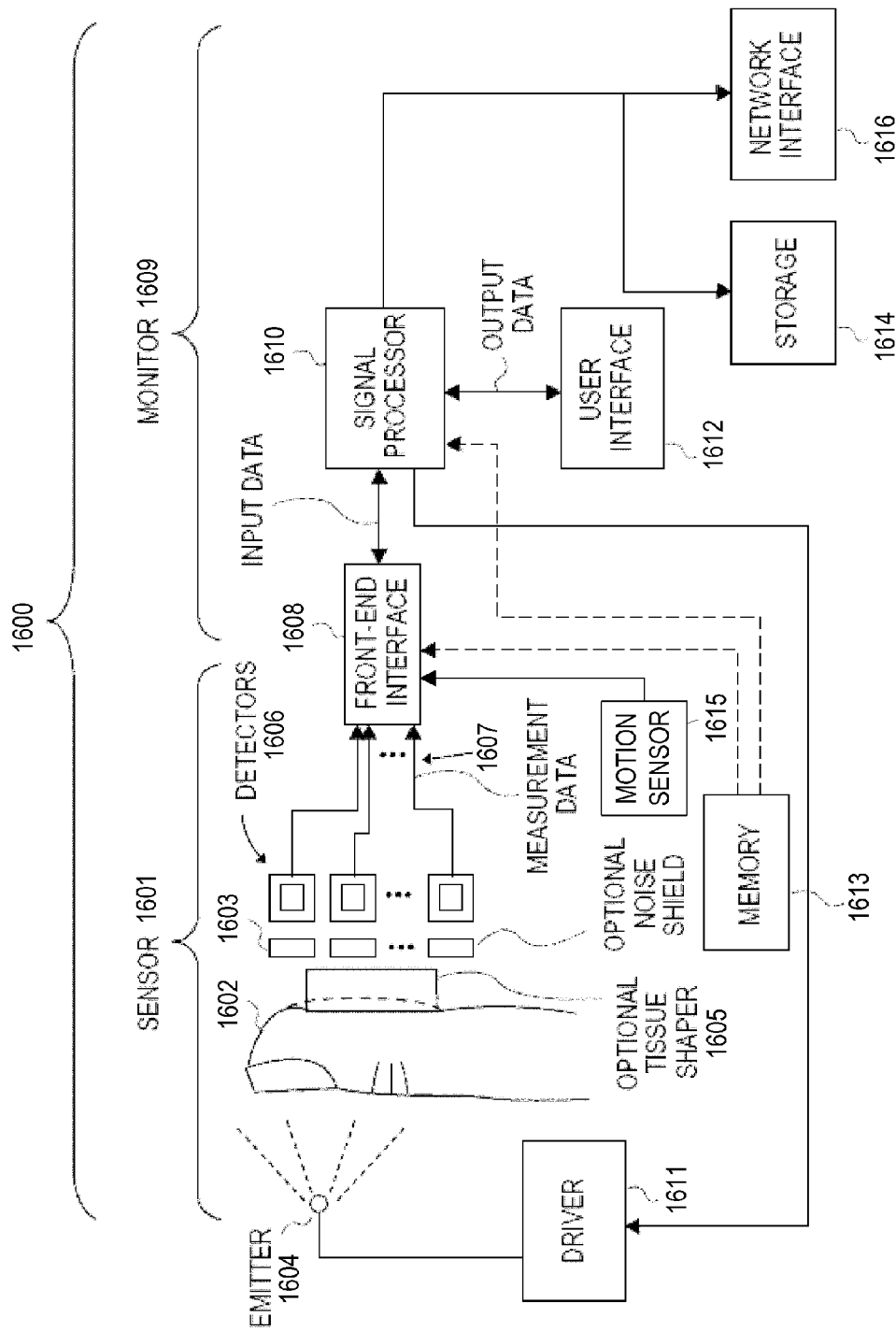
FIG. 16 illustrates an embodiment of an optical sensor system.

FIG. 16 illustrates an example of a data collection system 1600. In certain embodiments, the data collection system 1600 noninvasively measures blood pressure, as described above. In addition, the data collection system 1600 can noninvasively measure a blood analyte, such as oxygen, carbon monoxide, methemoglobin, total hemoglobin, glucose, proteins, glucose, lipids, a percentage thereof (e.g., saturation) or one or more other physiologically relevant patient characteristics. The system 1600 can also measure additional blood constituents or analytes and/or other physiological parameters useful in determining a state or trend of wellness of a patient.

The data collection system 1600 can be capable of measuring optical radiation from the measurement site. For example, in some embodiments, the data collection system 1600 can employ one or more photodiodes. In an embodiment, the photodiodes have an area from about 1 mm$^2$-5 mm$^2$ (or higher) and are capable of detecting about 100 nanoamps (nA) or less of current resulting from measured light at full scale. In addition to having its ordinary meaning, the phrase "at full scale" can mean light saturation of a photodiode amplifier (not shown). Of course, other sizes and types of photodiodes can be used in various embodiments.

The data collection system 1600 can measure a range of approximately about 2 nA to about 100 nA or more full scale. The data collection system 1600 can also include sensor front-ends that are capable of processing and amplifying current from the detector(s) at signal-to-noise ratios (SNRs) of about 100 decibels (dB) or more, such as about 120 dB in order to measure various desired analytes. The data collection system 1600 can operate with a lower SNR if less accuracy is desired for an analyte like glucose.

The data collection system 1600 can measure analyte concentrations at least in part by detecting light attenuated by a measurement site 1602. The measurement site 1602 can be any location on a patient's body, such as a finger, foot, ear lobe, or the like. For convenience, this disclosure is described primarily in the context of a finger measurement site 1602. However, the features of the embodiments disclosed herein can be used with other measurement sites 1602.

In the depicted embodiment, the system 1600 includes an optional tissue thickness adjuster or tissue shaper 1605, which can include one or more protrusions, bumps, lenses, or other suitable tissue-shaping mechanisms. In certain embodiments, the tissue shaper 1605 is a flat or substantially flat surface that can be positioned proximate the measurement site 1602 and that can apply sufficient pressure to cause the tissue of the measurement site 1602 to be flat or substantially flat. In other embodiments, the tissue shaper 1605 is a convex or substantially convex surface with respect to the measurement site 1602. Many other configurations of the tissue shaper 1605 are possible. Advantageously, in certain embodiments, the tissue shaper 1605 reduces thickness of the measurement site 1602 while preventing or reducing occlusion at the measurement site 1602. Reducing thickness of the site can advantageously reduce the amount of attenuation of the light because there is less tissue through which the light must travel. Shaping the tissue into a convex (or alternatively concave) surface can also provide more surface area from which light can be detected.

The embodiment of the data collection system 1600 shown also includes an optional noise shield 1603. In an embodiment, the noise shield 1603 can be advantageously adapted to reduce electromagnetic noise while increasing the transmittance of light from the measurement site 1602 to one or more detectors 1606 (described below). For example, the noise shield 1603 can advantageously include one or more layers of conductive coated glass or a metal grid electrically communicating with one or more other shields of the sensor 1601 or electrically grounded. In an embodiment where the noise shield 1603 includes conductive coated glass, the coating can advantageously include indium tin oxide. In an embodiment, the indium tin oxide includes a surface resistivity ranging from approximately 30 ohms per square inch to about 500 ohms per square inch. In an embodiment, the resistivity is approximately 30, 200, or 500 ohms per square inch. Other resistivities can also be used which are less than about 30 ohms or more than about 500 ohms. Other conductive materials that are transparent or substantially transparent to light can be used instead.

In some embodiments, the measurement site 1602 is located somewhere along a non-dominant arm or a non-dominant hand, e.g., a right-handed person's left arm or left hand. In some patients, the non-dominant arm or hand can have less musculature and higher fat content, which can result in less water content in that tissue of the patient. Tissue having less water content can provide less interference with the particular wavelengths that are absorbed in a useful manner by blood analytes like glucose. Accordingly, in some embodiments, the data collection system 1600 can be used on a person's non-dominant hand or arm.

The data collection system 1600 can include a sensor 1601 (or multiple sensors) that is coupled to a processing device or physiological monitor 1609. In an embodiment, the sensor 1601 and the monitor 1609 are integrated together into a single unit. In another embodiment, the sensor 1601 and the monitor 1609 are separate from each other and communicate one with another in any suitable manner, such as via a wired or wireless connection. The sensor 1601 and monitor 1609 can be attachable and detachable from each other for the convenience of the user or caregiver, for ease of storage, sterility issues, or the like. The sensor 1601 and the monitor 1609 will now be further described.

In the depicted embodiment shown in FIG. 16, the sensor 1601 includes an emitter 1604, an optional tissue shaper 1605, a set of detectors 1606, and a front-end interface 1608. The emitter 1604 can serve as the source of optical radiation transmitted towards measurement site 1602. As will be described in further detail below, the emitter 1604 can include one or more sources of optical radiation, such as LEDs, laser diodes, incandescent bulbs with appropriate frequency-selective filters, combinations of the same, or the like. In an embodiment, the emitter 1604 includes sets of optical sources that are capable of emitting visible and near-infrared optical radiation.

In some embodiments, the emitter 1604 is used as a point optical source, and thus, the one or more optical sources of the emitter 1604 can be located within a close distance to each other, such as within about a 2 mm to about 4 mm. The emitters 1604 can be arranged in an array, such as is described in U.S. Publication No. 2006/0211924, filed Sep. 21, 2006, titled "Multiple Wavelength Sensor Emitters," the disclosure of which is hereby incorporated by reference in its entirety. In particular, the emitters 1604 can be arranged at least in part as described in paragraphs [0061] through [0068] of the aforementioned publication, which paragraphs are hereby incorporated specifically by reference. Other relative spatial relationships can be used to arrange the emitters 1604.

For analytes like glucose, currently available non-invasive techniques often attempt to employ light near the water absorbance minima at or about 1600 nm. Typically, these devices and methods employ a single wavelength or single band of wavelengths at or about 1600 nm. However, to date, these techniques have been unable to adequately consistently measure analytes like glucose based on spectroscopy.

In contrast, the emitter 1604 of the data collection system 1600 can emit, in certain embodiments, combinations of optical radiation in various bands of interest. For example, in some embodiments, for analytes like glucose, the emitter 1604 can emit optical radiation at three (3) or more wavelengths between about 1600 nm to about 1700 nm. In particular, the emitter 1604 can emit optical radiation at or about 1610 nm, about 1640 nm, and about 1665 nm. In some circumstances, the use of three wavelengths within about 1600 nm to about 1700 nm enable sufficient SNRs of about 100 dB, which can result in a measurement accuracy of about 20 mg/dL or better for analytes like glucose.

In other embodiments, the emitter 1604 can use two (2) wavelengths within about 1600 nm to about 1700 nm to advantageously enable SNRs of about 85 dB, which can result in a measurement accuracy of about 25-30 mg/dL or better for analytes like glucose. Furthermore, in some embodiments, the emitter 1604 can emit light at wavelengths above about 1670 nm. Measurements at these wavelengths can be advantageously used to compensate or confirm the contribution of protein, water, and other non-hemoglobin species exhibited in measurements for analytes like glucose conducted between about 1600 nm and about 1700 nm. Of course, other wavelengths and combinations of wavelengths can be used to measure analytes and/or to distinguish other types of tissue, fluids, tissue properties, fluid properties, combinations of the same or the like.

For example, the emitter 1604 can emit optical radiation across other spectra for other analytes. In particular, the emitter 1604 can employ light wavelengths to measure various blood analytes or percentages (e.g., saturation) thereof. For example, in one embodiment, the emitter 1604 can emit optical radiation in the form of pulses at wavelengths of about 905 nm, about 1050 nm, about 1200 nm, about 1300 nm, about 1330 nm, about 1610 nm, about 1640 nm, and/or about 1665 nm. In another embodiment, the emitter 1604 can emit optical radiation ranging from about 860 nm to about 950 nm, about 950 nm to about 1100 nm, about 1100 nm to about 1270 nm, about 1250 nm to about 1350 nm, about 1300 nm to about 1360 nm, and/or about 1590 nm to about 1700 nm. Of course, the emitter 1604 can transmit any of a variety of wavelengths of visible or near-infrared optical radiation.

Due to the different responses of analytes to the different wavelengths, certain embodiments of the data collection system 1600 can advantageously use the measurements at these different wavelengths to improve the accuracy of measurements. For example, the measurements of water from visible and infrared light can be used to compensate for water absorbance that is exhibited in the near-infrared wavelengths.

As briefly described above, the emitter 1604 can include sets of light-emitting diodes (LEDs) as its optical source. The emitter 1604 can use one or more top-emitting LEDs. In particular, in some embodiments, the emitter 1604 can include top-emitting LEDs emitting light at about 850 nm to 1350 nm.

The emitter 1604 can also use super luminescent LEDs (SLEDs) or side-emitting LEDs. In some embodiments, the emitter 1604 can employ SLEDs or side-emitting LEDs to emit optical radiation at about 1600 nm to about 1800 nm. Emitter 1604 can use SLEDs or side-emitting LEDs to transmit near infrared optical radiation because these types of sources can transmit at high power or relatively high power, e.g., about 40 mW to about 100 mW. This higher power capability can be useful to compensate or overcome the greater attenuation of these wavelengths of light in tissue and water. For example, the higher power emission can effectively compensate and/or normalize the absorption signal for light in the mentioned wavelengths to be similar in amplitude and/or effect as other wavelengths that can be detected by one or more photodetectors after absorption. However, certain the embodiments do not necessarily require the use of high power optical sources. For example, some embodiments may be configured to measure analytes, such as total hemoglobin (tHb), oxygen saturation ($SpO_2$), carboxyhemoglobin, methemoglobin, etc., without the use of high power optical sources like side emitting LEDs. Instead, such embodiments may employ other types of optical sources, such as top emitting LEDs. Alternatively, the emitter 1604 can use other types of sources of optical radiation, such as a laser diode, to emit near-infrared light into the measurement site 1602.

In addition, in some embodiments, in order to assist in achieving a comparative balance of desired power output between the LEDs, some of the LEDs in the emitter 1604 can have a filter or covering that reduces and/or cleans the optical radiation from particular LEDs or groups of LEDs. For example, since some wavelengths of light can penetrate through tissue relatively well, LEDs, such as some or all of the top-emitting LEDs can use a filter or covering, such as a cap or painted dye. This can be useful in allowing the emitter 1604 to use LEDs with a higher output and/or to equalize intensity of LEDs.

The data collection system 1600 also includes a driver 1611 that drives the emitter 1604. The driver 1611 can be a circuit or the like that is controlled by the monitor 1609. For example, the driver 1611 can provide pulses of current to the emitter 1604. In an embodiment, the driver 1611 drives the emitter 1604 in a progressive fashion, such as in an alternating manner. The driver 1611 can drive the emitter 1604 with a series of pulses of about 1 milliwatt (mW) for some wavelengths that can penetrate tissue relatively well and from about 40 mW to about 100 mW for other wavelengths that tend to be significantly absorbed in tissue. A wide variety of other driving powers and driving methodologies can be used in various embodiments.

The driver 1611 can be synchronized with other parts of the sensor 1601 and can minimize or reduce jitter in the timing of pulses of optical radiation emitted from the emitter 1604. In some embodiments, the driver 1611 is capable of driving the emitter 1604 to emit optical radiation in a pattern that varies by less than about 10 parts-per-million.

The detectors 1606 capture and measure light from the measurement site 1602. For example, the detectors 1606 can capture and measure light transmitted from the emitter 1604 that has been attenuated or reflected from the tissue in the measurement site 1602. The detectors 1606 can output a detector signal 1607 responsive to the light captured or measured. The detectors 1606 can be implemented using one or more photodiodes, phototransistors, or the like.

In addition, the detectors 1606 can be arranged with a spatial configuration to provide a variation of path lengths among at least some of the detectors 1606. That is, some of the detectors 1606 can have the substantially, or from the perspective of the processing algorithm, effectively, the same path length from the emitter 1604. However, according to an embodiment, at least some of the detectors 1606 can have a different path length from the emitter 1604 relative to other of the detectors 1606. Variations in path lengths can be helpful in allowing the use of a bulk signal stream from the detectors 1606. In some embodiments, the detectors 1606 may employ a linear spacing, a logarithmic spacing, or a two or three dimensional matrix of spacing, or any other spacing scheme in order to provide an appropriate variation in path lengths.

The front end interface 1608 provides an interface that adapts the output of the detectors 1606, which is responsive to desired physiological parameters. For example, the front end interface 1608 can adapt a signal 1607 received from one or more of the detectors 1606 into a form that can be processed by the monitor 1609, for example, by a signal processor 1610 in the monitor 1609. The front end interface 1608 can have its components assembled in the sensor 1601, in the monitor 1609, in connecting cabling (if used), combinations of the same, or the like. The location of the front end interface 1608 can be chosen based on various factors including space desired for components, desired noise reductions or limits, desired heat reductions or limits, and the like.

The front end interface 1608 can be coupled to the detectors 1606 and to the signal processor 1610 using a bus, wire, electrical or optical cable, flex circuit, or some other form of signal connection. The front end interface 1608 can also be at least partially integrated with various components, such as the detectors 1606. For example, the front end interface 1608 can include one or more integrated circuits that are on the same circuit board as the detectors 1606. Other configurations can also be used.

The front end interface 1608 can be implemented using one or more amplifiers, such as transimpedance amplifiers, that are coupled to one or more analog to digital converters (ADCs) (which can be in the monitor 1609), such as a sigma-delta ADC. A transimpedance-based front end interface 1608 can employ single-ended circuitry, differential circuitry, and/or a hybrid configuration. A transimpedance-based front end interface 1608 can be useful for its sampling rate capability and freedom in modulation/demodulation algorithms. For example, this type of front end interface 1608 can advantageously facilitate the sampling of the ADCs being synchronized with the pulses emitted from the emitter 1604.

The ADC or ADCs can provide one or more outputs into multiple channels of digital information for processing by the signal processor 1610 of the monitor 1609. Each channel can correspond to a signal output from a detector 1606.

In some embodiments, a programmable gain amplifier (PGA) can be used in combination with a transimpedance-based front end interface 1608. For example, the output of a transimpedance-based front end interface 1608 can be output to a PGA that is coupled with an ADC in the monitor 1609. A PGA can be useful in order to provide another level of amplification and control of the stream of signals from the detectors 1606. Alternatively, the PGA and ADC components can be integrated with the transimpedance-based front end interface 1608 in the sensor 1601.

In another embodiment, the front end interface 1608 can be implemented using switched-capacitor circuits. A switched-capacitor-based front end interface 1608 can be useful for, in certain embodiments, its resistor-free design and analog averaging properties. In addition, a switched-capacitor-based front end interface 1608 can be useful because it can provide a digital signal to the signal processor 1610 in the monitor 1609.

As shown in FIG. 16, the monitor 1609 can include the signal processor 1610 and a user interface, such as a display 1612. The monitor 1609 can also include optional outputs alone or in combination with the display 1612, such as a storage device 1614 and a network interface 1616. In an embodiment, the signal processor 1610 includes processing logic that determines measurements for desired analytes, such as glucose, based on the signals received from the detectors 1606. The signal processor 1610 can be implemented using one or more microprocessors or subprocessors (e.g., cores), digital signal processors, application specific integrated circuits (ASICs), field programmable gate arrays (FPGAs), combinations of the same, and the like.

The signal processor 1610 can provide various signals that control the operation of the sensor 1601. For example, the signal processor 1610 can provide an emitter control signal to the driver 1611. This control signal can be useful in order to synchronize, minimize, or reduce jitter in the timing of pulses emitted from the emitter 1604. Accordingly, this control signal can be useful in order to cause optical radiation pulses emitted from the emitter 1604 to follow a precise timing and consistent pattern. For example, when a transimpedance-based front end interface 1608 is used, the control signal from the signal processor 1610 can provide synchronization with the ADC in order to avoid aliasing, cross-talk, and the like. As also shown, an optional memory 1613 can be included in the front-end interface 1608 and/or in the signal processor 1610. This memory 1613 can serve as a buffer or storage location for the front-end interface 1608 and/or the signal processor 1610, among other uses. Further, a motion sensor 1615 is included, as described above, for providing a motion signal used for calculating blood pressure.

The user interface 1612 can provide an output, e.g., on a display, for presentation to a user of the data collection system 1600. The user interface 1612 can be implemented as a touch-screen display, an LCD display, an organic LED display, or the like. In addition, the user interface 1612 can be manipulated to allow for measurement on the non-dominant side of patient. For example, the user interface 1612 can include a flip screen, a screen that can be moved from one side to another on the monitor 1609, or can include an ability to reorient its display indicia responsive to user input or device orientation. In alternative embodiments, the data collection system 1600 can be provided without a user interface 1612 and can simply provide an output signal to a separate display or system.

A storage device 1614 and a network interface 1616 represent other optional output connections that can be included in the monitor 1609. The storage device 1614 can include any computer-readable medium, such as a memory device, hard disk storage, EEPROM, flash drive, or the like. The various software and/or firmware applications can be stored in the storage device 1614, which can be executed by the signal processor 1610 or another processor of the monitor 1609. The network interface 1616 can be a serial bus port (RS-232/RS-485), a Universal Serial Bus (USB) port, an Ethernet port, a wireless interface (e.g., WiFi such as any 802.1x interface, including an internal wireless card), or other suitable communication device(s) that allows the monitor 1609 to communicate and share data with other devices. The monitor 1609 can also include various other components not shown, such as a microprocessor, graphics processor, or controller to output the user interface 1612, to control data communications, to compute data trending, or to perform other operations.

Although not shown in the depicted embodiment, the data collection system 1600 can include various other components or can be configured in different ways. For example, the sensor 1601 can have both the emitter 1604 and detectors 1606 on the same side of the measurement site 1602 and use reflectance to measure analytes. The data collection system 1600 can also include a sensor that measures the power of light emitted from the emitter 1604.

Figure 17:
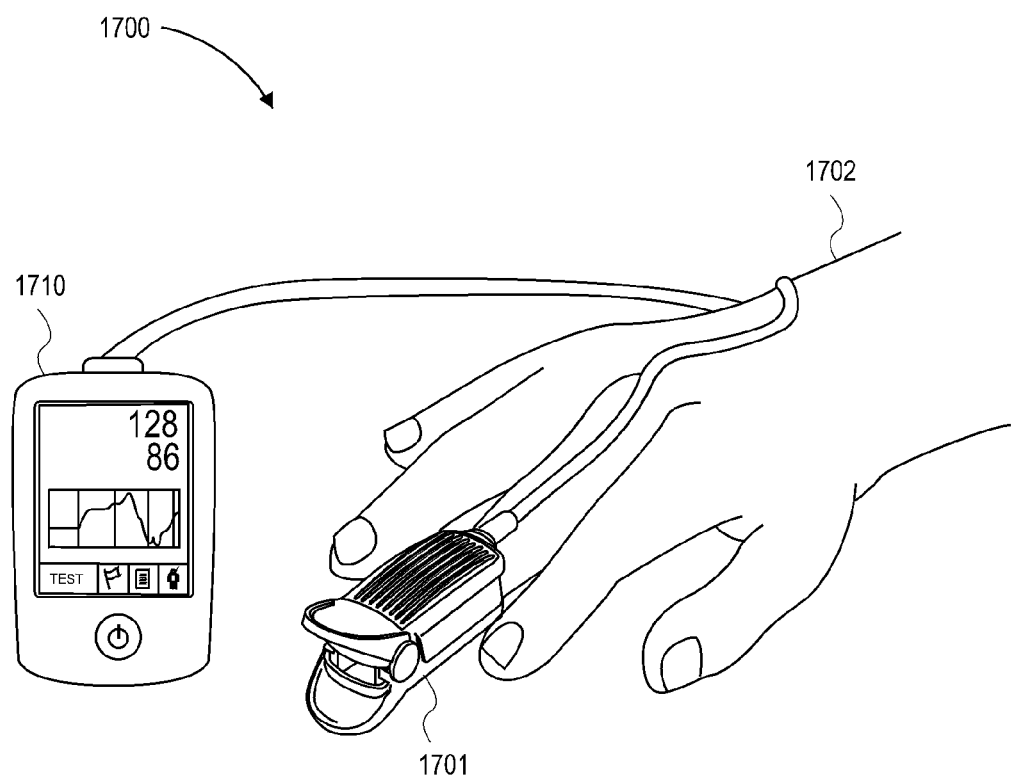
FIGS. 17-19 illustrate example embodiments of blood pressure measurement devices.
Figure 18:
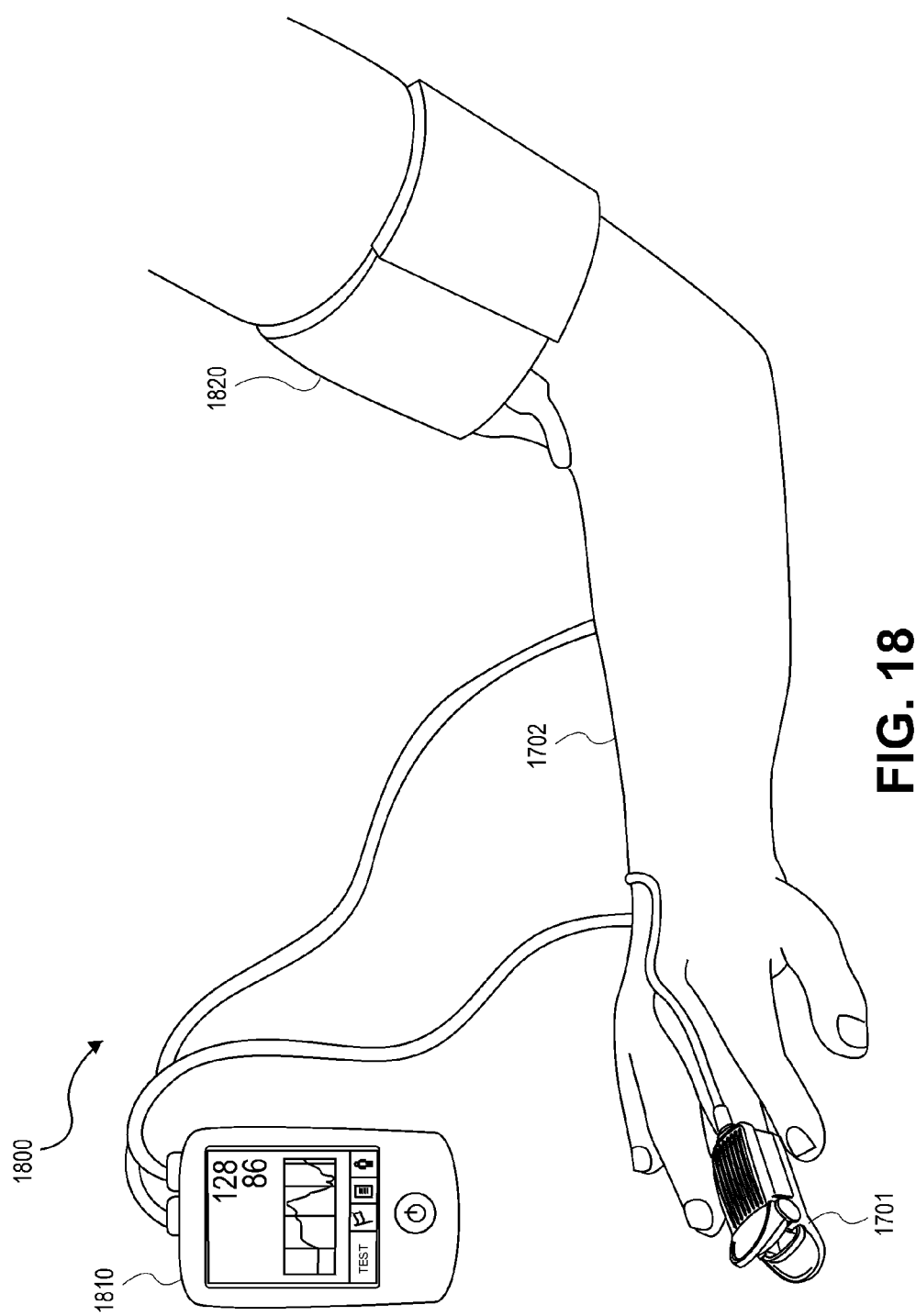
Figure 19:
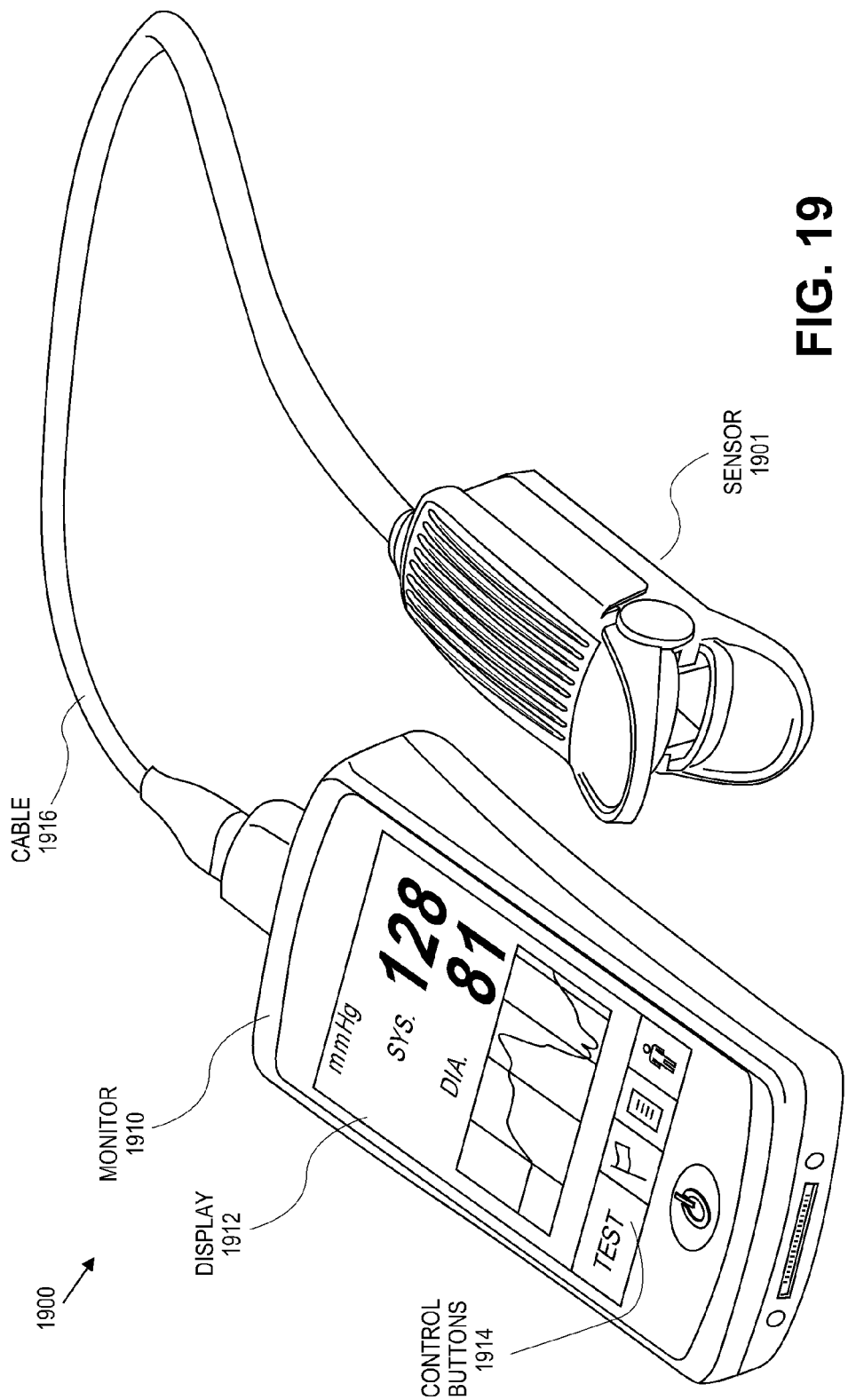

FIGS. 17 through 19 illustrate example embodiments of blood pressure measurement devices 1700, 1800, and 1900. Referring to FIG. 17, an example monitoring system 1700 is shown that can implement the parameter calculation system 100 or any of the other systems and algorithms described herein. The monitoring system 1700 includes a noninvasive monitor 1710, which is coupled to an individual 1702 via a sensor 1701. The sensor 1701 can include a noninvasive optical sensor and a motion sensor in a single housing. In alternative embodiments, the optical and motion sensors are provided in separate housings.

The sensor 1701 can provide photoplethysmograph and motion data to the noninvasive monitor 1710. The noninvasive monitor 1710 can calculate blood pressure (among other parameters) based at least in part on the photoplethysmograph and motion data. The noninvasive monitor 1710 can display blood pressure values, waveforms, alarms, and the like. The noninvasive monitor 1710 can measure blood pressure continuously and/or can be used for spot-check measurements.

Referring to FIG. 18, another example monitoring system 1800 is shown that can implement the parameter calculation system 100 or any of the other systems and algorithms described herein. The monitoring system 1800 includes a monitor 1810 that obtains blood pressure measurements noninvasively from a sensor 201 coupled to an individual 202. Additionally, the monitoring system 1800 includes an alternative blood pressure measurement device 1820.

In the depicted embodiment, the alternative blood pressure measurement device 1820 is an oscillometric cuff 1820. The oscillometric cuff 1820 can automatically inflate and occlude blood vessels using intelligent cuff inflation (ICI) techniques, thereby generating blood pressure signals that can be output to the monitor 1810. In other embodiments, the alternative blood pressure measurement device used can be a manually-operated cuff and stethoscope. In some embodiments, the alternative blood pressure measurement device can be an invasive pressure transducer.

In many care settings, oscillometric cuffs are used as the gold standard for periodically obtaining blood pressure readings from patients. Because cuffs occlude blood vessels, however, too-frequent blood pressure readings can damage blood vessels and possibly cause nerve damage. On the other hand, if blood pressure readings are not taken frequently enough, significant changes in blood pressure can be missed, potentially resulting in harm to a patient. Thus, in certain embodiments, the monitor 1810 can obtain noninvasive blood pressure measurements using the sensor 201. If the noninvasive blood pressure measurements deviate from a threshold, the monitor 1810 can trigger the occlusive cuff 1820 (or other alternative device) to obtain an occlusive (or other alternative) blood pressure measurement. As a result, occlusive, gold-standard measurements can be taken less frequently when noninvasive measurements are within a threshold range, potentially reducing damage to blood vessels.

FIG. 19 illustrates another example monitoring device 1900 in which the parameter calculation system 100 or any of the other systems and algorithms described herein can be implemented for measuring blood pressure and other physiological parameters. Advantageously, in certain embodiments, the example monitoring device 1900 shown can have a shape and size that allows a user to operate it with a single hand or attach it, for example, to a user's body or limb. The features of the monitoring device 1900 can also be included in the monitoring systems 1700, 1800 described above.

In the depicted embodiment, the monitoring device 1900 includes a finger clip sensor 1901 connected to a monitor 1910 via a cable 1916. In the embodiment shown, the monitor 1910 includes a display 1912, control buttons 1914 and a power button. Moreover, the monitor 1910 can advantageously include electronic processing, signal processing, and data storage devices capable of receiving signal data from the sensor 1901, processing the signal data to determine one or more output measurement values indicative of one or more physiological parameters of a user, and displaying the measurement values, trends of the measurement values, combinations of measurement values, and the like.

The cable 1916 connecting the sensor 1901 and the monitor 1910 can be implemented using one or more wires, optical fiber, flex circuits, or the like. In some embodiments, the cable 1916 can employ twisted pairs of conductors in order to minimize or reduce cross-talk of data transmitted from the sensor 1901 to the monitor 1910. Various lengths of the cable 1916 can be employed to allow for separation between the sensor 1901 and the monitor 1910. The cable 1916 can be fitted with a connector (male or female) on either end of the cable 1916 so that the sensor 1901 and the monitor 1910 can be connected and disconnected from each other. Alternatively, the sensor 1901 and the monitor 1910 can be coupled together via a wireless communication link, such as an infrared link, a radio frequency channel, or any other wireless communication protocol and channel. The sensor 1901 could also be integrated with a monitor 1910 in other embodiments.

The monitor 1910 can be attached to the patient. For example, the monitor 1910 can include a belt clip or straps (not shown) that facilitate attachment to a patient's belt, arm, leg, or the like. The monitor 1910 can also include a fitting, slot, magnet, LEMO snap-click connector, or other connecting mechanism to allow the cable 1916 and sensor 1901 to be attached to the monitor 1910.

The monitor 1909 can also include other components, such as a speaker, power button, removable storage or memory (e.g., a flash card slot), an AC power port, and one or more network interfaces, such as a universal serial bus interface or an Ethernet port. For example, the monitor 1910 can include a display 1912 that can indicate a measurement for blood pressure, for example, a measurement of the systolic and diastolic blood pressure in mmHg. Other physiological parameter values, waveforms, and the like can also be output on the display 1912.

The sensor 1901 can measure various blood constituents or analytes noninvasively using multi-stream spectroscopy. In an embodiment, the multi-stream spectroscopy can employ visible, infrared and near infrared wavelengths. The sensor 1901 can include photocommunicative components, such as an emitter, a detector, and other components (not shown). The emitter can include a plurality of sets of optical sources that, in an embodiment, are arranged together as a point source. The various optical sources can emit a sequence of optical radiation pulses at different wavelengths towards a measurement site, such as a patient's finger. Detectors can then detect optical radiation from the measurement site. The optical sources and optical radiation detectors can operate at any appropriate wavelength, including, for example, infrared, near infrared, visible light, and ultraviolet. In addition, the optical sources and optical radiation detectors can operate at any appropriate wavelength, and modifications to the embodiments desirable to operate at any such wavelength can be used in certain embodiments.

The sensor 1901 can also include a motion sensor, such an accelerometer, a gyroscope, or the like. The accelerometer can be a one-axis, two-axis, three-axis, or higher-axis accelerometer, such as a six-axis accelerometer. The sensor 1901 can also include multiple motion sensors, including different types of motion sensors.

The sensor 1901 or the monitor 1910 can also provide outputs to a storage device or network interface. In addition, although a single sensor 1901 with a single monitor 1910 is shown, different combinations of sensors and device pairings can be implemented. For example, multiple sensors can be provided for a plurality of differing patient types or measurement sites.

VII. Blood Pressure Measurement System with Gas Reservoir

As described above, blood pressure (which can refer to diastolic pressure, systolic pressure, or some combination or mathematical representation of same), considered one of the principal vital signs, is one example of a physiological parameter that can be monitored. Blood pressure monitoring can be an important indicator of a wearer's cardiovascular status. Many devices allow blood pressure to be measured by manual or digital sphygmomanometer systems that utilize an inflatable cuff applied to a person's arm. These devices typically measure diastolic pressure and systolic pressure during deflation of the inflatable cuff.

For example, the inflatable cuff is inflated to a pressure level at or above the expected systolic pressure of the wearer and high enough to occlude an artery. Automated or motorized blood pressure monitoring systems use a motor or pump to inflate the inflatable cuff, while manual blood pressure monitors typically use an inflation bulb. As the air from the inflatable cuff slowly exits, the wearer's blood pressure can be determined by detecting Korotkoff sounds using a stethoscope or other detection means placed over the artery.

Alternatively, digital sphygmomanometers compute diastolic and systolic pressure as the inflatable cuff deflates based on the oscillations observed by a pressure sensor on the cuff. For example, some digital sphygmomanometers calculate the systolic blood pressure as the pressure at which the oscillations become detectable and the diastolic pressure as the pressure at which the oscillations are no longer detectable. Other digital sphygmomanometers calculate the mean arterial pressure first (the pressure on the cuff at which the oscillations have the maximum amplitude). The diastolic and systolic pressures are then calculated based on their fractional relationship with the mean arterial pressure. Other algorithms are used, such as identifying the change in slope of the amplitude of the pressure fluctuations to calculate the diastolic pressure.

As mentioned above, both methods of determining blood pressure include inflating the cuff to a pressure high enough to occlude an artery and then determining blood pressure during deflation of the inflatable cuff. Occluding the artery and then determining blood pressure during deflation can have a number of drawbacks. For example, inflating the inflatable cuff to a pressure higher than systolic pressure can cause pain and discomfort to the wearer. Other adverse effects can include limb edema, venous stasis, peripheral neuropathy, etc, or simply wearer interruption. In addition, as the artery is completely occluded prior to each measurement, sufficient time must elapse between measurements to ensure accurate results. Furthermore, manual systems make it difficult to measure blood pressure during inflation of the inflatable cuff due to the difficult of inflating the inflatable cuff at an approximately constant rate using an inflation bulb.

Digital blood pressure monitors can have additional drawbacks. The motors used to pump gas into the cuff are often noisy and can disturb wearers at rest. In addition to auditory noise, in automated or motorized systems, the motors can cause electrical noise in sensor signals making the signal processing attempting to identify reference points for blood pressure detection unreliable and difficult. Furthermore, portable motorized blood pressure monitors require a significant amount of power to produce the air pressure required to inflate the cuff. To provide the power levels required by the pump, a large battery is often used. The large battery makes the portable blood pressure monitor more cumbersome and less convenient. Furthermore, the large battery frequently needs to be recharged or replaced.

Advantageously, in certain embodiments, a blood pressure monitoring system can include a gas reservoir filled with sufficient quantities of compressed gas to inflate an inflatable cuff. The gas reservoir provides several advantages to the blood pressuring monitoring system, including portability, reusability, disposability, reduction in auditory noise and electrical noise, and the ability to measure blood pressure during inflation of the blood pressure cuff.

The addition of a gas reservoir to a blood pressure monitoring system makes it possible to inflate the inflatable cuff at an approximately constant rate with less auditory noise. By providing a quieter environment, the blood pressure monitoring system is capable of taking blood pressure measurements without disturbing the wearer. In addition, the use of the gas reservoir can significantly reduce the amount of electrical noise on the sensor signal. Furthermore, the addition of the gas reservoir allows the patient monitor to take blood pressure measurements during inflation of the inflatable cuff.

Measuring blood pressure during inflation can reduce the time required for blood pressure measurements and the amount of pressure used. Furthermore, measuring blood pressure during inflation can eliminate the need to occlude a wearer's artery.

In addition, the gas reservoir enables the manufacture of a smaller portable patient monitor. The gas reservoir can eliminate the need for a pump and/or motor in the portable patient monitor, thereby reducing its size. Furthermore, the gas in the gas reservoir can be used to generate electricity for the portable patient monitor, thereby eliminating the need for a battery and further reducing the size of the portable patient monitor.

Figure 20:
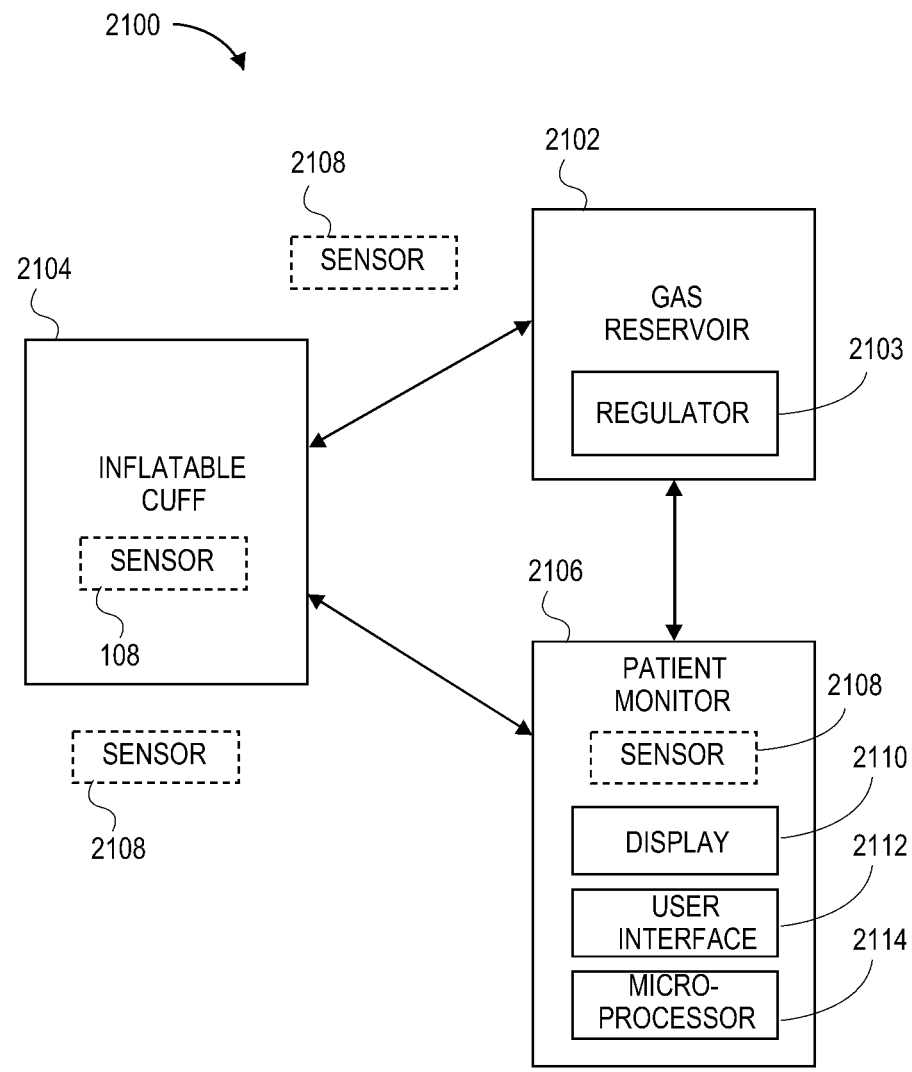
FIG. 20 is a block diagram illustrating an embodiment of a blood pressure monitoring system.

FIG. 20 is a block diagram illustrating an embodiment of a blood pressure monitoring system 2100 for measuring blood pressure of a wearer, which may also be referred to as taking blood pressure measurements, using an inflatable cuff 2104. The blood pressure monitoring system 2100 can be used to measure the blood pressure of a wearer during inflation, deflation or both. In an embodiment, the blood pressure monitoring system 2100 includes a gas reservoir 2102, an inflatable cuff 2104 and a patient monitor 2106.

The gas reservoir 2102 contains compressed gas and includes a regulator 2103 and is operatively connected to the inflatable cuff 2104 via a gas pathway, which allows gas to flow from the gas reservoir 2102 to the bladder of the inflatable cuff 2104. In one embodiment, the gas pathway is an airtight pathway constructed of any number of materials including, but not limited to, metal, plastic, cloth, or some other airtight material.

The gas reservoir 2102 can be implemented using one or more disposable or reusable gas tanks, cylinders, bottles, canisters, or cartridges, of any number of shapes or sizes, and can be located in the same room as the wearer, or can be remotely located from the wearer, such as in a different room or even in a different building. For example, the gas reservoir 2102 can include a large gas tank that remains in a stationary location. The gas reservoir 2102 can be large enough to contain sufficient gas for a large number of blood pressure readings (e.g. more than 100). Furthermore, The gas reservoir 2102 can store compressed gas at any number of PSI levels. For example, the gas reservoir can store compressed gas up to 6000 PSI or more, depending on the safety conditions of the environment. Furthermore, the gas tank can be configured to supply gas to multiple inflatable cuffs 2104, thereby limiting the number of gas tanks used for multiple wearers. When the pressure levels in the gas tank reach a threshold, the gas tank can either be refilled, replaced or a combination of both. For example a rotating cache of gas tanks can be used as the gas reservoir 2102.

Alternatively, the gas reservoir 2102 can be implemented using a small gas tank of any number of sizes. For example, the gas reservoir 2102 can be implemented using a gas tank that is small enough to fit in the palm of a hand, such as a carbon dioxide ($CO_2$) cartridge used for paint ball guns or tire inflation. $CO_2$ cartridges are available from a number of different manufacturers and distributors, such as the Air-Source 88 Gram Pre-filled Disposable $CO_2$ cartridge available from Crosman (Product Code: CRO-88-GRAM). The PSI levels for smaller gas tanks can also differ greatly and can store compressed gas up to 2000 PSI or more. In one embodiment, the gas reservoir 2102 is implemented using a gas tank containing compressed gas at 1000 PSI. The small gas reservoir 2102 can be used where mobility is important. For example, paramedics or first responders can carry a small gas reservoir 2102 for measuring blood pressure of persons needing emergency medical care. Using the gas reservoir 2102, the emergency personnel (or some other user) can measure the blood pressure of the wearer during inflation of the inflatable cuff, deflation, or a combination of the two. The measurements can be taken using a patient monitor 2106 or manually using a stethoscope.

In one embodiment, a pressure regulator, or regulator 2103, placed at an opening of the gas reservoir 2102 controls whether gas can exit the gas reservoir and the amount of gas allowed to exit. In one embodiment, the regulator is a valve. The regulator 2103 can also be configured to control the rate at which gas flows to the inflatable cuff 2104, as well as the pressure of the gas or PSI. The regulator 2103 can include a second regulator near the opening of the gas reservoir 2102 or in the gas pathway to form a two-stage pressure regulator. Additional regulators can be added as desired. The regulator 2103 and/or valve can be implemented using any number of different valves, such as a globe valve, butterfly valve, poppet valve, needle valve, etc., or any other type of valve capable of operating as a variable restriction to the gas flow. Furthermore, the regulator 2103 can include a pressure gauge to identify the pressure levels of the gas exiting the gas reservoir 2102 and/or in the gas pathway.

Using the regulator 2103, the inflatable cuff 2104 can be inflated at a controlled rate, such as, for example, an approximately constant rate. By inflating the inflatable cuff at a controlled rate, such as an approximately constant rate, the wearer's blood pressure can be measured during inflation and without occluding the artery. The regulator 2103 can further include a wireless transmitter for communication with the patient monitor 2106. Alternatively, the regulator 2103 can communicate with the patient monitor via wired communication. Additionally, the gas reservoir 2102 can include a pressure gauge to monitor the remaining pressure and/or the amount of compressed gas remaining in the gas reservoir 2102. The pressure gauge can communicate the pressure levels to the patient monitor 2106 via wired or wireless communication, similar to the regulator 2103. Once the pressure gauge indicates a threshold pressure level or gas level has been reached, the patient monitor 2106 can indicate that the gas reservoir 2102 should be replaced or refilled.

The gas reservoir 2102 can contain any number of compressed gases to inflate the inflatable cuff 2104. For example, the gas reservoir 2102 can contain compressed air, carbon dioxide, nitrogen, oxygen, helium, hydrogen, etc. Any number of other gases can be used to inflate the inflatable cuff 2104. Furthermore, the gas reservoir 2102 can contain enough gas to inflate the inflatable cuff 2104 without the use of a motor or pump during the inflation. The gas reservoir 2102 can be pre-filled with gas near the wearer or at a remote site away from the wearer. In one embodiment, the gas reservoir 2102 is filled with gas prior to being associated with the inflatable cuff 2104. Pre-filling the gas reservoir 2102 prior to use can significantly reduce the ambient noise caused during inflation of the inflatable cuff 2104. In addition, by using the gas reservoir 2102, the electrical noise from a motor can be removed. The reduction in ambient and electrical noise and the approximately constant rate of inflation of the inflatable cuff 2104 allows the patient monitor 2106 to measure the wearer's blood pressure while the inflatable cuff 2104 is inflating. In addition, the gas reservoir 2102 can be used to quickly inflate the inflatable cuff 2104 for blood pressure measurements taken during deflation of the inflatable cuff 2104.

It is to be understood that other techniques exist for implementing the gas reservoir 2102 without departing from the spirit and scope of the description. For example, the gas reservoir 2102 can be implemented using the central gas line of a building, such as a hospital or other healthcare facility. Alternatively, the gas reservoir 2102 can be implemented using a bulb, bladder, pump, or the like.

The inflatable cuff 2104 includes a bladder and fills with gas in a manner controlled by the patient monitor 2106 or manually, and is used to at least partially obstruct the flow of blood through a wearer's artery in order to measure the wearer's blood pressure. The inflatable cuff 2104 can be attached to a wearer's arm or other location, and can be inflated electronically (e.g., via intelligent cuff inflation) or manually using an inflation bulb to obtain blood pressure data. Blood pressure data can include any type of signal received from a sensor used to identify blood pressure. Blood pressure data can be in the form of pressure sensor data, auditory sensor data, and the like. The inflatable cuff 2104 can further include a wireless transmitter for wireless communication with the patient monitor 2106. Alternatively, the inflatable cuff can include cables for sending and receiving information to and from the patient monitor 2106. The inflatable cuff can receive gas from a gas reservoir 2102 via a gas pathway. Furthermore, the inflatable cuff can include a release valve for releasing the gas stored in the inflatable cuff once inflated. The release valve can be actuated electronically by the patient monitor 2106 or manually by a user. In one embodiment, the release valve can be used when the pressure in the inflatable cuff 2104 reaches unsafe levels or when the inflatable cuff 2104 has been inflated beyond a threshold period of time.

A sensor 2108 can be placed in close proximity to the inflatable cuff 2104 to monitor the inflatable cuff 2104 during inflation and deflation. Alternatively, the sensor 2108 can be located in the patient monitor 2106 along a gas pathway between the gas reservoir 2102 and inflatable cuff 2104, or at some other location where it is able to collect sufficient data for the patient monitor 2106 to determine the blood pressure of the wearer.

The sensor 2108 can be a pressure sensor or an auditory sensor. In one embodiment, the sensor 2108 communicates the pressure measurements of the inflatable cuff 2104 to the patient monitor 2106 via wired or wireless communication.

The pressure measurements can include blood pressure data of the wearer and can be used by the patient monitor to determine a blood pressure measurement of the wearer. The patient monitor 2106 can additionally use the pressure measurements to determine if the pressure in the inflatable cuff 2104 is above a threshold or is at an unsafe level. If the pressure in the inflatable cuff 2104 is above a threshold or is at an unsafe level, the patient monitor 2106 can actuate an emergency release valve to deflate the inflatable cuff 2104. In an embodiment where the sensor 2108 is an auditory sensor, the sensor 2108 can be used to detect Korotkoff sounds. In one embodiment, the sensor 2108 is a stethoscope.

In an embodiment, the patient monitor 2106 includes a display device 2110, a user interface 2112, and a microprocessor or microcontroller or combination thereof 2114. The patient monitor 2106 can further include a number of components implemented by the microprocessor 2114 for filtering the blood pressure data received from the sensor 2108 and determining the blood pressure of the wearer. The patient monitor 2106 can be a dedicated device for determining blood pressure, or can be part of a larger patient monitoring device capable of measuring additional physiological parameters as described in greater detail in U.S. application Ser. No. 10/153,263, entitled System and Method for Altering a Display Mode Based on a Gravity-Responsive Sensor, filed May 21, 2002, herein incorporated by reference in its entirety.

In some embodiments, the patient monitor 2106 is configured to communicate with the inflatable cuff 2104 and the gas reservoir 2102 via wired or wireless communication, such as LAN, WAN, WiFi, infra-red, Bluetooth, radio wave, cellular, or the like, using any number of communication protocols. The patient monitor 2106 can further be configured to determine blood pressure measurements of a wearer when the inflatable cuff 2104 is being inflated with gas from the gas reservoir 2102, during deflation of the inflatable cuff 2104, or a combination of both. The patient monitor 2106 can use the microprocessor 2114, the filtering component, and blood pressure monitoring component to determine the blood pressure measurements. The blood pressure measurements determined by the patient monitor 2106 can be displayed on the display 2110. In addition, the display 2110 can display blood pressure data and filtered blood pressure data in the form of plots of the pressure of the inflatable cuff and plots of the pressure oscillations in the inflatable cuff 2104 caused by blood flowing through an artery of the wearer. Furthermore, the display 2110 can display additional physiological parameters, such as heart rate, perfusion, oxygen saturation and the like.

The user interface 2112 can be used to allow a user to easily operate the patient monitor 2106 and obtain the blood pressure measurements. Furthermore, the user interface 2112 can allow a user to set or change any number of configuration parameters. For example, using the user interface 2112, a user can determine what is displayed on the display 2110, such as the blood pressure measurements during inflation and/or deflation, additional physiological parameters, and/or the pressure plots. Furthermore, the user interface 2112 can allow a user to set what measurements the patient monitor 2106 should take. For example, the user can set the configuration parameters to take blood pressure measurements only during inflation or deflation. Alternatively, the user can use the user interface 2112 to set the configuration parameters to take blood pressure measurements during inflation and deflation and then use both measurements to determine an appropriate blood pressure.

In addition, using the user interface 2122, the user can determine how often the patient monitor 2106 takes blood pressure measurements. The user interface 2112 can further be used for any other type of configuration parameters that can be set or changed by a user.

Figure 21:
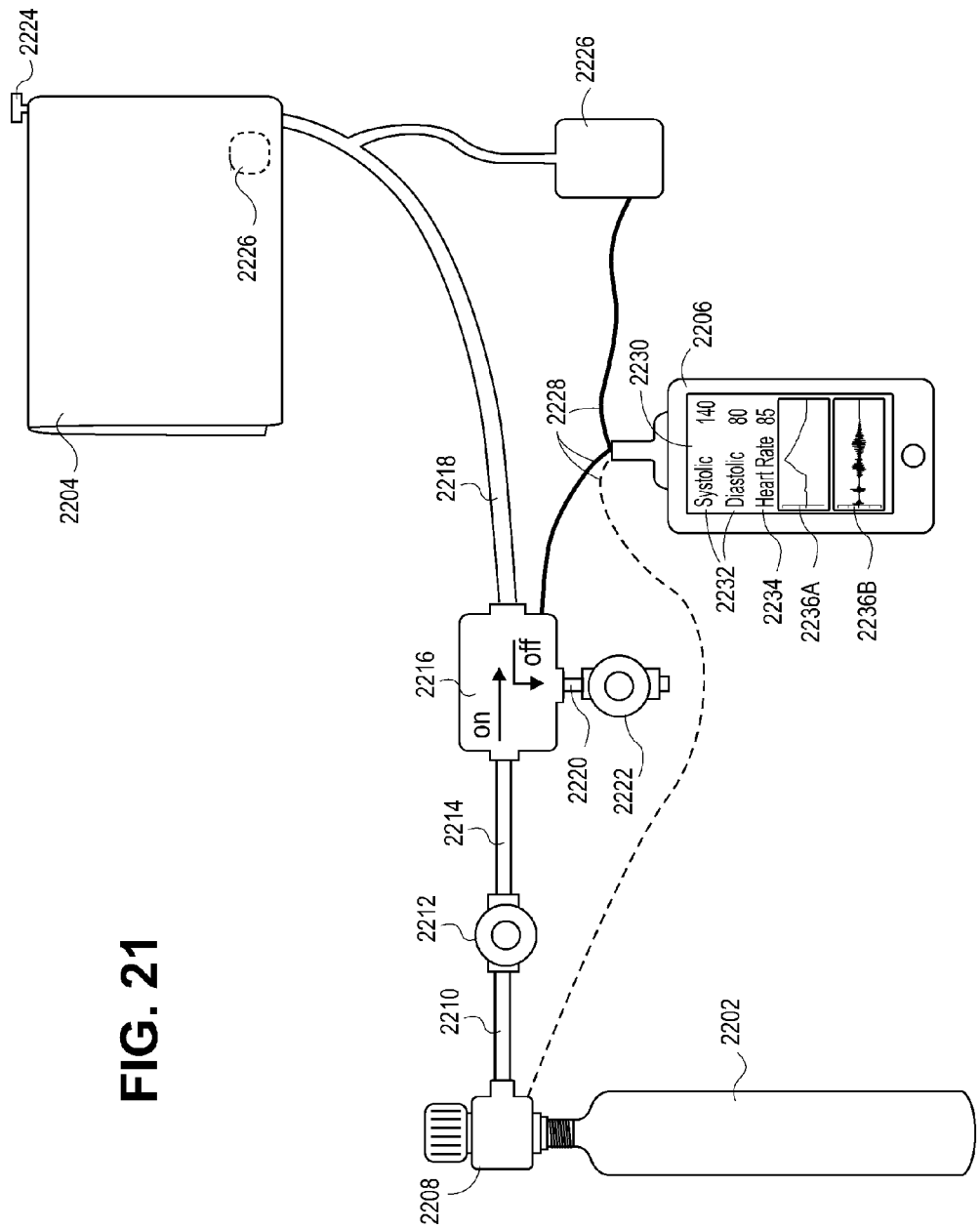
FIG. 21 is a system diagram illustrating an embodiment of the blood pressure monitoring system of FIG. 20.

FIG. 21 illustrates a blood pressure monitoring system 2200 similar to the blood pressure monitoring system 2100 of FIG. 20. Similar to the blood pressure monitoring system 2100 of FIG. 20, the blood pressure monitoring system 2200 of FIG. 21 includes a gas reservoir 2202, an inflatable cuff 2204, a patient monitor 2206, and a sensor 2226. In addition, the blood pressure monitoring system 2200 includes a gas pathway having a number of gas pathway segments 2210, 2214, 2218 and valves 2212, 2216, 2222 facilitating the movement of gas throughout the system. The gas reservoir 2202, the inflatable cuff 2204, the patient monitor 2206, the valve 2216, and the sensor 2226 can communicate using wired or wireless communication. Cables 2228 can be used to facilitate communication between the various components of the blood pressure monitoring system 2200. The various components can all be connected directly to each other or can all connect to a central location, such as the patient monitor 2206. Alternatively, the cables 2228 can be removed and the patient monitor 2202 can communicate with the other components of the blood pressure monitoring system via wireless communication.

As mentioned previously with reference to FIG. 20, the gas reservoir 2202 can be implemented using one or more gas tanks of any number of different sizes. In addition, the gas reservoir 2202 can be located in the same room as the wearer or can be located at a remote location, such as in a different room or different building from the wearer. In such an embodiment, the gas pathway runs from the wearer to the remote location where the gas reservoir 2202 is located. In addition, the gas reservoir 2202 can be filled with any number of different gases prior to use with the wearer 2218. In other words, the gas reservoir 2202 can be filled with gas prior to installation with the other components of the blood pressure monitoring system 2200. In one embodiment, the gas reservoir 2202 is filled with a compressed gas.

Furthermore, the gas from the gas reservoir 2202 can be used to generate electricity for the blood pressure monitoring system 2200. A small turbine can be located near the opening of the gas reservoir 2202, along the gas pathway, or near an opening of the inflatable cuff 2204. As the gas flows by the turbine and into the inflatable cuff 2202, the turbine rotates. The rotation of the turbine can be used to generate electricity for the blood pressure monitoring system 2200. The electricity can be fed to the patient monitor 2206 so that the patient monitor 2206 can measure the blood pressure of the wearer as the inflatable cuff inflates. Another turbine can be located near the release valve 2224 of the inflatable cuff 2204 or the gas pathway segment 2220. When the release valve 2224 of the inflatable cuff 2204 is opened or the valve 2216 is actuated, the exiting gas causes the turbine to rotate, thereby generating electricity. The generated electricity can be fed to the patient monitor 2206, allowing the patient monitor to measure the blood pressure of the wearer as the inflatable cuff 2204 deflates.

Using the gas reservoir 2202 to inflate the inflatable cuff 2204 can significantly reduce the ambient noise caused by the blood pressure monitoring system, resulting in a quieter environment for the wearer. In addition, the gas reservoir 2202 can supply gas at an approximately constant pressure and rate. Thus, the blood pressure monitoring system 2200 can inflate the inflatable cuff at an approximately constant rate without the auditory and electrical noise of a motor or pump, resulting in a cleaner signal for the patient monitor 2206. Furthermore, by using the gas reservoir 2202, the patient monitor can measure the wearer's blood pressure during inflation of the inflatable cuff 2204.

By measuring the blood pressure during inflation of the inflatable cuff, the blood pressure monitoring system 2200 can measure the blood pressure in less time and using less pressure. Furthermore, measuring blood pressure during inflation of the inflatable cuff can reduce, and in some embodiments completely remove, the amount of time that the artery is occluded, allowing for more frequent blood pressure readings.

The gas reservoir 2202 is operatively connected with the inflatable cuff 2204 via the regulator 2208, gas pathway segments 2210, 2214, 2218 and valves 2212, 2216. The gas pathway and gas pathway segments 2210, 2214, 2218 can be made of any air-tight material, such as a plastic tube, metal, cloth, or the like. Gas from the gas reservoir 2202 flows through the gas pathway segments 2210, 2214, 2218 to inflate the inflatable cuff 2204. In an embodiment, the regulator 2208, the gas pathway segments 2210, 2214, 2218 and the valves 2212, 2216, 2222 control the direction and rate of gas flow throughout the blood pressure monitoring system 2200. The regulator 2208, which can also be a valve, located near the opening of the gas reservoir 2202, controls the pressure of the gas exiting the gas reservoir 2202 and along the gas pathway segment 2210. The valve 2212 controls the pressure of the gas exiting gas pathway segment 2210 and along gas pathway segments 2214, 2218 to the inflatable cuff 2204. The regulator 2208 and valve 2212 can be configured as a two-stage pressure regulator and used to maintain an approximately constant pressure of gas entering the inflatable cuff 2204. The approximately constant pressure of gas leads to an approximately constant rate of inflation of the inflatable cuff 2204. The regulator 2208 and valve 2212 can be configured to maintain any number of pressure levels in the gas pathway segments 2210, 2214, 2218. In one embodiment, the regulator 2208 and valve 2212 are configured to maintain a pressure of approximately 6 PSI (pounds per square inch) along the gas pathway segment 2214 and gas pathway segment 2218.

The valve 2216 located along the gas pathway segments 2210, 2214, 2218 can be used to control the direction of the gas flow throughout the blood pressure monitoring system 2200. In an "on" configuration, the valve 2216 allows the gas to pass from the gas pathway segment 2214 to the gas pathway segment 2218 into the inflatable cuff 2204. In an "off" configuration, the valve 2216 closes the gas pathway between the gas reservoir 2202 and the inflatable cuff 2204 and opens a gas pathway from the inflatable cuff 2204 and gas pathway segment 2218 to the gas pathway segment 2220 and through valve 2222. The valve 2216 can be actuated electronically using the patient monitor 2206 or manually by a user. For safety, the default position for the valve 2216 can be the "off" configuration. In this way, should there be any malfunctions, the inflatable cuff 2204 can deflate. In an embodiment, the valve 2216 is a three-way valve. The valve 2216 can be implemented in a number of different ways without departing from the spirit and scope of the description.

The valve 2222 is similar in most respects to the valve 2212 and can control the rate at which gas is allowed to exit the inflatable cuff 2204. The valves 2212, 2222 can be implemented as any number of different valves, such as globe valve, butterfly valves, poppet valves, needle valves, proportional valves, etc., or any other type of valve capable of operating as a variable restriction to the gas flow. Furthermore, the valves 2212, 2222 can be actuated manually by a user or electronically by the patient monitor 2206.

A number of alternative embodiments exist for implementing the blood pressure monitoring system 2200 without departing from the spirit and scope of the description. For example, the valve 2216 can be located in the inflatable cuff 2204 or nearby. In addition, the valves 2216, 2222 can be removed completely. In this embodiment, the patient monitor 2206 can actuate the regulator 2208 and/or valve 2212 to inflate the inflatable cuff 2204. When the inflatable cuff 2204 is to be deflated, the patient monitor 2206 can actuate the regulator 2208 and/or valve 2212 a second time, as well as actuate the release valve 2224. Alternatively, two valves can be used in place of the valve 2216. One valve can be used to allow gas to flow from the gas reservoir to the inflatable cuff. The second valve can be used to release gas from the inflatable cuff. The two valves can be actuated independently or at the same time. Furthermore, the two valves can be actuated electronically using the patient monitor 2206 or manually by a user.

In addition, the regulator 2208 and valve 2212 can be implemented using any number of different configurations. For example, regulator 2208 and valve 2212 can be implemented as two separate devices as shown or as one single device. Alternatively, the blood pressure monitoring system 2200 can be implemented using only the regulator 2208 and/or the valve 2212. In addition, the regulator 2208 or any of the valves 2212, 2216, 2222 can further include a pressure gauge to identify the pressure levels of the gas. In addition, the regulator 2208 and each valve 2212, 2216, 2222 can communicate with the patient monitor 2206 via wired or wireless communication.

As mentioned previously, the inflatable cuff 2204 is used to at least partially obstruct an artery of a wearer to measure the wearer's blood pressure. In an embodiment, the inflatable cuff 2204 partially obstructs the wearer's artery without occluding, or completely closing, the artery to determine a blood pressure measurement of the wearer.

In one embodiment, the inflatable cuff 2204 includes a bladder, a release valve 2224 and an attachment mechanism. The bladder contains the gas received from the gas reservoir 2202, via the gas pathway and can be made of any material capable of holding gas. For example, the bladder can be made of plastic, cloth, or some other airtight material. Furthermore, the bladder can be configured to hold gas at any number of PSI levels. In one embodiment, the bladder is capable of holding gas at 4 PSI. However, it is to be understood that the bladder can hold gas at greater than or less than 4 PSI. An opening in the bladder allows the gas from the gas reservoir to enter exit.

The attachment mechanism allows the inflatable cuff 2204 to be attached to a wearer. The attachment mechanism can be made of Velcro, cloth, a clip, or other material that allows the inflatable cuff 2204 to attach to a wearer. The release valve 2224 can be actuated manually by a user, electronically by the patient monitor 2206, or automatically based on a predefined threshold pressure level. The release valve 2224 can be used to release the gas from the inflatable cuff 2204 when the pressure reaches a predetermined threshold or unsafe level, or when the inflatable cuff 2204 has been inflated above a threshold pressure for a predetermined amount of time.

The sensor 2226 can be located on the inside of the inflatable cuff 2204, at the patient monitor 2206, along the gas pathway segments 2210, 2214, 2218 or along a separate gas pathway segment, as illustrated in FIG. 21. Alternatively, the sensor 2226 can be located at the wearer's ear, wrist, finger, or other location. When obtaining blood pressure data from the finger, wrist, or ear less pressure is needed to identify the blood pressure of a wearer, which increases the amount of blood pressure measurements that can be taken by the gas reservoir 2202. As mentioned previously, the sensor 2226 can be used to collect blood pressure data from the wearer. In an embodiment, the sensor 2226 is a pressure sensor capable of measuring the pressure of the inflatable cuff 2204 as the inflatable cuff 2204 inflates and/or deflates. In another embodiment, the sensor 2226 is an auditory sensor used to identify Korotkoff sounds as the inflatable cuff 2204 inflates and/or deflates. The cables 2228 can be used to communicate the information from the sensor 2226 to the patient monitor 2206. Alternatively, the sensor 2226 can use a wireless transmitter to communicate the blood pressure data to the patient monitor 2206.

As mentioned previously, the patient monitor 2206 includes a display 2230 capable of displaying the diastolic and systolic pressure 2232 of the wearer as determined by the patient monitor 2206 during inflation and/or deflation. Furthermore, the patient monitor 2206 can display the blood pressure measured during inflation and deflation at the same time or simultaneously, thereby allowing the user to compare the values. The display 2230 of the patient monitor 2206 can further be configured to display pressure plots, which can include plots of the blood pressure data 2236A and filtered blood pressure data 2236B. The plots of the blood pressure data 2236A can include the pressure of the inflatable cuff 2204 over time, and the plots of the filtered blood pressure data 2236B can include the pressure oscillations observed by the sensor, as will be described in greater detail below with reference to FIGS. 22A-22C. In addition, the patient monitor 2206 can be configured to display additional physiological parameters 2234 as further illustrated on the display device 2208. These physiological parameters can include, but are not limited to, heart rate, oxygen saturation, perfusion, glucose measurements, and the like. In addition, the patient monitor 2206 can include configuration parameters to control the display 2230, as well as the patient monitor 2206. Using the configuration parameters, a user can initiate blood pressure measurements of the wearer 2218 to control the patient monitor 2206.

The patient monitor can also include a user interface for setting or changing the configuration parameters. The configuration parameters can be use to set the frequency and type of blood pressure measurements taken as well as the manner in which to display the measurements. For example, the configuration parameters can determine how often a blood pressure measurement should be taken, whether it should be taken during inflation, deflation or both. Furthermore the configuration parameters can determine how the patient monitor calculates the blood pressure measurements, such as using the inflationary blood pressure measurements, the deflationary blood pressure measurements, arbitrating between the two, or using a combination of the two. Furthermore, the configuration parameters can determine how the blood pressure measurements should be displayed. For example, the configuration parameters can dictate that only inflationary blood pressure measurements, deflationary blood pressure measurements, or a combination are to be displayed. Furthermore, the configuration parameters can determine if and how the pressure plots, and other physiological parameters are to be displayed.

In addition, the patient monitor 2206 can be configured to determine blood pressure measurements while the inflatable cuff 2204 is inflating and without occluding the wearer's artery. The patient monitor 2206 can be configured to actuate a valve connected to the gas reservoir 2202, causing gas to flow from the gas reservoir 2202 to the inflatable cuff 2204. As the inflatable cuff 2204 inflates, the patient monitor 2206 can calculate the diastolic pressure and systolic pressure of the wearer 2218 using any number of techniques, as described in greater detail below with reference to FIGS. 23A and 23B. For example, the patient monitor 2206 can calculate the diastolic pressure and systolic pressure by measuring oscillations of blood flow in an artery or auditory cues as the inflatable cuff 2204 inflates. By measuring the wearer's blood pressure during inflation of the inflatable cuff, both the diastolic and systolic pressure can be determined by partially obstructing the wearer's artery and without occluding it. Once the systolic pressure is measured, the patient monitor can actuate the valve 2216 or a release valve 2224 on the inflatable cuff 2204 to release the gas within the inflatable cuff 2204.

Figure 22A:
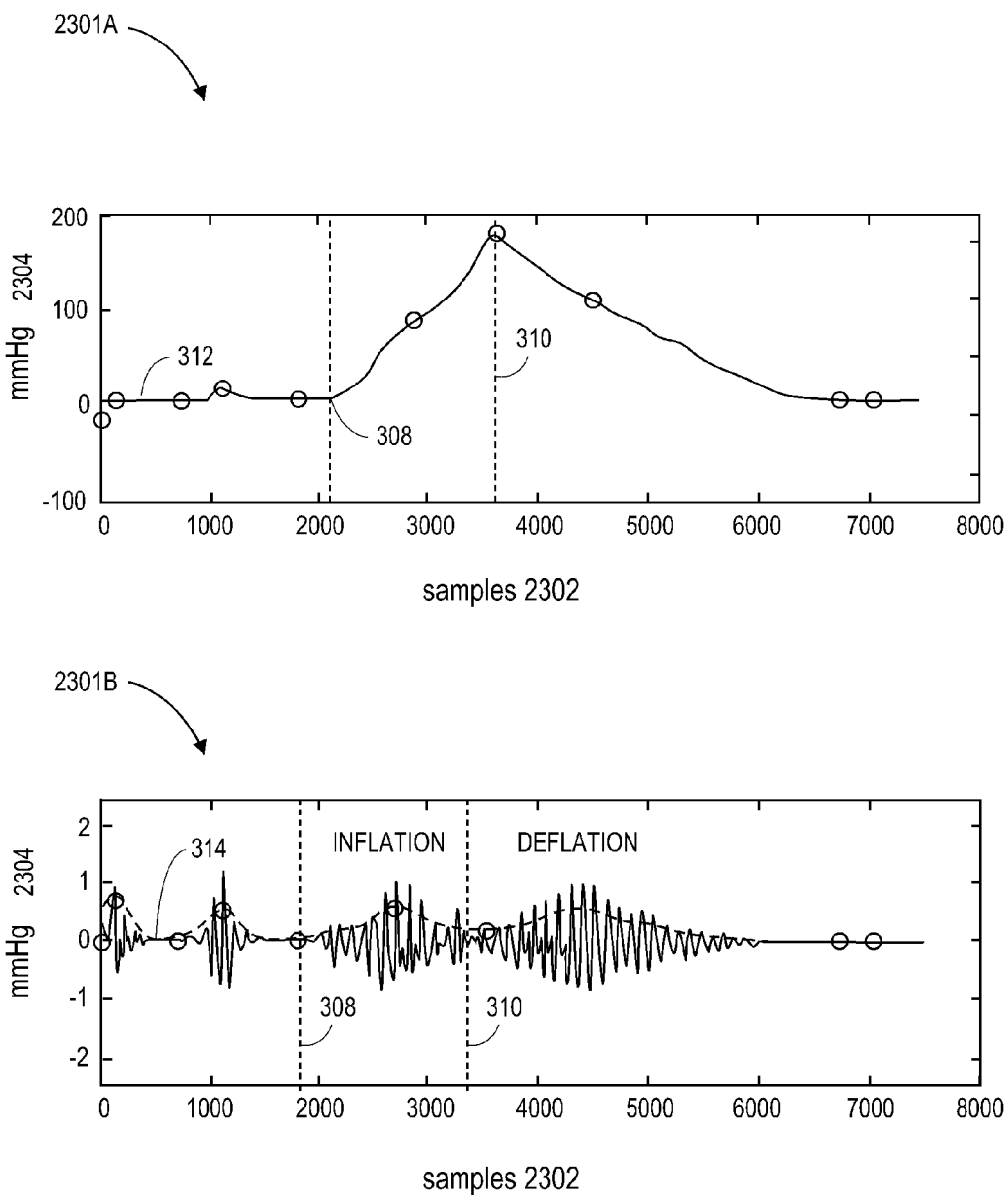
FIG. 22A-22C are plot diagrams illustrating embodiments of pressure variations of an inflatable cuff associated with a wearer during blood pressure measurement.
Figure 22B:
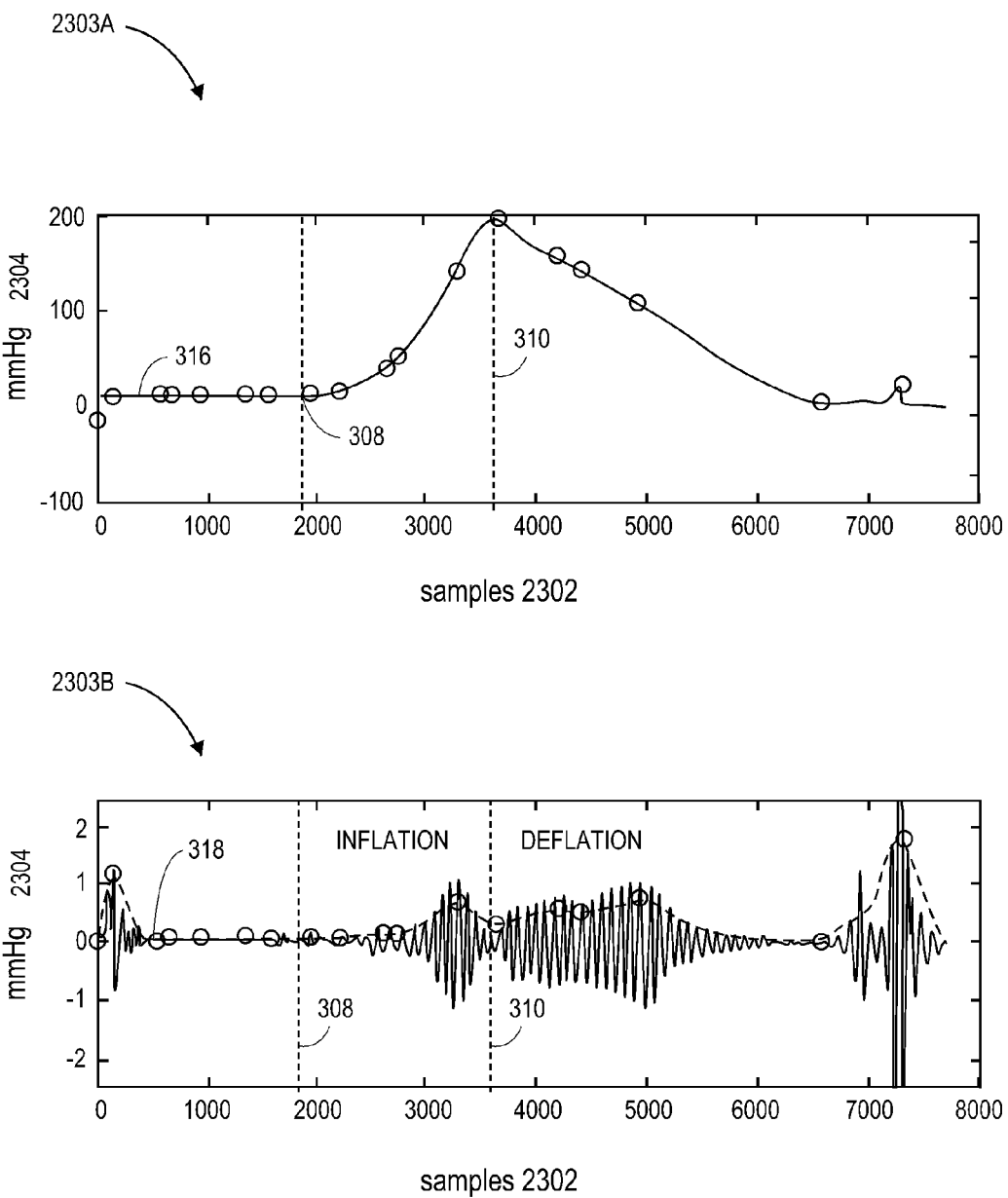
Figure 22C:
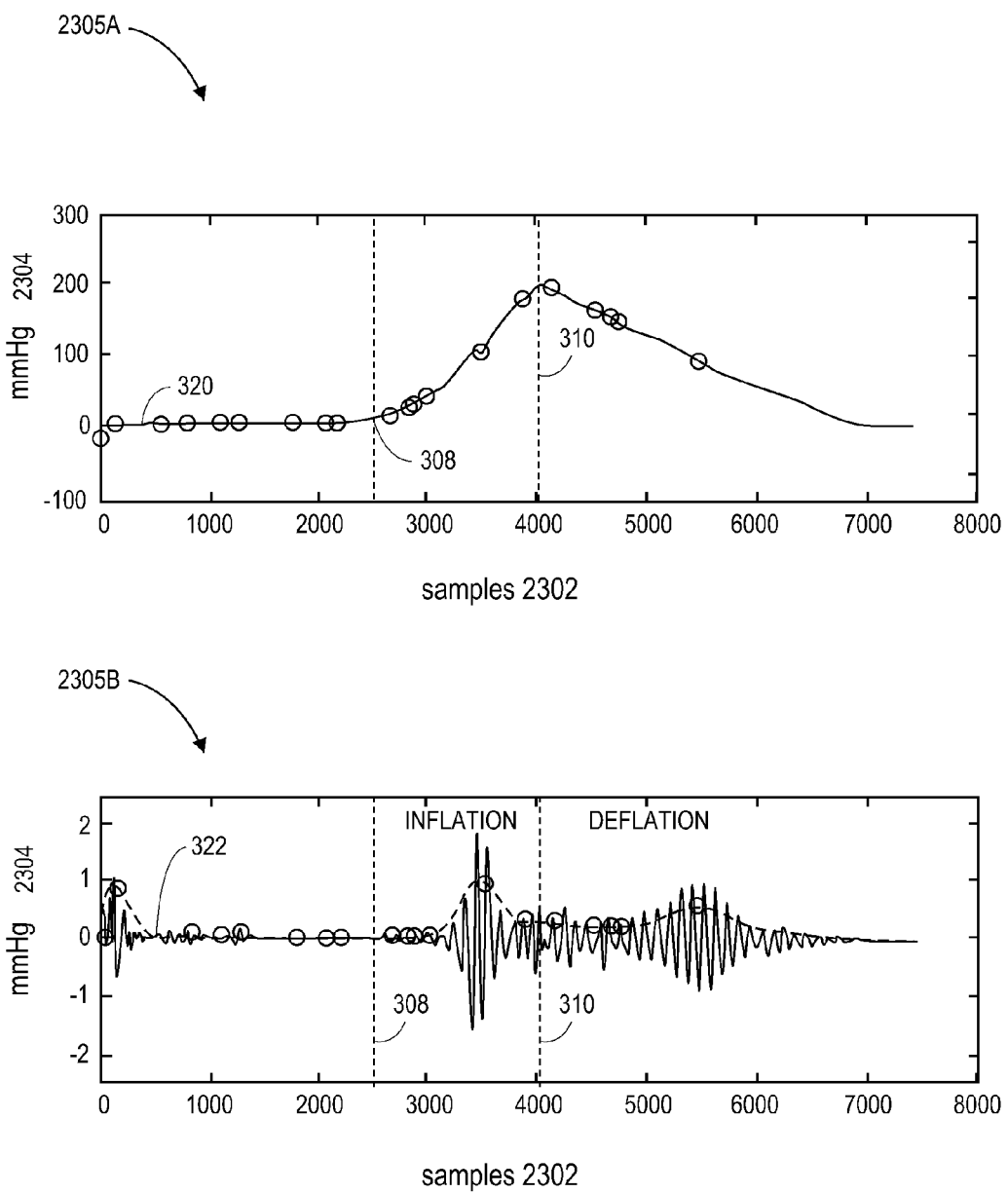

As mentioned previously, the display 2230 can be configured to display additional information regarding the wearer. FIGS. 22A-22C are plot diagrams illustrating embodiments of various plots that can be displayed by the display 2230. The plots in FIGS. 22A-22C are plot diagrams illustrating some embodiments of the pressure at the inflatable cuff 2204, including the oscillations of pressure, observed by the sensor 2226 during inflation and deflation.

Plot 2301A is a plot diagram illustrating an embodiment of the pressure of the inflatable cuff 2204 during inflation and deflation, which can also be referred to as blood pressure data. The x-axis of plot 2301A represents the number of samples taken by the patient monitor 2206 over time. The patient monitor 2206 can be configured to take samples at any number of increments to achieve a desired data resolution. For example, the patient monitor 2206 can sample the inflatable cuff every second, millisecond, microsecond, etc. Although illustrated in increments of samples, time can also be used for the x-axis 2302. The y-axis 2304A of plot 2301A represents the pressure level, in mmHg, of the inflatable cuff 2204. The line 2312 represents the pressure level of the inflatable cuff 2204 over time.

Prior to point 2308, signals on the line 2312 represent electronic noise caused by the environment or blood pressure monitoring system 2200. At point 2308, the valve 2216 is actuated. The valve 2216 can be actuated electronically by the patient monitor 2206 or manually by a user. Once actuated, gas from the gas reservoir 2202 begins to inflate the inflatable cuff 2204 at a rate determined by a user electronically using the patient monitor 2206 or manually using the regulator 2208 and/or valve 2212. In one embodiment, the inflation rate is an approximately constant rate, which leads to an approximately constant increase in pressure in the inflatable cuff. The sensor 2226 reads the rise in pressure in the inflatable cuff 2204, as indicated by the rise in line 2312 of the plot 2301A. Thus, from point 2308 to point 2310, the inflatable cuff is in an inflation mode and is inflating.

At point 2310, the valve 2216 is actuated again, ending the inflation of the inflatable cuff 2204. Although illustrated at 200 mmHg, the point 2310 can be located at any desired pressure level. In one embodiment, the 2216 valve is actuated when the measured pressure level within the inflatable cuff 2204 is greater than the expected systolic pressure of the wearer. The expected systolic pressure of the wearer can be determined by previous blood pressure measurements, historical information, clinical data from one or more wearers, or the like. In one embodiment, the point 2310 changes between blood pressure measurements. For example, the inflatable cuff can be configured to inflate to 200 mmHg for the first measurement. If it is determined during the first measurement that the wearer's systolic pressure is measurably less than 200, then during the proximate measurement, the inflatable cuff 2204 can be inflated to a lower pressure. Varying the pressure level to which the inflatable cuff 2204 inflates can conserve gas. Likewise, if the wearer's measured systolic pressure is greater than the expected systolic pressure, the inflatable cuff 2204 can be inflated to a greater pressure during the proximate measurement. Alternatively, the valve 2216 can be actuated once the inflatable cuff 2204 reaches any desired or predefined pressure level, such as 160 mmHg, 200 mmHg, 300 mmHg, etc.

In one embodiment, in addition to ending the inflation of the inflatable cuff, actuating the valve 2216 also begins a deflation mode of the inflatable cuff. For example, actuating the valve 2216 can close the gas pathway between the gas reservoir 2202 and the inflatable cuff 2204 and open the gas pathway between the inflatable cuff 2204 and ambient air, allowing the gas to exit the inflatable cuff 2204. Once the valve 2216 is actuated, the inflatable cuff 2204 deflates leading to a decrease in pressure within the inflatable cuff 2204. Actuating the valve 2216, as well as the valve 2222 can be configured so that the pressure within the inflatable cuff 2204 decreases at any desired rate. In one embodiment, the pressure within the inflatable cuff 2204 decreases at an approximately constant rate. Additional blood pressure measurements can be taken during the deflation of the inflatable cuff 2204, as described in greater detail below with reference to FIGS. 23A and 23B. The patient monitor 2206 can calculate the blood pressure of the wearer at any time during inflation and/or deflation, once it has received sufficient blood pressure data. For example, the patient monitor 2206 can calculate the diastolic pressure followed by the systolic pressure during inflation of the inflatable cuff 2204. Alternatively, the patient monitor can calculate both diastolic and systolic pressure simultaneously once the valve 2216 is actuated or during inflation, once the patient monitor 2206 has sufficient blood pressure data. The patient monitor 2206 can alternatively wait until additional measurements are taken during the deflation of the inflatable cuff 2204 before calculating the diastolic and systolic pressure. In this way, the patient monitor can compare or arbitrate the diastolic and systolic measurements during inflation and deflation of the inflatable cuff 2204 to achieve greater reliability in the measurements.

With continued reference to FIG. 22A, the plot 2301B is a plot diagram illustrating an embodiment of the change in pressure in the inflatable cuff 2204 due to blood flow in the artery during inflation and deflation of the inflatable cuff 2204. In one embodiment, the line 2314 is obtained by filtering the plot 2301A and normalizing the data based on the change in pressure due to the inflation and deflation of the inflatable cuff 2204 and can be referred to as filtered blood pressure data. The plot 2301B of the pressure oscillations due to the blood flow in the artery of the wearer, or filtered blood pressure data, can be displayed on the display 2230 along with the plot 2301A, the blood pressure readings, and/or other physiological parameters. Similar to plot 2301A, the x-axis 2302 of plot 2301B represents the number of samples taken by the patient monitor 2206 over time. The y-axis 2304B of plot 2301B represents normalized changes in pressure in the inflatable cuff 2204.

As illustrated in the plot 2301B, when the valve 2216 is actuated at point 2308, the inflatable cuff 2204 inflates and exerts pressure against the wearer's artery. As the inflatable cuff 2204 exerts pressure against the wearer's artery, the sensor 2226 is able to detect the variations in pressure in the inflatable cuff 2204 due to blood flow within the artery, which are also referred to as pressure variations or pressure oscillations. The pressure oscillations are illustrated in plot 2301A as small deviations or bumps in the line 2312.

As further illustrated by the plot 2301B, as the inflatable cuff 2204 continues to inflate, the artery becomes increasingly obstructed, leading to greater pressure variations observed by the pressure sensor, which leads to greater oscillations in the line 2314. With continued inflation of the inflatable cuff, the variations in pressure eventually begin to decrease as the blood flow becomes occluded. At point 2310, the pressure exerted by the inflatable cuff completely occludes the artery. As mentioned previously, in one embodiment, once the artery is occluded, the valve 2216 is actuated allowing the gas to exit the inflatable cuff 2204 and the inflatable cuff 2204 to deflate. In another embodiment, the valve 2216 is actuated prior to the occlusion of the artery.

As further illustrated by the plot 2301, as the inflatable cuff 2204 begins to deflate, the oscillations of the pressure observed by the pressure sensor 2226 again begin to increase significantly as blood flow in the artery increases. As the inflatable cuff 2204 further deflates, the pressure exerted on the artery decreases leading to a decrease in pressure variation observed by the pressure sensor 2226. Eventually, the inflatable cuff 2204 exerts little to no pressure on the artery, and the blood flow in the artery has little to no effect on the pressure in the inflatable cuff 2226. The patient monitor 2206 uses the characteristics of the oscillations of pressure due to blood flow through an artery of the wearer, such as the slope of the oscillations and/or the magnitude or amplitude of the oscillations, to determine the blood pressure. The patient monitor 2206 can use the blood pressure data obtained during inflation and/or deflation of the inflatable cuff to determine the blood pressure.

In one embodiment, to determine the blood pressure during inflation, the patient monitor identifies the pressure in the inflatable cuff at which the largest magnitude oscillation, also referred to as the maximum deflection point or largest amplitude oscillation, during inflation is detected. The pressure in the inflatable cuff at which the largest magnitude oscillation during inflation is detected coincides with the systolic blood pressure of the wearer. In one embodiment, the patient monitor also identifies the pressure in the inflatable cuff at which the largest slope in the oscillations prior to the largest magnitude oscillation during inflation is detected. The largest slope in the oscillations prior to the largest magnitude oscillation during inflation coincides with the diastolic pressure of the wearer.

In addition, the patient monitor can determine the blood pressure of the wearer during deflation. In one embodiment, to determine the blood pressure during deflation, the patient monitor identifies the largest magnitude oscillation during deflation. The patient monitor further identifies the pressure in the inflatable cuff at which the largest slope in the oscillations prior to the largest magnitude oscillation during deflation is detected. The largest slope in the oscillations prior to the largest magnitude oscillation during deflation coincides with the systolic pressure of the wearer. The patient monitor also identifies the pressure in the inflatable cuff at which the largest slope in the oscillations after the largest magnitude oscillation during deflation is detected. The largest slope in the oscillations after the largest magnitude oscillation during deflation coincides with the diastolic pressure of the wearer.

A number of alternate methods exist for determining blood pressure during inflation and deflation of the inflatable cuff. For example, during deflation the patient monitor can calculate the systolic blood pressure as the pressure at which the oscillations become detectable and the diastolic pressure as the pressure at which the oscillations are no longer detectable. Alternatively, the patient monitor can calculate the mean arterial pressure first (the pressure on the cuff at which the oscillations have the maximum amplitude). The patient monitor can then calculate the diastolic and systolic pressures based on their relationship with the mean arterial pressure. Additional methods can be used without departing from the spirit and scope of the description. For example, pressure values at locations other than the largest magnitude oscillation or maximum deflection point and largest slope can also be used.

Plots 2301A and 2301B further illustrate the potentially adverse effect signal noise can have on the blood pressure measurements. As illustrated, signal noise is detected at least twice in line 2314 prior to inflation. The detected signal noise in at least one instance exceeds the maximum deflection point during inflation. In addition, the signal noise may also contain the largest slope prior to the maximum deflection. In either event, if the signal noise is not accounted for, the patient monitor 2206 can erroneously detect the diastolic and systolic pressure of the wearer. In some embodiments, based on the amount and magnitude of signal noise detected, the patient monitor can assign confidence levels to the blood pressure measurements. Based on line 2314, the patient monitor 2206 can place a lower confidence level in the blood pressure measurement during inflation due to the observed signal noise.

As mentioned above, the plots 2301A, 2301B can both be displayed on the display 2230 of the patient monitor 2206. The plots 2301A, 2301B can be displayed simultaneously or consecutively. In addition the plots 2301A, 2301B can be displayed along with the diastolic pressure and systolic pressure as measured by the patient monitor 2206. Furthermore, the measured diastolic pressure and systolic pressure during inflation can be displayed along with the measured diastolic pressure and systolic pressure during deflation. In addition, the patient monitor 2206 can further display additional physiological parameters measured by the patient monitor 2206.

FIGS. 22B and 22C include plot diagrams illustrating additional embodiments of the pressure of the inflatable cuff 2204 during inflation and deflation. Plots 2303A and 2305A correspond to plot 2301A, and plots 2303B and 2305B correspond to plot 2301B. Similar to plots 2301A and 2301B, plots 2303A, 2303B, 2305A, and 2305B illustrate the inflation of the inflatable cuff 2204 beginning at point 2308 and ending at point 2310. In addition the deflation of the inflatable cuff begins at point 2310 in plots 2303A, 2303B, 2305A, and 2305B.

Plots 2303A and 2303B further illustrate signal noise being exhibited at different points throughout the lines 2316 and 2318. The first observed signal noise occurs near the beginning of the lines 2318 and another occurs near the end. Similar to the oscillations due to blood flow in the artery, signal noise is exhibited as small displacements on the line 2316 and oscillations in the line 2318. As illustrated, unless accounted for, the signal noise occurring in plots 2303A and 2303B can have an adverse affect on blood pressure measurements due to their magnitude. The first detected signal noise results in the maximum deflection point prior to deflation and the last detected signal noise results in the maximum deflection point after deflation. In embodiments, where maximum deflection points are used, if inflation and deflation are not demarcated appropriately or if signal noise is not accounted for, the patient monitor 2206 can erroneously determine the blood pressure measurements based on the signal noise.

The plot 2303B further illustrates an example where a blood pressure measurement taken during inflation can in some instance have a higher confidence level than the blood pressure measurement taken during deflation. As mentioned previously, during inflation, the diastolic pressure can be determined as the pressure at which the largest slope in line 2318 prior to the maximum deflection point during inflation occurs. The systolic pressure can be calculated as the pressure at which the maximum deflection point of line 2318 occurs during inflation. Upon deflation, the systolic pressure is calculated as the pressure at which the largest slope in line 2318 prior to the maximum deflection point during deflation occurs. Similarly, the diastolic pressure is calculated as the pressure at which the largest slope in line 2318 after the maximum deflection point during deflation occurs. As illustrated in plot 2303B, the maximum deflection point during deflation can be difficult to identify, which can make it difficult to calculate the diastolic and systolic pressure of the wearer accurately. Accordingly, the confidence placed in the blood pressure measurement during deflation can be relatively low compared to the confidence level placed in the blood pressure measurement during inflation. Accordingly, the patient monitor 2204 can determine that the blood pressure measurement taken during inflation is likely more accurate. In addition, depending on the amount and magnitude of the signal noise detected, the patient monitor 2206 can determine that neither blood pressure measurement reaches a threshold and that blood pressure measurements should be retaken.

Plots 2305A and 2305B illustrate yet another example of blood pressure measurements taken during inflation and deflation of the inflatable cuff 2204. As illustrated, signal noise is detected near the beginning of lines 2320 and 2322, resulting in oscillations observed in line 2322. As mentioned previously, if not accounted for, the signal noise can adversely affect the blood pressure measurements during inflation. However, in the line 2322, the maximum deflection point prior to deflation occurs during inflation. Thus, the signal noise at the beginning of the line 2322 should not affect the blood pressure measurements. Plots 2305A and 2305B further illustrate an example where the blood pressure measurement taken during inflation can have a similar confidence level as the confidence level of the blood pressure measurement taken during deflation. As illustrated, the line 2318 exhibits a distinctive maximum amplitude during inflation and during deflation.

Figure 23A:
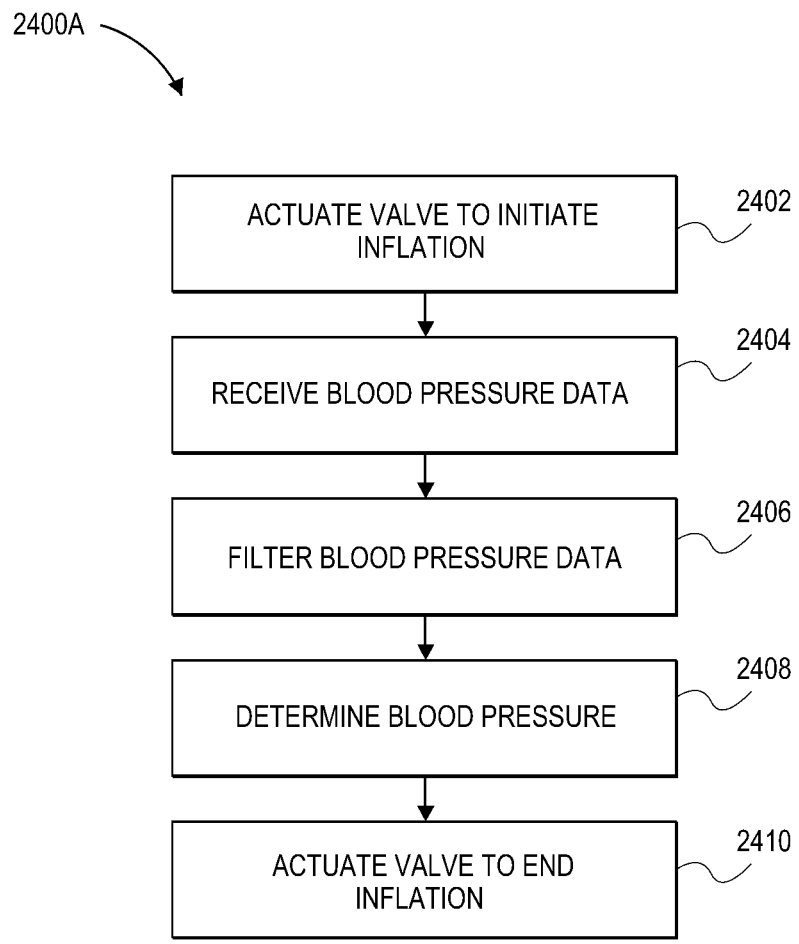
FIGS. 23A and 23B are flow diagrams illustrating embodiments of a process implemented by a patient monitor for measuring the blood pressure of a wearer.

FIG. 23A is a flow diagram illustrating an embodiment of a process 2400A for measuring blood pressure during inflation of an inflatable cuff 2204. As illustrated in FIG. 23A, the process 2400A begins at block 2402 by actuating a valve, which allows gas to flow from a gas reservoir 2202 to the inflatable cuff 2204, causing the inflatable cuff 2204 to inflate. The valve can be located near an opening of the gas reservoir 2202, at some point along the gas pathway or at the inflatable cuff 2204. In one embodiment, multiple valves 2212, 2216 and/or regulators 2208 can be included between the gas reservoir 2202 and the inflatable cuff 2204. Each valve and/or regulator can be actuated prior to inflating the inflatable cuff 2204. The valve(s) can be actuated manually by a user or electronically by a patient monitor 2206. For example, a user can manually open the valve 2216 to allow gas to flow from the gas reservoir 2202 to the inflatable cuff 2204. The user can open the valve in a way that allows for the inflation of the inflatable cuff 2204 at an approximately constant rate of inflation. A regulator 2208 can also be used to achieve the approximately constant rate of inflation. Alternatively, a patient monitor 2206 in communication with the gas reservoir can actuate the valve 2216, allowing the gas to flow from the gas reservoir 2202 to the inflatable cuff 2206. Communication from the patient monitor 2206 can occur by wired or wireless communication, such as a LAN, WAN, Wi-Fi, infra-red, Bluetooth, radio wave, cellular, or the like, using any number of communication protocols.

To actuate the valve, an input to the patient monitor 2206 such as a button can be used. Alternatively, the patient monitor can automatically actuate the valve once the patient monitor is turned on or based on one or more configuration parameters. For example, the patient monitor can be configured to determine the blood pressure of a wearer once every time period. The timer period can be configured as any period of time, such as 5 minutes, 15 minutes, 50 minutes, etc. In yet another embodiment, the patient monitor 2206 determines if the inflatable cuff is attached to a wearer. If the patient monitor 2206 determines that the inflatable cuff is attached to a wearer, the patient monitor 2206 can actuate the valve at predefined time intervals. Any number of methods can be used to determine if the inflatable cuff is attached to a wearer. For example, the patient monitor 2206 can determine whether the inflatable cuff is attached to a wearer using infra-red sensors, pressure sensors, capacitive touch, skin resistance, and the like.

Once the inflatable cuff 2204 is inflating, the patient monitor 2206 receives blood pressure data from the sensors, as illustrated in block 2404. The blood pressure data can be obtained at the inflatable cuff 2204 using any number of different sensors or methods. For example, a pressure sensor can be used to identify the air pressure due to the inflation and deflation of the inflatable cuff 2204. The pressure sensor can be located at the inflatable cuff, the patient monitor 2206, at some point along the gas pathway, or some other location where it is capable of measuring the pressure of the inflatable cuff 2204. Alternatively, an auditory sensor communicatively coupled to the patient monitor 2206 can be used to detect Korotkoff sounds, similar to the method used for manual determination of blood pressure using a stethoscope.

At block 2406, the patient monitor 2206 filters the blood pressure data. Filtering the blood pressure data can reduce the effects of, or completely remove, environmental noise and/or the electrical noise found within the blood pressure monitoring system. Furthermore, during filtering, the patient monitor 2206 can normalize the blood pressure data to account for the changes in pressure due to the inflation and deflation of the inflatable cuff. In one embodiment, after filtering the blood pressure data, only the pressure oscillations in the inflatable cuff 2204 due to blood flow in an artery of the wearer remain, and in some instances signal noise. Upon filtering the blood pressure data, the patient monitor 2206 can determine the blood pressure of the wearer, as illustrated in block 2408.

The patient monitor 2206 can determine the blood pressure using any number of different methods as described above with reference to FIGS. 22A-22C. For example, the patient monitor 2206 can determine the blood pressure of the wearer using the slopes and/or amplitude of the pressure oscillations, the mean arterial pressure, and/or the Korotkoff sounds.

Once the patient monitor 2206 determines the blood pressure of the wearer, the patient monitor 2206 can actuate a valve to stop gases from flowing from the gas reservoir to the inflatable cuff, as illustrated in block 2410. In one embodiment, the valve is a three-way valve 2216 and actuating the valve to stop the gases from flowing from the gas reservoir to the inflatable cuff also opens the gas pathway segment 2220 to release the gas from the inflatable cuff.

Fewer, more, or different blocks can be added to the process 2400A without departing from the spirit and scope of the description. For example, the patient monitor 2206 can filter the blood pressure data to determine the diastolic pressure first. As the diastolic pressure is being calculated, the patient monitor 2206 can continue receiving and filtering the blood pressure data to determine the systolic pressure. In an embodiment, the patient monitor can determine the blood pressure without filtering the blood pressure data. In addition, a user can determine the blood pressure measurements without the use of the patient monitor 2206. In an embodiment, a user using a stethoscope can determine the diastolic and systolic pressure during inflation of the inflatable cuff without filtering the blood pressure data.

As mentioned previously, by measuring the blood pressure during inflation of the inflatable cuff 2204, the blood pressure of the wearer can be measured in less time and using less pressure. Furthermore, because the artery is occluded for less time, or not occluded at all, the blood pressure can be measured more frequently.

Figure 23B:
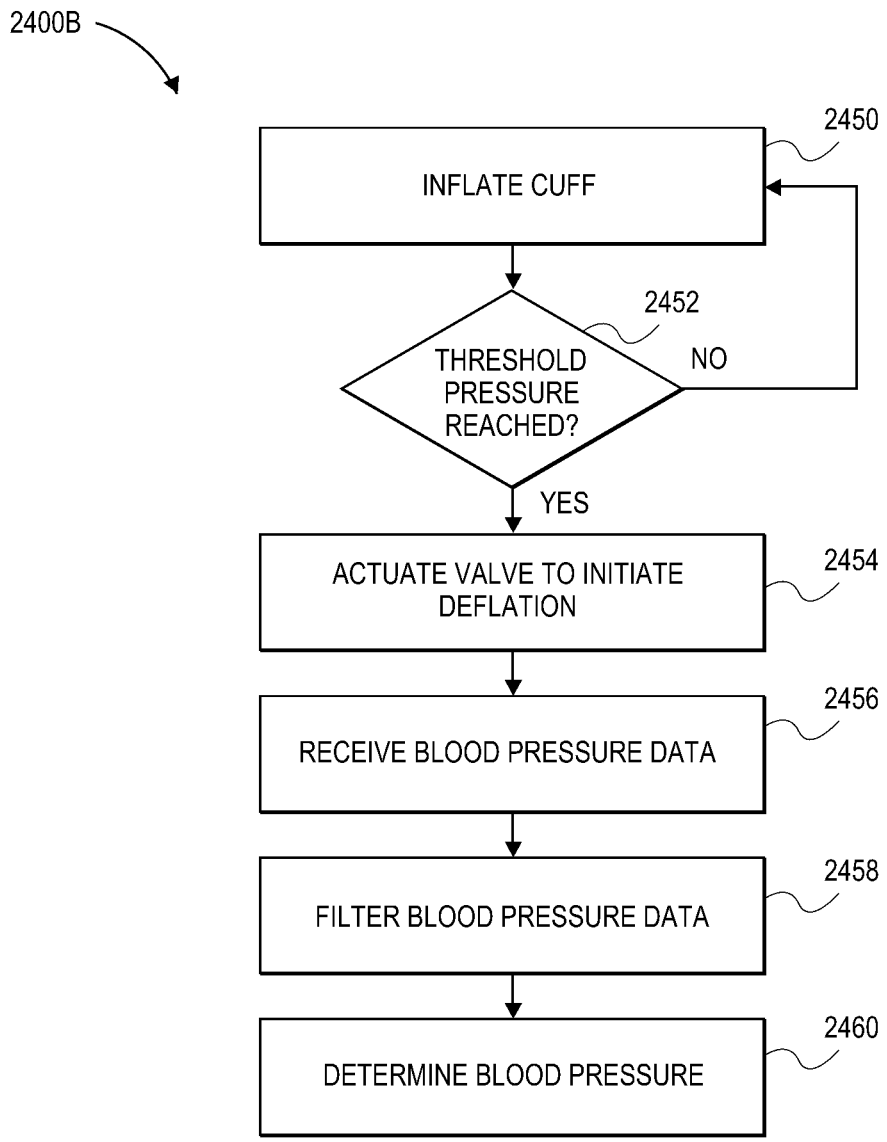

FIG. 23B illustrates a flow diagram of a process 2400B for measuring blood pressure during deflation of an inflatable cuff. At block 2450, the inflatable cuff 2204 is inflated. In one embodiment, the inflatable cuff 2204 is inflated using gas from a gas reservoir 2202. Using the gas from the gas reservoir 2202, the inflatable cuff 2204 can be inflated very quickly leading to a relatively short wait time before blood pressure measurements can be taken.

As the inflatable cuff 2204 inflates, the patient monitor determines whether a threshold pressure has been reached, as illustrated in block 2452. The threshold pressure can be any pressure level and can vary between blood pressure measurements. Furthermore, the threshold pressure can be determined based on previous blood pressure measurements, historical information, clinical data from one or more wearers, or the like. In one embodiment, the threshold pressure is above an expected systolic pressure of the wearer. In another embodiment, the threshold pressure is above an expected occlusion pressure or the pressure at which the artery is occluded. The inflation can be initiated in a manner similar to that described above with reference to FIG. 23A. If the patient monitor 2206 determines that the threshold pressure has not been reached, the inflatable cuff 2204 continues to inflate. However, if the patient monitor 2206 determines that the threshold pressure has been reached, the process moves to block 2454.

At block 2454, the patient monitor 2206 actuates the valve to initiate deflation of the inflatable cuff 2206. In one embodiment, the valve is a three-way valve similar to valve 2216 of FIG. 21, such that the inflation of the inflatable cuff 2204 ends at the same time deflation begins. Once the deflation of the inflatable cuff 2204 begins, the process moves to block 2456 and the patient monitor receives blood pressure data, filters the blood pressure data 2458, and determines blood pressure 2460. Greater detail regarding receiving blood pressure data 2456, filtering the blood pressure data 2458 and determining blood pressure is described above with reference to blocks 2404-2408 of FIG. 23A.

Fewer, more, or different blocks can be added to the process 2400B without departing from the spirit and scope of the description. For example, the patient monitor 2206 can determine the systolic pressure prior to receiving the blood pressure data or filtering the blood pressure data to determine the diastolic pressure. In addition, the process 2400B can be implemented without the use of the patient monitor 2206. For example, a user can receive blood pressure data via a stethoscope. The user can determine the blood pressure of the wearer using Korotkoff sounds, and can also determine the blood pressure of the wearer without filtering the blood pressure data. Furthermore, process 2400A and 2400B can be combined and measurements taken during inflation and deflation of the inflatable cuff. Furthermore, the measurements taken during deflation of the inflatable cuff can be used to verify the blood pressure readings taken during inflation of the inflatable cuff 2204.

Figure 24:
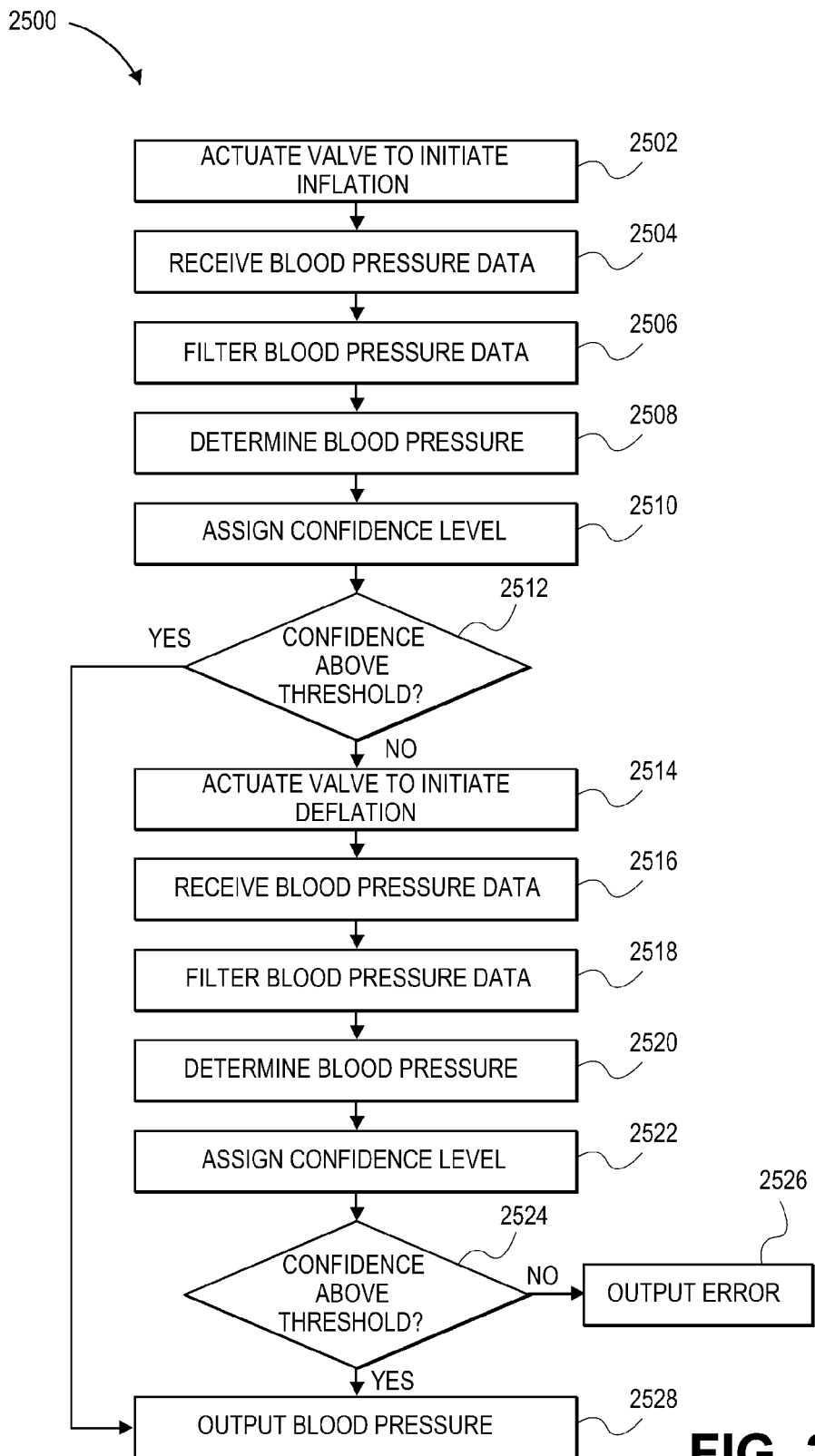
FIG. 24 is a flow diagram illustrating another embodiment of a process implemented by the patient monitor for measuring blood pressure of a wearer.

FIG. 24 is a flow diagram illustrating another embodiment of a process 2500 implemented by the patient monitor for measuring blood pressure of a wearer. FIG. 24 is similar in many respects to FIGS. 23A and 23B. For example, blocks 2502-2508 of FIG. 24 correspond to blocks 2402-2408 of FIG. 23A, respectively. Furthermore, blocks 2514-2520 correspond to blocks 2454-2460 of FIG. 23B, respectively.

As described above with reference to FIG. 23A and illustrated in blocks 2502-2508, the patient monitor 2206 actuates a valve to initiate inflation, receives blood pressure data during inflation, filters the blood pressure data, and determines the blood pressure of the wearer. Upon determining the blood pressure of the wearer, the patient monitor assigns a confidence level to the blood pressure measurements, as illustrated in block 2510. The confidence level assigned can be determined in any number of ways. For example, based on the amount and magnitude of the noise observed in the blood pressure data, the patient monitor can assign the confidence level. Alternatively, if an anomaly in the blood pressure data is detected or if the blood pressure data deviates beyond a threshold level a lower confidence level can be assigned to the blood pressure measurements.

At determination block 2512, the patient monitor 2206 determines if the confidence level assigned to the inflationary blood pressure measurements are above a threshold confidence level. The threshold confidence level can be determined based on previous blood pressure measurements, historical information, clinical data from one or more wearers, or the like. If the confidence level assigned to the blood pressure measurements during inflation exceeds the threshold confidence level, the patient monitor 2206 outputs the inflationary blood pressure measurements, as illustrated in block 2528. The inflationary blood pressure measurements can be output to a display, a printer, another patient monitor, etc. Once output, the patient monitor 2206 can actuate a valve to deflate the inflatable cuff 2204 at a rate greater than would be used if the blood pressure measurements were taken during deflation. Alternatively, the patient monitor 2206 can deflate the inflatable cuff 2204 at the same rate as when blood pressure measurements taken during deflation.

If on the other hand, the confidence level assigned to the inflationary blood pressure measurements is less than the threshold confidence level, then the patient monitor can actuate the valve to initiate deflation of the inflatable cuff, as illustrated in block 2514. As blocks 2514-2520 correspond to blocks 2454-2460 of FIG. 23B, additional details with respect to blocks 2514-2520 are provided above with reference to FIG. 23B.

Upon determining the blood pressure during deflation, the patient monitor 2206 can assign a confidence level to the deflationary blood pressure measurements, as illustrated in block 2522 and described in greater detail above with reference to block 2510. Upon assigning the confidence level to the deflationary blood pressure measurements, the patient monitor 2206 determines if the confidence level exceeds a threshold confidence, as illustrated in determination block 2524, similar to the determination made in block 2512. If the patient monitor 2206 determines that the confidence level assigned to the deflationary blood pressure measurements does not exceed the confidence threshold, the patient monitor 2206 can output an error, as illustrated in block 2526. The error can indicate that neither the inflationary blood pressure measurements nor the deflationary blood pressure measurements exceeded the confidence threshold. In addition, the patient monitor 2206 can recommend that additional blood pressure measurements be taken.

If on the other hand, the patient monitor determines that the confidence level assigned to the deflationary blood pressure measurements exceeds the confidence threshold, the patient monitor outputs the deflationary blood pressure measurements, as shown in block 2528.

Fewer, more, or different blocks can be added to the process 2500 without departing from the spirit and scope of the description. For example, in an embodiment, the patient monitor 2206 automatically returns to step 2502 upon outputting the error or determining that the confidence level did not exceed the confidence threshold, and repeats the process 2500. In yet another embodiment, the patient monitor 2206 outputs the error as well as the blood pressure measurements having the highest confidence level.

Figure 25:
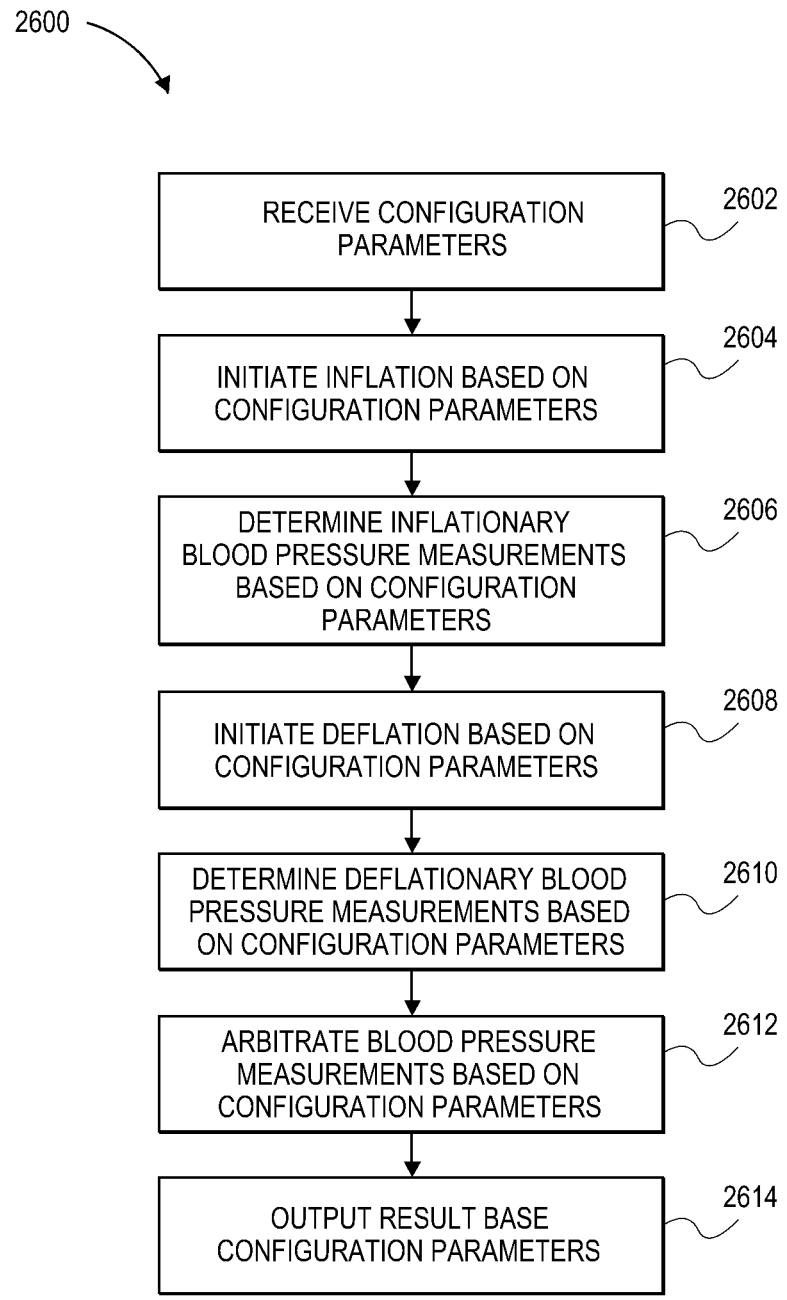
FIG. 25 is a flow diagram illustrating yet another embodiment of a process implemented by the patient monitor for measuring blood pressure of a wearer.

FIG. 25 is a flow diagram illustrating yet another embodiment of a process 2600 implemented by the patient monitor 2206 for measuring blood pressure of a wearer. At block 2602, the patient monitor 2206 receives configuration parameters. The configuration parameters can be set by a user, another patient monitor, or preset. The configuration parameters can include when to measure blood pressure, how to calculate the diastolic and systolic blood pressure, what measurements to display, confidence thresholds, etc. For example the configuration parameters can include whether to take blood pressure measurements during inflation, deflation, or both. In addition, the configuration parameters can include information regarding what process to use to determine the blood pressure measurements. For example, the patient monitor can determine the blood pressure measurements using the measured arterial pressure, the slopes of the pressure oscillations, maximum deflection points of the filtered blood pressure data, or other criteria. The configuration parameters can also include the confidence level to be used in determining whether the blood pressure measurements should be accepted. Furthermore, the configuration parameters can include what blood pressure measurements are to be output and how to determine which blood pressure measurements to output. For example, the configuration parameters can dictate that only blood pressure measurements having a confidence level greater than a threshold are to be output, or that the blood pressure measurements having the highest threshold are to be output. Additionally, the configuration parameters can dictate that both blood pressure measurements, average blood pressure measurements, and the like are to be output. Furthermore, the configuration parameters can include the frequency with which the blood pressure measurements are to be taken.

At block 2604, the patient monitor initiates inflation based on the received configuration parameters. For example, the configuration parameters can dictate the rate at which the inflatable cuff 2204 is to be inflated using the gas reservoir 2202. In an embodiment, the inflatable cuff 2204 is inflated at an approximately constant rate. In another embodiment, the inflatable cuff is not inflated at an approximately constant rate. In an embodiment, the inflatable cuff 2204 is inflated in a relatively short amount of time or at a very high rate of inflation. In another embodiment, the inflatable cuff 2204 is inflated more slowly.

At block 2606 the inflationary blood pressure measurements are determined by the patient monitor 2606 based on the configuration parameters. The configuration parameters can dictate whether and what method to use in determining the inflationary blood pressure measurements. Furthermore, the configuration parameters can dictate whether the blood pressure data is filtered and how. In an embodiment, the configuration parameters dictate that the inflationary blood pressure measurements are not to be taken based on the inflation rate. In another embodiment, the patient monitor determines the inflationary blood pressure measurements based on the slope and magnitude of the oscillations of the filtered blood pressure data during inflation based on the configuration parameters. In addition, the patient monitor can set confidence levels and perform other operations based on the configuration parameters.

Upon determining the inflationary blood pressure measurements, the patient monitor initiates deflation of the inflatable cuff 2204 based on the configuration parameters. The configuration parameters can dictate the time and rate at which the inflatable cuff 2204 deflates. For example, the configuration parameters can dictate a threshold pressure that when reached initiates the deflation. The threshold pressure can be based on personal information of the wearer or general safety levels. In an embodiment, the patient monitor initiates deflation based on a threshold pressure being reached for a predefined period of time based on the configuration parameters. In another embodiment, the patient monitor initiates deflation once the inflationary blood pressure measurements are taken.

Upon initiating deflation, the patient monitor determines deflationary blood pressure measurements based on one or more configuration parameters, as illustrated in block 2610. As discussed previously, with reference to block 2606 the configuration parameters can include any number of parameters that determine if and how the deflationary blood pressure measurements are taken, as well as if and how the blood pressure data is filtered. In addition, the patient monitor can set confidence levels and perform other operations based on the configuration parameters.

Upon determining the deflationary blood pressure measurements, the patient monitor arbitrates blood pressure measurements based on the configuration parameters. The patient monitor can arbitrate the blood pressure measurements based on any number of configuration parameters. For example, the patient monitor can arbitrate the blood pressure measurements based on the highest confidence level or whether a threshold confidence level was reached. Furthermore, the patient monitor can arbitrate based on expected values, previous values, averages or the like. Alternatively, the patient monitor can select both the inflationary and deflationary blood pressure measurements.

At block 2614, the patient monitor outputs the results of the arbitration based on the configuration parameters. The output can include the inflationary blood pressure measurements, the deflationary blood pressure measurements, both or a combination of the two. The output can further include additional information, such as inflation rate, deflation rate, average blood pressure measurements depending on whether they were determined during inflation or deflation, etc.

VIII. Terminology

Many other variations than those described herein will be apparent from this disclosure. For example, depending on the embodiment, certain acts, events, or functions of any of the algorithms described herein can be performed in a different sequence, can be added, merged, or left out all together (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, any of the signal processing algorithms described herein may be implemented in analog circuitry. A computing environment can include any type of computer system, including, but not limited to, a computer system based on a microprocessor, a mainframe computer, a digital signal processor, a portable computing device, a personal organizer, a device controller, and a computational engine within an appliance, to name a few.

The steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An exemplary storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. A method of measuring blood pressure, the method comprising:
    obtaining a baseline photoplethysmograph signal from an optical sensor coupled to a measurement site of the patient before a deliberate movement of the measurement site;
    obtaining a motion induced photoplethysmograph signal from the optical sensor coupled with the patient at the measurement site that is in motion;
    obtaining a motion signal from a motion sensor coupled with the measurement site;
    estimating a motion component of the motion induced photoplethysmograph signal responsive to the deliberate movement based at least on the motion signal and the baseline photoplethysmograph signal;
    normalizing the motion portion with respect to acceleration and perfusion to generate an output normalized signal;
    supplying the output normalized signal into a cuff trigger module to determine whether the output normalized signal exceeds a threshold;
    generating a triggering signal to a blood pressure cuff based on the output normalized signal exceeding the threshold;
    controlling an operation of the blood pressure cuff in response to the triggering signal; and
    calculating, by a hardware processor, a blood pressure based on the normalized motion portion instead of deriving the blood pressure from an estimated plethysmograph portion of the motion induced photoplethysmograph signal and based on the operation of the blood pressure cuff.

2. The method of claim 1, wherein the motion sensor comprises an accelerometer.

3. The method of claim 1, further comprising inducing the motion at the measurement site with a motion inducer.

4. The method of claim 3, wherein the motion inducer comprises a motor.

5. The method of claim 1, further comprising one or more basis functions to values of the motion portion prior to normalizing the motion portion.

6. The method of claim 5, further comprising determining weights associated with the one or more basis functions based on a measurement from the blood pressure cuff.

7. The method of claim 6, where the one or more basis functions comprise both linear and non-linear functions.

\* \* \* \* \*